US011858980B2

(12) United States Patent
Viswanathan et al.

(10) Patent No.: US 11,858,980 B2
(45) Date of Patent: *Jan. 2, 2024

(54) ENGINEERED POLYPEPTIDES AND USES THEREOF

(71) Applicant: VISTERRA, INC., Waltham, MA (US)

(72) Inventors: Karthik Viswanathan, Acton, MA (US); Boopathy Ramakrishnan, Braintree, MA (US); Brian Booth, West Roxbury, MA (US); Kristin Narayan, Lexington, MA (US); Andrew M. Wollacott, Milton, MA (US)

(73) Assignee: VISTERRA, INC., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/667,309

(22) Filed: Aug. 2, 2017

(65) Prior Publication Data
US 2018/0037634 A1    Feb. 8, 2018

Related U.S. Application Data

(60) Provisional application No. 62/485,671, filed on Apr. 14, 2017, provisional application No. 62/370,201, filed on Aug. 2, 2016.

(51) Int. Cl.
C07K 16/00 (2006.01)
C12P 21/08 (2006.01)
A61K 39/395 (2006.01)
A61K 39/40 (2006.01)
C07K 16/10 (2006.01)
C07K 16/12 (2006.01)
C07K 1/00 (2006.01)
A61K 39/00 (2006.01)

(52) U.S. Cl.
CPC .............. *C07K 16/00* (2013.01); *C07K 16/10* (2013.01); *C07K 16/1027* (2013.01); *C07K 16/1081* (2013.01); *C07K 16/1282* (2013.01); *A61K 2039/505* (2013.01); *C07K 2317/524* (2013.01); *C07K 2317/526* (2013.01); *C07K 2317/72* (2013.01); *C07K 2317/732* (2013.01); *C07K 2317/734* (2013.01); *C07K 2317/76* (2013.01); *C07K 2317/92* (2013.01); *C07K 2317/94* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,843,708 A | 12/1998 | Hardman et al. | |
| 6,165,745 A | 12/2000 | Ward et al. | |
| 6,737,056 B1 * | 5/2004 | Presta | C07K 16/4291 424/133.1 |
| 6,821,505 B2 | 11/2004 | Ward | |
| 7,083,784 B2 | 8/2006 | Dall'Acqua et al. | |
| 7,122,637 B2 | 10/2006 | Presta | |
| 7,183,387 B1 | 2/2007 | Presta | |
| 7,332,581 B2 | 2/2008 | Presta | |
| 7,335,742 B2 | 2/2008 | Presta | |
| 7,355,008 B2 | 4/2008 | Stavenhagen et al. | |
| 7,371,826 B2 | 5/2008 | Presta | |
| 7,416,727 B2 | 8/2008 | Presta | |
| 7,658,921 B2 | 2/2010 | Dall'Acqua et al. | |
| 7,670,600 B2 | 3/2010 | Dall'Acqua et al. | |
| 7,704,497 B2 | 4/2010 | Dall'Acqua et al. | |
| 7,785,791 B2 | 8/2010 | Presta | |
| 7,790,858 B2 | 9/2010 | Presta | |
| 8,003,774 B2 | 8/2011 | Stavenhagen et al. | |
| 8,012,476 B2 | 9/2011 | Dall'Acqua et al. | |
| 8,088,376 B2 | 1/2012 | Chamberlain et al. | |
| 8,124,731 B2 | 2/2012 | Lazar et al. | |
| 8,163,882 B2 | 4/2012 | Presta | |
| 8,192,737 B2 | 6/2012 | Stavenhagen et al. | |
| 8,318,907 B2 | 11/2012 | Chamberlain et al. | |
| 8,323,962 B2 | 12/2012 | Dall'Acqua et al. | |
| 8,324,351 B2 | 12/2012 | Chamberlain et al. | |
| 8,338,574 B2 | 12/2012 | Chamberlain et al. | |
| 8,367,805 B2 | 2/2013 | Chamberlain et al. | |
| 8,394,925 B2 | 3/2013 | Chamberlain et al. | |
| 8,475,792 B2 | 7/2013 | Dall'Acqua et al. | |
| 8,546,543 B2 | 10/2013 | Lazar | |
| 8,618,251 B1 | 12/2013 | Ravetch et al. | |
| 8,674,083 B2 | 3/2014 | Presta | |
| 8,734,791 B2 | 5/2014 | Lazar et al. | |
| 8,742,074 B2 | 6/2014 | Behrens et al. | |
| 8,795,661 B2 | 8/2014 | Dall'Acqua et al. | |
| 8,802,820 B2 | 8/2014 | Chamberlain et al. | |
| 8,852,586 B2 | 10/2014 | Chamberlain et al. | |
| 8,883,973 B2 | 11/2014 | Chamberlain et al. | |
| 8,952,132 B2 | 2/2015 | Georgiou et al. | |
| 8,969,526 B2 | 3/2015 | Baehner et al. | |
| 9,028,815 B2 | 5/2015 | Stavenhagen et al. | |
| 9,200,079 B2 | 12/2015 | Chamberlain et al. | |
| RE45,992 E | 5/2016 | Behrens et al. | |
| 9,562,100 B2 | 2/2017 | Dall'Acqua et al. | |
| 9,771,426 B2 | 9/2017 | Georgiou et al. | |
| RE46,585 E | 10/2017 | Behrens et al. | |
| 9,803,023 B2 | 10/2017 | Chamberlain et al. | |
| 10,011,660 B2 | 7/2018 | Tsui et al. | |
| 10,253,100 B2 | 4/2019 | Igawa et al. | |
| 10,336,818 B2 | 7/2019 | Chamberlain et al. | |
| 10,556,949 B2 | 2/2020 | Igawa et al. | |

(Continued)

FOREIGN PATENT DOCUMENTS

AU    2012203476 A1    7/2012
AU    2015200990 A1    3/2015
(Continued)

OTHER PUBLICATIONS

Booth et al., "Extending human IgG half-life using structure-guided design," MABS (2018) vol. 10, No. 7, pp. 1098-1110.
(Continued)

*Primary Examiner* — Chun W Dahle
(74) *Attorney, Agent, or Firm* — K&L Gates LLP

(57) ABSTRACT

Polypeptides, such as antibody molecules and fusion proteins, comprising an Fc region, are disclosed. The polypeptides can be used to treat, prevent, and/or diagnose disorders.

22 Claims, 30 Drawing Sheets
Specification includes a Sequence Listing.

(56) References Cited

U.S. PATENT DOCUMENTS

| | | |
|---|---|---|
| 2002/0098193 A1 | 7/2002 | Ward |
| 2003/0157108 A1 | 8/2003 | Presta |
| 2004/0228856 A1 | 11/2004 | Presta |
| 2005/0037000 A1 | 2/2005 | Stavenhagen et al. |
| 2005/0118174 A1 | 6/2005 | Presta |
| 2006/0067930 A1 | 3/2006 | Adams et al. |
| 2006/0194957 A1 | 8/2006 | Presta |
| 2007/0020260 A1 | 1/2007 | Presta |
| 2008/0095762 A1 | 4/2008 | Presta |
| 2008/0274105 A1 | 11/2008 | Presta |
| 2009/0181014 A1 | 7/2009 | Phillips et al. |
| 2010/0098730 A1 | 4/2010 | Lowman et al. |
| 2010/0104564 A1 | 4/2010 | Hansen et al. |
| 2010/0255013 A1 | 10/2010 | Presta |
| 2010/0297103 A1 | 11/2010 | Murakami |
| 2011/0311454 A1 | 12/2011 | Dall'Acqua et al. |
| 2012/0009188 A1 | 1/2012 | Behrens et al. |
| 2012/0100140 A1 | 4/2012 | Reyes et al. |
| 2012/0128663 A1* | 5/2012 | Lazar .......... C07K 16/241 424/133.1 |
| 2012/0213705 A1 | 8/2012 | Dimasi et al. |
| 2013/0131319 A1 | 5/2013 | Igawa et al. |
| 2013/0209473 A1 | 8/2013 | de Sauvage et al. |
| 2013/0330335 A1 | 12/2013 | Bremel et al. |
| 2014/0105889 A1 | 4/2014 | Igawa et al. |
| 2014/0234340 A1 | 8/2014 | Igawa et al. |
| 2014/0294810 A1 | 10/2014 | Lowman et al. |
| 2014/0294812 A1 | 10/2014 | Lazar |
| 2014/0341906 A1 | 11/2014 | Taylor et al. |
| 2014/0356358 A1 | 12/2014 | Sun et al. |
| 2015/0050269 A1 | 2/2015 | Igawa et al. |
| 2015/0166654 A1 | 6/2015 | Igawa et al. |
| 2015/0353630 A1 | 12/2015 | Igawa et al. |
| 2016/0017023 A1 | 1/2016 | Dimasi et al. |
| 2016/0159894 A1 | 6/2016 | Hartmann et al. |
| 2017/0039314 A1 | 2/2017 | Bremel et al. |
| 2017/0260254 A1 | 9/2017 | Monnet et al. |
| 2018/0258161 A1 | 9/2018 | Igawa et al. |
| 2019/0185557 A1 | 6/2019 | Igawa et al. |
| 2019/0233525 A1 | 8/2019 | Igawa et al. |
| 2020/0181257 A1 | 6/2020 | Kuramochi et al. |
| 2020/0277358 A1 | 9/2020 | Viswanathan et al. |
| 2021/0115147 A1 | 4/2021 | Chamberlain et al. |

FOREIGN PATENT DOCUMENTS

| | | |
|---|---|---|
| EP | 1141024 A2 | 10/2001 |
| EP | 1443961 A2 | 8/2004 |
| EP | 1572091 A2 | 9/2005 |
| EP | 1697415 A1 | 9/2006 |
| EP | 1776384 A2 | 4/2007 |
| EP | 1443961 B1 | 5/2009 |
| EP | 1355919 B1 | 11/2010 |
| EP | 2352521 A1 | 8/2011 |
| EP | 2364997 A2 | 9/2011 |
| EP | 2366713 A2 | 9/2011 |
| EP | 2389192 A2 | 11/2011 |
| EP | 1817340 B1 | 5/2012 |
| EP | 2325206 B1 | 3/2014 |
| EP | 2235059 B1 | 2/2015 |
| EP | 2444423 B1 | 3/2015 |
| EP | 2212354 B1 | 4/2015 |
| EP | 2325207 B1 | 3/2017 |
| EP | 2552955 B1 | 5/2017 |
| EP | 1141024 B1 | 8/2018 |
| EP | 2341060 B1 | 2/2019 |
| EP | 2760890 B1 | 7/2019 |
| EP | 2679681 B1 | 8/2019 |
| EP | 3524620 A1 | 8/2019 |
| EP | 2698431 B1 | 9/2020 |
| JP | 2010227116 A | 10/2010 |
| JP | 2010248228 A | 11/2010 |
| JP | 2012136541 A | 7/2012 |
| JP | 5335735 B2 | 11/2013 |
| JP | 5415624 B2 | 2/2014 |
| JP | 5444010 B2 | 3/2014 |
| JP | 2014043405 A | 3/2014 |
| JP | 5542677 B2 | 7/2014 |
| JP | 2016026144 A | 2/2016 |
| JP | 5913980 B2 | 5/2016 |
| JP | 6074360 B2 | 2/2017 |
| JP | 6122072 B2 | 4/2017 |
| JP | 6125949 B2 | 5/2017 |
| JP | 6352634 B2 | 7/2018 |
| JP | 6496702 B2 | 4/2019 |
| JP | 7012104 B2 | 2/2022 |
| WO | 9734631 A1 | 9/1997 |
| WO | 00/42072 A2 | 7/2000 |
| WO | 02/060919 A2 | 8/2002 |
| WO | 2003035835 A2 | 5/2003 |
| WO | 2004004662 A2 | 1/2004 |
| WO | 04/063351 A2 | 7/2004 |
| WO | 04/099249 A2 | 11/2004 |
| WO | 05047327 A2 | 5/2005 |
| WO | 2005070963 A1 | 8/2005 |
| WO | 2006020114 A2 | 2/2006 |
| WO | 06/031370 A2 | 3/2006 |
| WO | 2006053301 A2 | 5/2006 |
| WO | 2006076594 A2 | 7/2006 |
| WO | 2006105062 A2 | 10/2006 |
| WO | 2008030564 A2 | 3/2008 |
| WO | 2008114011 A2 | 9/2008 |
| WO | 2009058492 A2 | 5/2009 |
| WO | 2009086320 A1 | 7/2009 |
| WO | 2010045193 A1 | 4/2010 |
| WO | 2010068722 A1 | 6/2010 |
| WO | 2010085682 A2 | 7/2010 |
| WO | 2010106180 A2 | 9/2010 |
| WO | 2011005481 A1 | 1/2011 |
| WO | 2011119484 A1 | 9/2011 |
| WO | 2011122011 A2 | 10/2011 |
| WO | 2012032080 A1 | 3/2012 |
| WO | 2012073992 A1 | 6/2012 |
| WO | 2012083370 A1 | 6/2012 |
| WO | 2012109133 A1 | 8/2012 |
| WO | 2012115241 A1 | 8/2012 |
| WO | 2012130831 A1 | 10/2012 |
| WO | 2012132067 A1 | 10/2012 |
| WO | 2012133782 A1 | 10/2012 |
| WO | 2013011076 A2 | 1/2013 |
| WO | 2013012733 A1 | 1/2013 |
| WO | 2013046704 A2 | 4/2013 |
| WO | 2013047729 A1 | 4/2013 |
| WO | 2013047752 A1 | 4/2013 |
| WO | 2013081143 A1 | 6/2013 |
| WO | 2013093809 A1 | 6/2013 |
| WO | 2013096221 A1 | 6/2013 |
| WO | 2013/118858 A1 | 8/2013 |
| WO | 2013125667 A1 | 8/2013 |
| WO | 2013180200 A1 | 12/2013 |
| WO | 2013180201 A1 | 12/2013 |
| WO | 2014006217 A1 | 1/2014 |
| WO | 2014177460 A1 | 11/2014 |
| WO | 2014006217 A9 | 2/2015 |
| WO | 2015/175874 A2 | 11/2015 |
| WO | 2015/189249 A1 | 12/2015 |
| WO | 2016016586 A1 | 2/2016 |
| WO | 2016071376 A2 | 5/2016 |
| WO | 2016164480 A1 | 10/2016 |
| WO | 2016177984 A1 | 11/2016 |
| WO | 2017151971 A2 | 9/2017 |
| WO | 2017158426 A1 | 9/2017 |
| WO | 2017181098 A2 | 10/2017 |
| WO | 2019057564 A1 | 3/2019 |

OTHER PUBLICATIONS

Ahmed et al., "Structural characterization of GASDALIE Fc bound to the activating Fc receptor FcgRIIIa," Journal of Structural Biology (2016) vol. 194, No. 1, pp. 78-89.

(56) References Cited

OTHER PUBLICATIONS

Avery et al., "Utility of a human FcRn transgenic mouse model in drug discovery for early assessment and prediction of human pharmacokinetics of monoclonal antibodies," MABS (2016) vol. 8, No. 6, pp. 1064-1078.

Bernstein et al., "Nucleotide sequence of a rabbit IgG heavy chain from the recombinant F-I haplotype," Immunogenetics (1983) vol. 18, No. 4, pp. 387-397.

Borrok et al., "pH-dependent Binding Engineering Reveals an FcRn Affinity Threshold That Governs IgG Recycling," J Biol Chem (2015) vol. 290, No. 7, pp. 4282-4290.

Bruhns et al., "Specificity and affinity of human Fcg receptors and their polymorphic variants for human IgG subclasses," Blood (2009) vol. 113, No. 16, pp. 3716-3725, first published online Nov. 18, 2008.

Chen et al., "Evaluation of a Cetenary PBPK Model for Predicting the In Vivo Disposition of mAbs Engineered for High-Affinity Binding to FcRn," The AAPS Journal (2012) vol. 14, No. 4, pp. 850-859.

Clarkson et al., "Sequence of Ovine IG Gamma-2 Constant Region Heavy Chain CDNA and Molecular Modelling of Ruminant IGG Isotypes," Mol Immunol (1993), vol. 30, No. 13, pp. 1195-1204.

Dall'Acqua et al., "Increasing the affinity of a human IgG1 for the neonatal Fc receptor: biological consequences," J Immunol (2002) vol. 169, No. 9, pp. 5171-5180.

Dall'Acqua et al., "Properties of Human IgG1s Engineered for Enhanced Binding to the Neonatal Fc Receptor (FcRn)" J Biol Chem (2006) vol. 281, No. 33, pp. 23514-23524.

Datta-Mannan et al., "Monoclonal Antibody Clearance: Impact of Modulating the Interaction of IgG with the Neonatal Fc Receptor," J Biol Chem (2007) vol. 282, No. 3, pp. 1709-1717.

Fan et al., "Tissue expression profile of human neonatal Fc receptor (FcRn) in Tg32 transgenic mice," MABS (2016) vol. 8, No. 5, pp. 848-853.

Grevys et al., "Fc Engineering of Human IgG1 for Altered Binding to the Neonatal Fc Receptor affects Fc Effector Functions," J Immunol (2015) vol. 194, pp. 5497-5508.

Hezareh et al., "Effector Function Activities of a Panel of Mutants of a Broadly Neutralizing Antibody against Human Immunodeficiency Virus Type 1," J Virol (2001) vol. 75, No. 24, pp. 12161-12168.

Hinton et al., "Engineered Human IgG Antibodies with Longer Serum Half-lives in Primates," J Biol Chem (2004) vol. 279, No. 8, pp. 6213-6216.

Idusogie et al., "Engineered Antibodies with Increased Activity to Recruit Complement," J Immunol (2001) vol. 166, pp. 2571-2575.

Idusogie et al., "Mapping of the C1q Binding Site on Rituxan, a Chimeric Antibody with a Human IgG1 Fc," J Immunol (2000) vol. 164, pp. 4178-7184.

Kamei et al., "Quantitative Methods for Developing Fc Mutants With Extended Half-Lives," Biotechnology and Bioengineering (2005) vol. 92, No. 6, pp. 748-760.

Kontermann, "Strategies for extended serum half-life of protein therapeutics," Current Opinion in Biotechnology (2011) vol. 22, pp. 868-876.

Lazar et al., "Engineered antibody Fc variants with enhanced effector function," PNAS (206) vol. 103, No. 11, pp. 4005-4010.

Martin et al., "Crystal Structure at 2.8 ANG of an FcRn/Heterodimeric Fc Complex: Mechanism of pH-Dependent Binding," Molecular Cell (2001) vol. 7, No. 4, pp. 867-877.

Monnet et al., "Selection of IgG variants with increased FcRn binding using random and directed mutagenesis: impact on effector functions," Front Immunol (2015) vol. 6, Article 39, 14 pages.

Oganesyan et al., "Structural characterization of a human Fc fragment engineered for lack of effector functions," Acta Cryst (2008) D64, pp. 700-704.

Peipp et al., "Antibody fucosylation differentially impacts cytotoxicity mediated by NK and PMN effector cells," Blood (2008) vol. 112, No. 6, pp. 2390-2399.

Raimund et al., "Differences in promiscuity for antibody-FcRn interactions across species: Implications for therapeutic antibodies," Int'l Immunol (2001) vol. 13, No. 2, pp. 1551-1559.

Rath et al., "The Immunologic Functions of the Neonatal Fc Receptor for IgG," J Clin Immunol (2013) vol. 33(Supp 1) pp. 9-17.

Roopenian et al., "FcRn: the neonatal Fc receptor comes of age," Nat Rev Immunol (2007) vol. 7, No. 9, pp. 715-725.

Ryan et al., "Antibody targeting of B-cell maturation antigen on malignant plasma cells," Mol Cancer Ther (2007) vol. 6, No. 11, pp. 3009-3018.

Saxena et al., "Advances in Therapeutic Fc Engineering-Modulation of IgG-Associated Effector Functions and Serum Half-life," Front Immunol (2016) vol. 7, Article 580, 11 pages.

Shields et al., "High Resolution Mapping of the Binding Site on Human IgG1 for FcgRI, FcgRII, FcgRIII, and FcRn and Design of IgG1 Variants with Improved Binding to the FcgR," J Biol Chem (2001) vol. 276, No. 9, pp. 6591-6604.

Stewart et al., "A variant human IgG1-Fc mediates improved ADCC," Protein Engineering, Design & Selection (2011) vol. 24, No. 9, pp. 671-678.

Suzuki et al., "Therapeutic antibodies: their mechanisms of action and the pathological findings they induce in toxicity studies," J Toxicol Pathol (2015) vol. 28, pp. 133-139.

Tam et al., "Correlations between pharmacokinetics of IgG antibodies in primates vs. FcRn-transgenic mice reveal a rodent model with predictive capabilities," MABS (2013) vol. 5, No. 3, pp. 397-405.

Ward et al., "Targeting FcRn for the modulation of antibody dynamics," Molecular Immunology (2015) vol. 67, pp. 131-141.

Yeung et al., "A Therapeutic Anti-VEGF Antibody with Increased Potency Independent of Pharmacokinetic Half-life," Cancer Research (2010) vol. 70, No. 8, pp. 3269-3277.

Zalevsky et al., "Enhanced antibody half-life improves in vivo activity," Nat Biotechnol (2010) vol. 28, No. 2, pp. 157-159.

Zhang et al., "Fc Engineering Approaches to Enhance the Agonism and Effector Functions of an Anti-OX40 Antibody," J Biol Chem (2016) vol. 291, No. 53, pp. 27134-27146.

International Search Report and Written Opinion issued in PCT/US2017/045126, dated Jan. 8, 2018.

Search Report and Written Opinion issued in Singapore Patent Application No. 11201900616U, dated May 28, 2020, 17 pages.

Pakula et al., "Genetic analysis of protein stability and function," Annu. Rev. Genet. (1989), vol. 23, pp. 289-310.

Frankel et al., "Characterization of diphtheria fusion proteins targeted to the human interleukin-3 receptor," Protein Engineering (2000), vol. 13, No. 8, pp. 575-581.

Roitt, I. et al. "Immunology," Moscow, "Mir" (2000) pp. 110, 111 & 132.

Badri, H. et al. "Optimization of radiation dosing schedules for proneural glioblastoma." Journal of Mathematical Biology vol. 72,5 (2016): 1301-36. Epub Jun. 21, 2015.

Baylot, V. et al. "TCTP Has a Crucial Role in the Different Stages of Prostate Cancer Malignant Progression." Results and Problems in Cell Differentiation vol. 64 (2017): 255-261.

* cited by examiner

| Name | Mutation | $k_d$ (fold decrease*) | $k_{on}$ (fold increase*) | $k_{off}$ (fold decrease*) |
|---|---|---|---|---|
| FcMut229 | T256D_H285D_T307R_Q311V_A378V | 14.0 | 3.7 | 3.7 |
| FcMut213 | H285D_T307Q_A378V | 13.2 | 3.8 | 3.3 |
| FcMut215 | T307Q_Q311V_A378V | 12.4 | 3.4 | 3.7 |
| FcMut228 | T256D_N286D_T307R_Q311V_A378V | 12.4 | 3.2 | 4.0 |
| FcMut227 | T256D_H285D_N286D_T307R_A378V | 11.6 | 3.6 | 3.2 |
| FcMut183 | T256D_Q311V_A378V | 11.0 | 3.2 | 3.2 |
| FcMut223 | T256D_H285D_A378V | 10.3 | 3.7 | 2.7 |
| FcMut216 | H285D_Q311V_A378V | 9.6 | 3.4 | 2.8 |
| FcMut186 | T256D_T307R_Q311V_A378V | 9.5 | 2.9 | 3.1 |
| FcMut197 | H285N_T307Q_N315D | 9.1 | 2.9 | 3.0 |
| FcMut171 | T256D_N286D_T307R_Q311V | 8.5 | 2.5 | 3.1 |
| FcMut219 | T256D_N315D_A378V | 7.9 | 2.8 | 2.8 |
| FcMut045 | T256D_T307R_Q311V | 5.9 | 2.3 | 2.6 |
| WT | NONE | 1.0 | 1.0 | 1.0 |
| YTE (Medimmune) | M252Y_S254T_T256E | 8.5 | 2.3 | 3.6 |
| LS (Xencor) | M428L_N434S | 9.2 | 2.6 | 3.6 |

| Mutant | TM (sypro Orange) | SEC elution time (min) | Expi293 Expression (μg/mL) | SDS-PAGE | Protein A |
| --- | --- | --- | --- | --- | --- |
| WT | 68.9 | 8.5 | >80 | ✓ | ++ |
| YTE | 61.7 | 8.5 | >80 | ✓ | ++ |
| LS | 68.0 | 8.5 | >80 | ✓ | ++ |
| FcMut045 | 64.8 | 8.5 | >80 | ✓ | ++ |
| FcMut171 | 64.8 | 8.5 | >80 | ✓ | ++ |
| FcMut183 | 64.0 | 8.5 | >80 | ✓ | ++ |
| FcMut186 | 63.7 | 8.5 | >80 | ✓ | ++ |
| FcMut197 | 68.4 | 8.5 | >80 | ✓ | ++ |
| FcMut213 | 70.2 | 8.5 | >80 | ✓ | ++ |
| FcMut215 | 69.2 | 8.5 | >80 | ✓ | ++ |
| FcMut216 | 65.8 | 8.5 | >80 | ✓ | ++ |
| FcMut219 | 66.7 | 8.5 | >80 | ✓ | ++ |
| FcMut223 | 64.3 | 8.4 | >80 | ✓ | ++ |
| FcMut227 | 66.6 | 8.4 | >80 | ✓ | ++ |
| FcMut228 | 66.7 | 8.5 | >80 | ✓ | ++ |
| FcMut229 | 64.6 | 8.5 | >80 | ✓ | ++ |

FIG. 12

| Group | Half-life (hr) | Fold increase | $C_{max}$ (µg/ml) | $AUC_{inf}$ (hr*µg/ml) | Clearance (ml/hr/kg) |
|---|---|---|---|---|---|
| WT | 32 | | 24.4 | 514.71 | 3.89 |
| FcMut015 | 123 | 3.9 | 24.7 | 1168.46 | 1.71 |
| FcMut045 | 166 | 5.2 | 23.9 | 1540.65 | 1.30 |

| Group | Half-life (hr) | Fold increase | $C_{max}$ (μg/ml) | $AUC_{inf}$ (hr*μg/ml) | Clearance (ml/hr/kg) |
|---|---|---|---|---|---|
| WT | 19 | | 101.5 | 1343.13 | 3.72 |
| FcMut045 | 135 | 7.0 | 112.3 | 2374.28 | 2.11 |
| FcMut183 | 192 | 9.9 | 95.4 | 3216.24 | 1.55 |
| FcMut197 | 165 | 8.6 | 81.7 | 3074.29 | 1.63 |
| FcMut213 | 182 | 9.4 | 107.2 | 3408.52 | 1.47 |

| Group | Half-life (hr) | Fold increase | $C_{max}$ (µg/ml) | $AUC_{inf}$ (hr*µg/ml) | Clearance (ml/hr/kg) |
|---|---|---|---|---|---|
| WT | 22 | | 29.3 | 513.87 | 3.89 |
| YTE | 86 | 3.9 | 26.3 | 1302.33 | 1.54 |
| LS | 87 | 4.0 | 30.6 | 1482.35 | 1.35 |
| FcMut183 | 90 | 4.1 | 24.9 | 1384.34 | 1.44 |
| FcMut197 | 94 | 4.3 | 22.0 | 1191.66 | 1.68 |
| FcMut213 | 96 | 4.4 | 21.4 | 1286.27 | 1.55 |
| FcMut215 | 87 | 4.0 | 27.3 | 1395.92 | 1.43 |
| FcMut228 | 123 | 5.6 | 20.1 | 1509.50 | 1.32 |

| Mutant | FcγRI (ELISA) | FcγRIIA (octet) | FcγRIIB (octet) | FcγRIIIA (ELISA) | C1q (ELISA) |
|---|---|---|---|---|---|
| WT | ++ | ++ | ++ | ++ | ++ |
| YTE | + | + | + | + | ++ |
| LS | ++ | ++ | ++ | ++ | ++ |
| FcMut045 | ++ | ++ | ++ | ++ | ++ |
| FcMut171 | + | ++ | ++ | ++ | ++ |
| FcMut183 | ++ | ++ | +++ | +++ | ++ |
| FcMut186 | +++ | +++ | +++ | +++ | ++ |
| FcMut197 | ++ | ++ | ++ | +++ | + |
| FcMut213 | ++ | +++ | +++ | ++ | ++ |
| FcMut215 | ++ | +++ | +++ | +++ | ++ |
| FcMut216 | ++ | +++ | +++ | ++ | ++ |
| FcMut219 | ++ | +++ | +++ | +++ | ++ |
| FcMut223 | + | +++ | +++ | ++ | ++ |
| FcMut227 | + | +++ | +++ | ++ | + |
| FcMut228 | + | + | ++ | ++ | ++ |
| FcMut229 | ++ | +++ | +++ | ++ | ++ |

FIG. 17A

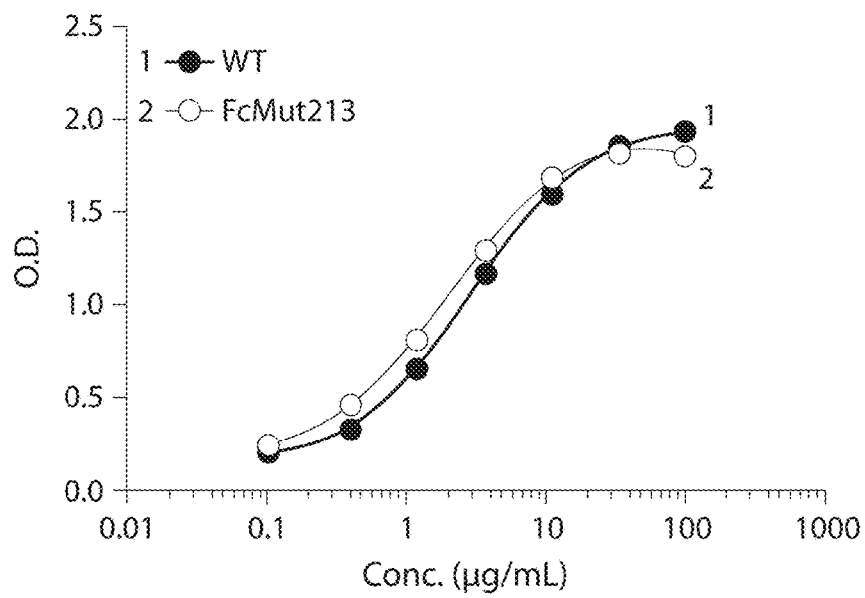

FIG. 17B

| Antibody | Mutations | CDC EC50 (ug/mL)* | C1q binding |
|---|---|---|---|
| RTX WT | None | 0.715 | 0.87 |
| RTX YTE | M252Y_S254T_T256E | > 20 | 1.05 |
| RTX LS | M428L_N434S | 0.352 | 1.05 |
| RTX FcMut045 | T256D_T307R_Q311V | 0.353 | 0.87 |
| RTX FcMut183 | T256D_Q311V_A378V | 0.103 | 1.36 |
| RTX FcMut186 | T256D_T307R_Q311V_A378V | 0.158 | 0.51 |
| RTX FcMut197 | H285N_T307Q_N315D | 2.543 | 0.49 |
| RTX FcMut213 | H285D_T307Q_A378V | 0.267 | 1.09 |
| RTX FcMut215 | T307Q_Q311V_A378V | 0.141 | 1.03 |
| RTX FcMut222 | T256D_T307Q_Q311V | 0.577 | 0.94 |
| RTX FcMut224 | T256D_H285D_T307R_Q311V | 0.576 | 0.82 |
| RTX FcMut226 | T256D_H285D_N286D_T307ER_Q311V | 0.745 | 0.79 |
| RTX FcMut227 | T256D_H285D_N286D_T307R_A378V | 0.228 | 0.99 |
| RTX FcMut228 | T256D_N286D_T307R_Q311V_A378V | 0.220 | 0.89 |
| RTX FcMut229 | T256D_H286D_T307R_Q311V_A378V | 0.140 | 1.29 |
| RTX LALA | L234A_L235A | > 20 | NA |
| RTX FcMut037 | L235V_G236A | > 20 | NA |

FIG. 18

| Set | Amino acids |
|---|---|
| Contact Residues | L251, I253, R255, P257, H285, N286, K288, T307, V308, L309, Q311, L314, H310, H433, N434, H435, Y436 |
| Peripheral Residues | M252, T256, T307, L309, Q311 H433, N434, Y436, N286, K288 |
| Non-contact residues | A287, V308, N315, L314, L432, H429, E430, A431 |
| Residues with potential to modulate 250-helix dynamics | P244, P245, T250, L251, P247 E380, M428, A378, D376, P257, V308, A287, L306, H427 |

| Mutant | ADCC EC$_{50}$ (ng/mL)* |
|---|---|
| WT | 6.14 |
| YTE | 14.98 |
| LS | 4.78 |
| FcMut045 | 6.55 |
| FcMut183 | 3.92 |
| FcMut197 | 8.30 |
| FcMut213 | 4.01 |
| FcMut215 | 2.73 |
| FcMut228 | 2.66 |
| FcMut229 | 3.07 |

| Mutant | CDC EC$_{50}$ (ng/mL)* |
|---|---|
| WT | 0.715 |
| YTE | >20 |
| LS | 0.352 |
| FcMut045 | 0.353 |
| FcMut183 | 0.103 |
| FcMut197 | 2.543 |
| FcMut213 | 0.267 |
| FcMut215 | 0.141 |
| FcMut228 | 0.220 |
| FcMut229 | 0.140 |

| Group | Half-life (hr) | Fold increase | $C_{max}$ (µg/ml) | $AUC_{inf}$ (hr*µg/ml) | Clearance (ml/hr/kg) |
|---|---|---|---|---|---|
| WT | 22 | | 29.3 | 513.87 | 3.89 |
| YTE | 193 | 8.8 | 26.3 | 1682.46 | 1.19 |
| LS | 167 | 7.6 | 30.6 | 1731.27 | 1.16 |
| FcMut183 | 145 | 6.6 | 24.9 | 1689.29 | 1.18 |
| FcMut197 | 170 | 7.8 | 22.0 | 1385.48 | 1.44 |
| FCMut213 | 184 | 8.4 | 21.4 | 1546.14 | 1.29 |
| FcMut215 | 220 | 10.1 | 27.3 | 1587.99 | 1.26 |
| FcMut228 | 207 | 9.5 | 20.1 | 1741.26 | 1.15 |

| Fab | Fc | Mutations | EC$_{50}$ (ug/mL) |
|---|---|---|---|
| Motavizumab | WT | None | 8.50 |
| Motavizumab | YTE | M252Y_S254T_T256E | 10.09 |
| Motavizumab | LS | M428L_N4345 | 14.49 |
| Motavizumab | FcMut045 | T256D_T307R_Q311V | 7.73 |
| Motavizumab | FcMut183 | T256D_Q311V_A378V | 7.41 |
| Motavizumab | FcMut197 | H285N_T307Q_N315D | 12.32 |
| Motavizumab | FcMut213 | H285D_T307Q_A378V | 10.54 |
| Motavizumab | FcMut215 | T307Q_Q311V_A378V | 7.80 |
| Motavizumab | FcMut228 | T256D_N286D_T307R_Q311V_A378V | 10.45 |

FIG. 26

SEQUENCE LISTING

```
<160> NUMBER OF SEQ ID NOS: 2

<210> SEQ ID NO 1
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 1

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5
```

ENGINEERED POLYPEPTIDES AND USES THEREOF

CROSS REFERENCE TO RELATED APPLICATIONS

This application claims the benefit of U.S. Provisional Application No. 62/370,201, filed Aug. 2, 2016, and U.S. Provisional Application No. 62/485,671, filed Apr. 14, 2017. The contents of the aforesaid applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Aug. 1, 2017, is named P2029-701410_SL.txt and is 3,446 bytes in size.

BACKGROUND

Monoclonal antibody therapies are a class of immunotherapies that involve monoclonal antibodies (mAbs) that are capable of specifically interacting with disease-relevant biological molecules. In recent years, the disease areas that therapeutic antibodies can target have significantly expanded, and a number of monoclonal antibodies and antibody-derivative products have been approved for therapeutic use in the United States and many other countries. Monoclonal antibody therapies are currently used or investigated for treating various diseases or conditions, including, for example, infectious diseases, cancer, immune diseases, organ transplantation, cardiovascular diseases, and metabolic diseases.

The efficacy of monoclonal antibodies can be achieved by different mechanisms of action (Suzuki et al. *J Toxicol Pathol*. 2015; 28(3): 133-139). Many therapeutic antibodies neutralize the pathophysiological function of their target molecules or cells. In recent years, monoclonal antibodies that block immune checkpoints have been used to enhance antitumor immunity in cancer patients with the potential to produce durable clinical responses. Certain monoclonal antibodies can trigger antibody-dependent cell-mediated cytotoxic (ADCC) activity or complement-dependent cytotoxic (CDC) activity. Monoclonal antibodies can also be used as drug delivery carriers, for example, when conjugated to radioisotopes, toxins, or other therapeutic or diagnostic agents.

Given the ability of monoclonal antibodies and antibody-derivative products in modulating various biological functions, the need exists for developing new approaches for generation of polypeptides (e.g., antibody molecules or fusion proteins) suitable for treating, preventing, and diagnosing disorders.

SUMMARY

This disclosure provides, at least in part, polypeptides (e.g., antibody molecules or fusion proteins) that comprise an Fc region of an immunoglobulin, and that comprise one or more of the structural or functional properties disclosed herein. In an embodiment, nucleic acid molecules encoding the polypeptides, expression vectors, host cells, compositions (e.g., pharmaceutical compositions), kits, containers, and methods for making the polypeptides (e.g., antibody molecules or fusion proteins), are also provided. The polypeptides (e.g., antibody molecules or fusion proteins) disclosed herein can be used (alone or in combination with other agents or therapeutic modalities) to treat, prevent, and/or diagnose disorders, such as disorders and conditions disclosed herein.

In an aspect, the disclosure features a polypeptide, e.g., an antibody molecule or fusion protein, comprising an Fc region, wherein the Fc region comprises a mutation, and wherein the polypeptide has one or more (e.g., 2, 3, 4, 5, 6, 7, 8, 9, 10, 11, 12, 13, or all) of the following properties:

a) has an increased binding affinity (e.g., a decreased dissociation constant ($K_d$)) for a neonatal Fc receptor (FcRn), e.g., at a pH between 6.0 and 6.5 (e.g., at pH 6.0), e.g., at least 1.5, 2, 3, 4, 5, 6, 7, 8, 9, 10, 15, 20, 30, 40, or 50-fold increase, compared to a reference polypeptide, e.g., as determined by an octet-based assay or a cell-based assay;

b) has a higher binding affinity (e.g., a lower dissociation constant ($K_d$)) for an FcRn at a pH between 6.0 and 6.5 (e.g., at pH 6.0), e.g., at least 1.5, 2, 3, 4, 5, 6, 7, 8, 9, 10, 15, 20, or 50-fold higher, than the binding affinity at a pH between 7.0 and 7.4 (e.g., at pH 7.4), e.g., as determined by an octet-based assay or a cell-based assay;

c) binds to an FcRn with high affinity, e.g., at a pH between 6.0 and 6.5 (e.g., at pH 6.0), e.g., with a dissociation constant ($K_d$) of 300 nM or less, e.g., 250 nM or less, 200 nM or less, 150 nM or less, 100 nM or less, 50 nM or less, e.g., 25 nM or less, 10 nM or less, 5 nM or less, 2 nM or less, 1 nM or less, 0.5 nM or less, 0.2 nM or less, 0.1 nM or less, 0.05 nM or less, 0.02 nM or less, or 0.01 nM or less, e.g., between 25 nM and 0.1 nM, between 20 nM and 0.5 nM, between 15 nM and 1 nM, between 10 nM and 5 nM, or between 20 nM and 10 nM, e.g., as determined by an octet-based assay or a cell-based assay;

d) binds to an FcRn with low affinity e.g., at a pH between 7.0 and 7.4 (e.g., at pH 7.4), e.g., with a $K_d$ of 50 nM or more, e.g., 60 nM or more, 80 nM or more, 100 nM or more, 150 nM or more, 200 nM or more, 500 nM or more, e.g., between 50 nM and 500 nM or between 100 nM and 250 nM, e.g., as determined by an octet-based assay or a cell-based assay;

e) has the same binding affinity, does not substantially alter (e.g., decreases or increases by no more than 10%, 20%, 30%, 40%, 50%, 60%, 70%, 80%, or 90%) the binding affinity, or increases the binding affinity (e.g., by at least 1.5, 2, 3, 4, 5, 6, 7, 8, 9, 10, 15, 20, or 50-fold), for an Fcγ receptor (e.g., one, two, or all of FcγRI, FcγRIIa/b, or FcγRIII), compared to a reference polypeptide, e.g., as determined by an octet-based assay or a cell-based assay;

f) has the same thermal stability, or does not substantially alter (e.g., increases or decreases the melting temperature by no more than 1° C., 2° C., 3° C., 4° C., 5° C., 6° C., 7° C., 8° C., 9° C., or 10° C.), the thermal stability, compared to a reference polypeptide, e.g., as determined by a sypro orange assay;

g) has the same binding affinity, does not substantially alter (e.g., decreases or increases by no more than 10%, 20%, 30%, 40%, 50%, 60%, 70%, 80%, or 90%) the binding affinity, or increases the binding affinity (e.g., by at least 1.5, 2, 3, 4, 5, 6, 7, 8, 9, 10, 15, 20, or 50-fold), for C1q, compared to a reference polypeptide, e.g., as determined by ELISA;

h) has the same binding affinity, does not substantially alter (e.g., decreases or increases by no more than 10%, 20%, 30%, 40%, 50%, 60%, 70%, 80%, or 90%) the binding affinity, or increases the binding affinity (e.g., by at least 1.5, 2, 3, 4, 5, 6, 7, 8, 9, 10, 15, 20, or 50-fold), for TRIM21, compared to a reference polypeptide, e.g., as determined by ELISA;

i) has the same effector function, or does not substantially alter (e.g., decreases or increases by more than 10%, 20%, 30%, 40%, 50%, 60%, 70%, 80%, or 90%) an effector function, or increases an effector function (e.g., by at least 1.5, 2, 3, 4, 5, 6, 7, 8, 9, 10, 15, 20, or 50-fold), e.g., one or more (e.g., two, three, or all) of a complement dependent cytotoxicity (CDC), an antibody dependent cell mediated cytotoxicity (ADCC), an antibody dependent cell mediated phagocytosis (ADCP), or an antibody dependent intracellular neutralization (ADIN), compared to a reference polypeptide;

j) has an increased half-life in vivo, e.g., at least 1.5, 2, 3, 4, 5, 6, 7, 8, 9, or 10-fold increase, compared to a reference polypeptide, e.g., as determined in an animal model;

k) has the same biological function, does not substantially alter (e.g., decreases or increases by no more than 10%, 20%, 30%, 40%, 50%, 60%, 70%, 80%, or 90%) a biological function, or increases a biological function (e.g., by at least 1.5, 2, 3, 4, 5, 6, 7, 8, 9, 10, 15, 20, or 50-fold), in vitro, ex vivo, or in vivo, compared to a reference polypeptide;

l) has the same developability characteristic, does not substantially alter (e.g., decreases or increases by no more than 10%, 20%, 30%, 40%, 50%, 60%, 70%, 80%, or 90%) a developability characteristic, or increases a developability characteristic (e.g., by at least 1.5, 2, 3, 4, 5, 6, 7, 8, 9, 10, 15, 20, or 50-fold), e.g., one or more (e.g., two, three, or all) of stability, solubility, aggregation, or expression level, compared to a reference polypeptide;

m) has the same binding affinity, specificity, or both, or does not substantially alter (e.g., decreases or increases by no more than 10%, 20%, 30%, 40%, 50%, 60%, 70%, 80%, or 90%) the binding affinity, specificity, or both, or increases the binding affinity, specificity, or both (e.g., by at least 1.5, 2, 3, 4, 5, 6, 7, 8, 9, 10, 15, 20, or 50-fold), for an epitope, compared to a reference polypeptide; or n) increases mucosal uptake, e.g., by at least 1.5, 2, 3, 4, 5, 6, 7, 8, 9, 10, 15, 20, 30, 40, or 50-fold, compared to a reference polypeptide, e.g., as determined by a transcytosis assay.

In an embodiment, the polypeptide has an increased binding affinity (e.g., a decreased dissociation constant ($K_d$)) for a neonatal Fc receptor (FcRn), e.g., at a pH between 6.0 and 6.5 (e.g., at pH 6.0), e.g., at least 1.5, 2, 3, 4, 5, 6, 7, 8, 9, 10, 15, 20, 30, 40, or 50-fold increase, compared to a reference polypeptide, e.g., as determined by an octet-based assay or a cell-based assay.

In an embodiment, the polypeptide has a higher binding affinity (e.g., a lower dissociation constant ($K_a$)) for an FcRn at a pH between 6.0 and 6.5 (e.g., at pH 6.0), e.g., at least 1.5, 2, 3, 4, 5, 6, 7, 8, 9, 10, 15, 20, or 50-fold higher, than the binding affinity at a pH between 7.0 and 7.4 (e.g., at pH 7.4), e.g., as determined by an octet-based assay or a cell-based assay.

In an embodiment, the polypeptide binds to an FcRn with high affinity e.g., at a pH between 6.0 and 6.5 (e.g., at pH 6.0), e.g., with a dissociation constant ($K_a$) of 50 nM or less, e.g., 25 nM or less, 10 nM or less, 5 nM or less, 2 nM or less, 1 nM or less, 0.5 nM or less, 0.2 nM or less, 0.1 nM or less, 0.05 nM or less, 0.02 nM or less, or 0.01 nM or less, e.g., between 25 nM and 0.1 nM, between 20 nM and 0.5 nM, between 15 nM and 1 nM, between 10 nM and 5 nM, or between 20 nM and 10 nM, e.g., as determined by an octet-based assay or a cell-based assay.

In an embodiment, the polypeptide binds to an FcRn with low affinity e.g., at a pH between 7.0 and 7.4 (e.g., at pH 7.4), e.g., with a $K_d$ of 50 nM or more, e.g., 60 nM or more, 80 nM or more, 100 nM or more, 150 nM or more, 200 nM or more, 500 nM or more, e.g., between 50 nM and 500 nM or between 100 nM and 250 nM, e.g., as determined by an octet-based assay or a cell-based assay.

In an embodiment, the polypeptide has the same binding affinity, does not substantially alter (e.g., decreases or increases by no more than 10%, 20%, 30%, 40%, 50%, 60%, 70%, 80%, or 90%) the binding affinity, or increases the binding affinity (e.g., by at least 1.5, 2, 3, 4, 5, 6, 7, 8, 9, 10, 15, 20, or 50-fold), for an Fcγ receptor (e.g., one, two, or all of FcγRI, FcγRIIa/b, or FcγRIII), compared to a reference polypeptide, e.g., as determined by an octet-based assay or a cell-based assay.

In an embodiment, the polypeptide has the same thermal stability, or does not substantially alter (e.g., increases or decreases the melting temperature by no more than 1° C., 2° C., 3° C., 4° C., 5° C., 6° C., 7° C., 8° C., 9° C., or 10° C.), the thermal stability, compared to a reference polypeptide, e.g., as determined by a sypro orange assay.

In an embodiment, the polypeptide has the same binding affinity, does not substantially alter (e.g., decreases or increases by no more than 10%, 20%, 30%, 40%, 50%, 60%, 70%, 80%, or 90%) the binding affinity, or increases the binding affinity (e.g., by at least 1.5, 2, 3, 4, 5, 6, 7, 8, 9, 10, 15, 20, or 50-fold), for C1q, compared to a reference polypeptide, e.g., as determined by ELISA.

In an embodiment, the polypeptide has the same binding affinity, does not substantially alter (e.g., decreases or increases by no more than 10%, 20%, 30%, 40%, 50%, 60%, 70%, 80%, or 90%) the binding affinity, or increases the binding affinity (e.g., by at least 1.5, 2, 3, 4, 5, 6, 7, 8, 9, 10, 15, 20, or 50-fold), for TRIM21, compared to a reference polypeptide, e.g., as determined by ELISA.

In an embodiment, the polypeptide has the same effector function, or does not substantially alter (e.g., decreases or increases by more than 10%, 20%, 30%, 40%, 50%, 60%, 70%, 80%, or 90%) an effector function, or increases an effector function (e.g., by at least 1.5, 2, 3, 4, 5, 6, 7, 8, 9, 10, 15, 20, or 50-fold), e.g., one or more (e.g., two, three, or all) of a complement dependent cytotoxicity (CDC), an antibody dependent cell mediated cytotoxicity (ADCC), an antibody dependent cell mediated phagocytosis (ADCP), or an antibody dependent intracellular neutralization (ADIN), compared to a reference polypeptide.

In an embodiment, the polypeptide has an increased half-life in vivo, e.g., at least 1.5, 2, 3, 4, 5, 6, 7, 8, 9, or 10-fold increase, compared to a reference polypeptide, e.g., as determined in an animal model.

In an embodiment, the polypeptide has the same biological function, does not substantially alter (e.g., decreases or increases by no more than 10%, 20%, 30%, 40%, 50%, 60%, 70%, 80%, or 90%) a biological function, or increases a biological function (e.g., by at least 1.5, 2, 3, 4, 5, 6, 7, 8, 9, 10, 15, 20, or 50-fold), in vitro, ex vivo, or in vivo, compared to a reference polypeptide. In an embodiment, the biological function comprises an inhibitory (e.g., neutralizing) activity. In an embodiment, the biological function comprises inhibiting (e.g., neutralizing) a pathogen, e.g., a virus, a bacterium, or a fungus. In an embodiment, the biological function comprising an anti-tumor activity. In an embodiment, the biological function comprises inhibiting an immune response. In an embodiment, the biological function comprises an agonistic activity. In an embodiment, the biological function comprises activating or restoring an immune response.

In an embodiment, the polypeptide has the same developability characteristic, does not substantially alter (e.g., decreases or increases by no more than 10%, 20%, 30%, 40%, 50%, 60%, 70%, 80%, or 90%) a developability characteristic, or increases a developability characteristic (e.g., by at least 1.5, 2, 3, 4, 5, 6, 7, 8, 9, 10, 15, 20, or 50-fold), e.g., one or more (e.g., two, three, or all) of stability, solubility, aggregation, or expression level, compared to a reference polypeptide;

In an embodiment, the polypeptide has the same binding affinity, specificity, or both, or does not substantially alter (e.g., decreases or increases by no more than 10%, 20%, 30%, 40%, 50%, 60%, 70%, 80%, or 90%) the binding affinity, specificity, or both, or increases the binding affinity, specificity, or both (e.g., by at least 1.5, 2, 3, 4, 5, 6, 7, 8, 9, 10, 15, 20, or 50-fold), for an epitope, compared to a reference polypeptide.

In an embodiment, the polypeptide increases mucosal uptake, e.g., by at least 1.5, 2, 3, 4, 5, 6, 7, 8, 9, 10, 15, 20, 30, 40, or 50-fold, compared to a reference polypeptide, e.g., as determined by a transcytosis assay.

In an embodiment, the polypeptide has properties a) or b) above. In an embodiment, the polypeptide has properties a) and b) above. In an embodiment, the polypeptide has one or both of properties a) or b) above, and one or both of properties c) or d) above. In an embodiment, the polypeptide has one or both of properties a) or b) above, and one, two, three, four, or all of properties e), f), g), h), or i) above. In an embodiment, the polypeptide has one or both of properties a) or b) above, and one or both of properties c) or d) above. In an embodiment, the polypeptide has one or both of properties a) or b) above, and one, two, three, four, five, six, or all of properties c), d), j), k), l), m), or n) above. In an embodiment, the polypeptide has one or both of properties a) or b) above, one, two, three, four, or all of properties e), f), g), h), or i) above, and one, two, three, four, five, six, or all of properties c), d), j), k), l), m), or n) above. In an embodiment, the polypeptide has one, two, three, or all of properties a), b), c), or d) above, one, two, three, four, or all of properties e), f), g), h), or i) above, and one, two, three, four, or all of properties j), k), l), m), or n) above. In an embodiment, the polypeptide has one or both of properties a) or c) above, one or both of properties b) or d) above, one, two, three, four, or all of properties e), f), g), h), or i) above, and one, two, three, four, or all of properties j), k), l), m), or n) above.

In an embodiment, the reference polypeptide is an otherwise identical polypeptide without the mutation, e.g., comprising a wild-type Fc region, e.g., having the amino acid sequence of SEQ ID NO: 1, or an amino acid sequence at least about 85%, 90%, 95%, 99% or more identical thereto, or which differs by no more than 1, 2, 3, 4, 5, 6, 7, 8, 9, 10, or 15 amino acid residues.

In an embodiment, the mutation is in a residue in a CH2 domain. In another embodiment, the mutation is in a residue in a CH3 domain. In an embodiment, the polypeptide comprises at least one mutation in a residue in a CH2 domain and at least one mutation in a residue in a CH3 domain. In an embodiment, the polypeptide further comprises a mutation in a residue in a region other than a CH2 domain and/or a CH3 domain.

In an embodiment, the mutation does not alter, or does not substantially alter, the conformation of the linker region between the CH2 and CH3 domains. In an embodiment, the mutation does not introduce a cluster (e.g., 3, 4, 5, 6, 7, 8, 9, 10, or more consecutive) of hydrophobic or aromatic residues, e.g., on a surface region (e.g., a region defined as the area covered by amino acid residues that have more than 20% solvent accessible area).

In an embodiment, the polypeptide is an antibody molecule, e.g., an antibody molecule described herein.

In an embodiment, the polypeptide is an IgG, e.g., IgG1, IgG2, IgG3, or IgG4. In an embodiment, the polypeptide is an IgG1. In an embodiment, the polypeptide is an IgG4.

In an embodiment, the polypeptide comprises a heavy chain immunoglobulin variable region, a light chain immunoglobulin variable region, or both. In an embodiment, the polypeptide comprises a tetramer of two heavy chain immunoglobulin variable regions and two light chain immunoglobulin variable regions. In an embodiment, the polypeptide comprises a full length antibody molecule. In an embodiment, the polypeptide comprises a fragment (e.g., an antigen-binding fragment) of an antibody molecule.

In an embodiment, the polypeptide comprises a chimeric antibody molecule. In an embodiment, the polypeptide comprises a humanized antibody molecule. In an embodiment, the polypeptide comprises a human antibody molecule. In an embodiment, the polypeptide comprises a murine antibody molecule. In an embodiment, the polypeptide comprises a bispecific or multispecific antibody molecule.

In another embodiment, the polypeptide is a fusion protein, e.g., a fusion protein described herein. In an embodiment, the polypeptide comprises a fragment (e.g., functional fragment) of the fusion polypeptide.

In an embodiment, the polypeptide comprises one or more (e.g., 2, 3, 4, or all) of the following:

(i) a mutation in a residue in a surface region (e.g., a region defined as the area covered by amino acid residues that have more than 20% solvent accessible area) that interacts with the FcRn, e.g., an FcRn contact residue;

(ii) a mutation in a residue that is a peripheral residue along the Fc-FcRn interface (e.g., any amino acid residues on the surface of the Fc region that is less than 7 Angstroms from the FcRn in the Fc-FcRn complex);

(iii) a mutation is in a residue that is non-contact residue in Fc-FcRn binding;

(iv) a mutation in a residue which is a helix contact reside that enhances the conformational dynamics of 250-helix, e.g., a helix comprising one or more (e.g., 2, 3, 4, 5, or all) of P247, K248, D249, T250, L251, or M252; or (v) a mutation, which modulates pK of a histidine and/or is an introduction of a histidine along the Fc-FcRn interface (e.g., any amino acid residues on the surface of the Fc region that is less than 7 Angstroms from the FcRn in the Fc-FcRn complex).

In an embodiment, the polypeptide comprises (i) and (ii) above. In an embodiment, the polypeptide comprises (i) and (iii) above. In an embodiment, the polypeptide comprises (i) and (iv) above. In an embodiment, the polypeptide comprises (i) and (v) above. In an embodiment, the polypeptide comprises (ii) and (iii) above. In an embodiment, the polypeptide comprises (ii) and (iv) above. In an embodiment, the polypeptide comprises (ii) and (v) above. In an embodiment, the polypeptide comprises (iii) and (iv) above. In an embodiment, the polypeptide comprises (iii) and (v) above. In an embodiment, the polypeptide comprises (iv) and (v) above.

In an embodiment, the polypeptide comprises (i), (ii) and (iii) above. In an embodiment, the polypeptide comprises (i), (ii) and (iv) above. In an embodiment, the polypeptide comprises (i), (ii) and (v) above. In an embodiment, the polypeptide comprises (i), (iii) and (iv) above. In an embodiment, the polypeptide comprises (i), (iii) and (iv) above. In an embodiment, the polypeptide comprises (i), (iv) and (v) above. In an embodiment, the polypeptide comprises (ii), (iii) and (iv) above. In an embodiment, the polypeptide comprises (ii), (iii) and (v) above. In an embodiment, the polypeptide comprises (ii), (iv) and (v) above. In an embodiment, the polypeptide comprises (iii), (iv) and (v) above.

In an embodiment, the polypeptide comprises (i), (ii), (iii) and (iv) above. In an embodiment, the polypeptide comprises (i), (ii), (iii) and (v) above. In an embodiment, the polypeptide comprises (i), (ii), (iv) and (v) above. In an embodiment, the polypeptide comprises (i), (iii), (iv) and (v) above. In an embodiment, the polypeptide comprises (ii), (iii), (iv) and (v) above.

In an embodiment, the polypeptide comprises (i), (ii), (iii), (iv), and (v) above.

In an embodiment, the polypeptide comprises a mutation in a residue in a surface region (e.g., a region defined as the area covered by amino acid residues that have more than 20% solvent accessible area) that interacts with the FcRn, e.g., an FcRn contact residue.

In an embodiment, the mutation is in a residue chosen from: L251, I253, R255, P257, H285, N286, K288, T307, V308, L309, Q311, L314, H310, H433, N434, H435, or Y436. In an embodiment, the polypeptide comprises a plurality of mutations in two or more (e.g., 3, 4, 5, 6, 7, 8, 9, 10, 11, 12, 13, 14, 15, 16, or all) of the residues chosen from L251, I253, R255, P257, H285, N286, K288, T307, V308, L309, Q311, L314, H310, H433, N434, H435, or Y436.

In an embodiment, the polypeptide comprises a mutation in a residue that is a peripheral residue along the Fc-FcRn interface (e.g., any amino acid residues on the surface of the Fc region that is less than 7 Angstroms from the FcRn in the Fc-FcRn complex).

In an embodiment, the mutation is in a residue chosen from one or more (e.g., 2, 3, 4, 5, 6, or all) of T256, H285, N286, T307, Q311, N315, or A378. In an embodiment, the polypeptide comprises a plurality of mutations in two or more (e.g., 2, 3, 4, 5, 6, or all) of the residues chosen from T256, H285, N286, T307, Q311, N315, or A378. In an embodiment, the polypeptide comprises one or more (e.g., 2, 3, 4, 5, 6, or all) of the mutations chosen from T256D, H285N, N286D, T307Q, Q311V, N315D, or A378V.

In an embodiment, the mutation is in a residue chosen from T256, Q311, or A378. In an embodiment, the polypeptide comprises a plurality of mutations in two or all of the residues chosen from T256, Q311, or A378. In an embodiment, the polypeptide comprises one, two, or all of the mutations chosen from T256D, Q311V, or A378V.

In an embodiment, the mutation is in a residue chosen from H285, T307, or N315. In an embodiment, the polypeptide comprises a plurality of mutations in two or all of the residues chosen from H285, T307, or N315. In an embodiment, the polypeptide comprises one, two, or all of the mutations chosen from H285N, T307Q, or N315D.

In an embodiment, the mutation is in a residue chosen from H285, T307, or A378. In an embodiment, the polypeptide comprises a plurality of mutations in two or all of the residues chosen from H285, T307, or A378. In an embodiment, the polypeptide comprises one, two, or all or the mutations chosen from H285D, T307Q, or A378V.

In an embodiment, the mutation is in a residue chosen from T307, Q311, or A378. In an embodiment, the polypeptide comprises a plurality of mutations in two or all of the residues chosen from T307, Q311, or A378. In an embodiment, the polypeptide comprises one, two, or all of the mutations chosen from T307Q, Q311V, or A378V.

In an embodiment, the mutation is in a residue chosen from T256, N286, T307, Q311, or A378. In an embodiment, the polypeptide comprises a plurality of mutations in two, three, four, or all of the residues chosen T256, N286, T307, Q311, or A378. In an embodiment, the polypeptide comprises one, two, three, four, or all of the mutations chosen from T256D, N286D, T307R, Q311V, or A378V.

In an embodiment, the mutation is in a residue chosen from T256, H285, T307, Q311, or A378. In an embodiment, the polypeptide comprises a plurality of mutations in two, three, four, or all of the residues chosen T256, H285, T307, Q311, or A378. In an embodiment, the polypeptide comprises one, two, three, four, or all of the mutations chosen from T256D, H285D, T307R, Q311V, or A378V.

In an embodiment, the mutation is in a residue chosen from M252, T256, T307, L309, Q311, H433, N434, Y436, N286, or K288. In an embodiment, the polypeptide comprises a plurality of mutations in two or more (e.g., 3, 4, 5, 6, 7, 8, 9, or all) of the residues chosen from M252, T256, T307, L309, Q311, H433, N434, Y436, N286, or K288.

In an embodiment, the polypeptide comprises a mutation is in a residue that is non-contact residue in Fc-FcRn binding.

In an embodiment, the mutation is in a residue chosen from A287, V308, N315, L314, L432, H429, E430, or A431. In an embodiment, the polypeptide comprises a plurality of mutations in two or more (e.g., 3, 4, 5, 6, 7, or all) of the residues chosen from A287, V308, N315, L314, L432, H429, E430, or A431.

In an embodiment, the polypeptide comprises a mutation in a residue which is a helix contact reside that enhances the conformational dynamics of 250-helix (e.g., a helix comprising one or more (e.g., 2, 3, 4, 5, or all) of P247, K248, D249, T250, L251, or M252), e.g., a lateral displacement or conformational flexibility exhibited by the 250-helix (e.g., as shown by a comparison of the crystal structures of the Fc domain crystallized at pH5.0 (PDB ID: 4J12) and at pH 6.5 (PDB ID: 4Q7D).

In an embodiment, the mutation is in a residue chosen from P244, P245, T250, L251, P247, E380, M428, A378, D376, P257, V308, A287, L306, or H427. In an embodiment, the polypeptide comprises a plurality of mutations in two or more (e.g., 3, 4, 5, 6, 7, 8, 9, 10, 11, 12, 13, or all) of the residues chosen from P244, P245, T250, L251, P247, E380, M428, A378, D376, P257, V308, A287, L306, or H427.

In an embodiment, the polypeptide comprises a mutation which is the introduction of a histidine along the Fc-FcRn interface (e.g., any amino acid residues on the surface of the Fc region that is less than 7 Angstroms from the FcRn in the Fc-FcRn complex).

In an embodiment, the mutation introduces a polar amino acid residue. In another embodiment, the mutation introduces a non-polar amino acid residue. In an embodiment, the mutation introduces a charged amino acid residue. In another embodiment, the mutation introduces a non-charge amino acid residue. In an embodiment, the mutation introduces a positively charged (or basic) amino acid residue. In another embodiment, the mutation introduces a negatively charged (or acidic) amino acid residue. In an embodiment, the mutation introduces a hydrophobic amino acid residue. In another embodiment, the mutation introduces a hydrophilic amino acid residue.

In an embodiment, the polypeptide comprises a mutation in at least one (e.g., 2, 3, 4, 5, or more) FcRn contact residue.

In an embodiment, the polypeptide comprises a mutation in one or more (e.g., 2 or all) of residues T256, T307, or N286. In an embodiment, the polypeptide comprises mutations in residues T256 and T307, optionally, further comprises a mutation in residue N286. In an embodiment, the mutation in residue T256 is a polar residue, e.g., chosen from T256D, T256E, or T256R. In an embodiment, the mutation in residue T256 is T256D. In an embodiment, the mutation in residue T307 is a polar residue, e.g., chosen from T307D, T307E, or T307R. In an embodiment, the mutation in residue T307 is T307R. In an embodiment, the mutation in residue N286 is N286I. In an embodiment, the polypeptide comprises mutations T256D and T307R. In an embodiment, the polypeptide comprises mutations T256D, T307R, and N286I.

In an embodiment, the polypeptide comprises a mutation in at least one (e.g., 2, 3, 4, 5, or more) FcRn contact residue. In an embodiment, the polypeptide comprises a mutation in one or more (e.g., 2 or all) of residues L309, D312, or N315. In an embodiment, the polypeptide comprises a mutation in residue L309, optionally, further comprises mutations in residues D312 and N315. In an embodiment, the mutation in residue L309 is L309N. In an embodiment, the mutation in residue D312 is D312A. In an embodiment, the mutation in residue N315 is N315D. In an embodiment, the polypeptide comprises mutation L309N. In an embodiment, the polypeptide comprises mutations L309N, D312A and N315D.

In an embodiment, the polypeptide comprises a mutation in at least one (e.g., 1, 2, 3, 4, 5, or more) FcRn non-contact residue. In an embodiment, the polypeptide comprises a mutation in one or more (e.g., 2 or all) of residues L209R, D312, or Q311. In an embodiment, the polypeptide comprises mutations in residues L309 and D312, optionally, further comprising a mutation in residue Q311. In an embodiment, the polypeptide comprises a mutation in residue Q311. In an embodiment, the mutation in residue L309 is L309R. In an embodiment, the mutation in residue D312 is D312E. In an embodiment, the mutation in residue Q311 is Q311P. In an embodiment, the polypeptide comprises mutations L309R and D312E. In an embodiment, the polypeptide comprises mutations L309R, D312E, and Q311P. In an embodiment, the polypeptide comprises mutation Q311P.

In an embodiment, the polypeptide comprises a mutation in at least one (e.g., 2, 3, 4, 5, or more) FcRn contact residue. In an embodiment, the polypeptide comprises a mutation in one or more (e.g., 2, 3, or 4) of residues chosen from I253, S254, M252, or R255. In an embodiment, the polypeptide comprises a mutation in residue I253. In an embodiment, the mutation in residue I253 is I253M. In an embodiment, the polypeptide comprises a mutation in residue S254. In an embodiment, the mutation in residue S254 is S254H or S254M. In an embodiment, the polypeptide comprises mutations in residues M252 and S254. In an embodiment, the mutation in residue M252 is M252E. In an embodiment, the mutation in residue S254 is S254R. In an embodiment, the polypeptide comprises mutations in residues M252, S254, and R255. In an embodiment, the mutation in residue M252 is M252E. In an embodiment, the mutation in residue S254 is S254R. In an embodiment, the mutation in residue R255 is R255Y.

In an embodiment, the polypeptide comprises a mutation in at least one (e.g., 2, 3, 4, 5, or more) FcRn non-contact residue. In an embodiment, the polypeptide comprises mutations that are equivalent of T250Q and M34L. In an embodiment, the polypeptide comprises a mutation in one or more (e.g., 2, 3, 4, or all) of residues chosen from D376, K248, E380, M428, or A328. In an embodiment, the polypeptide comprises a mutation in residue D376 and a mutation in a residue chosen from K248, E380, M428, or A328. In an embodiment, the polypeptide comprises a mutation in residue D376 and a mutation in residue K248. In an embodiment, the polypeptide comprises a mutation in residue D376 and a mutation in residue E380. In an embodiment, the polypeptide comprises a mutation in residue D376 and a mutation in residue M428. In an embodiment, the polypeptide comprises a mutation in residue D376 and a mutation in residue A328. In an embodiment, the mutation in residue D376 is D376Q or D376N. In an embodiment, the mutation in residue K248 is K248S. In an embodiment, the mutation in residue E380 is E380A. In an embodiment, the mutation in residue D376 is D376Q. In an embodiment, the mutation in residue M428 is M428L. In an embodiment, the mutation in residue A328 is A328I. In an embodiment, the polypeptide comprises mutation D376Q or D376N, and mutation K248S. In an embodiment, the polypeptide comprises mutation D376Q or D376N, and mutation E380A. In an embodiment, the polypeptide comprises mutations D376Q and M428L. In an embodiment, the polypeptide comprises mutations D376Q and A328I.

In an embodiment, the polypeptide comprises a mutation in at least one (e.g., 2, 3, 4, 5, or more) FcRn non-contact residue. In an embodiment, the polypeptide comprises a mutation in one or more (e.g., 2 or all) of residues chosen from K246, P247, or D376. In an embodiment, the polypeptide comprises a mutation in residue K246 and a mutation in residue P247, optionally, further comprising a mutation in residue D376. In an embodiment, the mutation in residue K246 is K246N. In an embodiment, the mutation in residue P247 is P247A. In an embodiment, the mutation in residue D376 is D376N. In an embodiment, the polypeptide comprises mutations K246N and P247A, optionally, further comprising mutation D376N.

In an embodiment, the polypeptide comprises a mutation in one or more (e.g., 2, 3, 4, 5, 6, or all) of residues chosen from T256, T307, N286, A287, P257, Q311, or P247. In an embodiment, the polypeptide comprises mutations in residues T256, T307, N286, and A287. In an embodiment, the polypeptide comprises mutations in residues T256, T307, and P257. In an embodiment, the polypeptide comprises mutations in residues T256, T307, and Q311. In an embodiment, the polypeptide comprises mutations in residues T256, T307, and P247. In an embodiment, mutation in residue T256 is T256D. In an embodiment, the mutation in residue T307 is T307R. In an embodiment, the mutation in residue N286 is N286I. In an embodiment, the mutation in residue A287 is A287S. In an embodiment, the mutation in residue P257 is P257L. In an embodiment, the mutation in residue Q311 is Q311V or Q311L. In an embodiment, the mutation in residue P247 is P247D. In an embodiment, the polypeptide comprises mutations T256D, T307R, N286D, and A287S. In an embodiment, the polypeptide comprises mutations T256D, T307R, and P257L. In an embodiment, the polypeptide comprises mutations T256D, T307R, and Q311V or Q311L. In an embodiment, the polypeptide comprises mutations T256D, T307R, and P247D.

In an embodiment, the polypeptide comprises a mutation in one or more (e.g., 2, 3, 4, 5, 6, 7, or all) of residues chosen from N286, A287, P247, Q311, V308, P257, N315, or V279. In an embodiment, the polypeptide comprises mutations in residues N286, A287, P247, and Q311. In an embodiment, the mutation in residue N286 is N286D. In an embodiment, the mutation in residue A287 is A287S. In an embodiment, the mutation in residue P247 is P247D. In an embodiment, the mutation in residue Q311 is Q311V. In an embodiment, the polypeptide comprises mutations in residues V308 and P257. In an embodiment, the mutation in residue V308 is V308N. In an embodiment, the mutation in residue P257 is P257M. In an embodiment, the polypeptide comprises mutations in residues Q311, N315, and V279. In an embodiment, the mutation in residue Q311 is Q311L. In an embodiment, the mutation in residue N315 is N315T. In an embodiment, the mutation in residue V279 is V279I.

In an embodiment, the polypeptide comprises a mutation in one or more (e.g., 2, 3, or all) of residues chosen from G433 or H433, P434 or G434, G434a, or H435. In an embodiment, the polypeptide comprises mutations in residues G433, P434, and H435. In an embodiment, the polypeptide comprises mutations in residues G433, P434, G434a, and H435. In an embodiment, the polypeptide comprises mutations in residues H433, G434, P434a, and H435.

In an embodiment, the polypeptide comprises one or more (e.g., 2, 3, 4, 5, 6, 7, 8, 9, 10, or more) mutations, or one or more combination of mutations, as described in Table 1. For example, a combination of mutations can include one or more mutations listed under the name FcMutX and one or more mutations listed under the name FcMutY, where X and Y are three-digit numbers shown in Table 1, and X is not equal to Y.

In an embodiment, the polypeptide comprises mutation I253M. In an embodiment, the polypeptide comprises mutations L309H, D312A and N315D. In an embodiment, the polypeptide comprises mutation L309N. In an embodiment, the polypeptide comprises mutations M252E and S254R. In an embodiment, the polypeptide comprises mutations M252E, S254R and R255Y. In an embodiment, the polypeptide comprises mutation S254H. In an embodiment, the polypeptide comprises mutation S254M. In an embodiment, the polypeptide comprises mutations T256D and T307R. In an embodiment, the polypeptide comprises mutations T256L, N286I and T307I. In an embodiment, the polypeptide comprises mutations T256I, N286I and T307I. In an embodiment, the polypeptide comprises mutations K248S and D376Q. In an embodiment, the polypeptide comprises mutations K248S and D376N. In an embodiment, the polypeptide comprises mutations D376Q and E380A. In an embodiment, the polypeptide comprises mutations D376N and E380A. In an embodiment, the polypeptide comprises mutations D376Q and M428L. In an embodiment, the polypeptide comprises mutations K248S and A378I. In an embodiment, the polypeptide comprises mutation L314K. In an embodiment, the polypeptide comprises mutation M252W. In an embodiment, the polypeptide comprises mutation V308F. In an embodiment, the polypeptide comprises mutations V308F and N434Y. In an embodiment, the polypeptide comprises mutations T256D, T307R and D376N. In an embodiment, the polypeptide comprises mutations L309R and D312E. In an embodiment, the polypeptide comprises mutations L309R, Q311P and D312E. In an embodiment, the polypeptide comprises mutations K246N and P247A. In an embodiment, the polypeptide comprises mutations K246N, P247A and D376N. In an embodiment, the polypeptide comprises mutations T256E and T307R. In an embodiment, the polypeptide comprises mutations T256R and T307D. In an embodiment, the polypeptide comprises mutations T256R and T307E. In an embodiment, the polypeptide comprises mutation Q311P. In an embodiment, the polypeptide comprises mutation D376Q. In an embodiment, the polypeptide comprises mutations T256D, N286D, A287S and T307R. In an embodiment, the polypeptide comprises mutations T256D, P257L and T307R. In an embodiment, the polypeptide comprises mutations T256D, T307R and Q311V. In an embodiment, the polypeptide comprises mutations P247D, T256D and T307R. In an embodiment, the polypeptide comprises mutations P247D, N286D, A287S and Q311V. In an embodiment, the polypeptide comprises mutations P257M and V308N. In an embodiment, the polypeptide comprises mutations V279I, Q311L and N315T. In an embodiment, the polypeptide comprises mutations H433G and N434P. In an embodiment, the polypeptide comprises mutations T256D, N286D and T307R. In an embodiment, the polypeptide comprises mutations T256D, N286E and T307R. In an embodiment, the polypeptide comprises mutations T256D, N286Q and T307R. In an embodiment, the polypeptide comprises mutations T256D, P257T and T307R. In an embodiment, the polypeptide comprises mutations T256D, P257V and T307R. In an embodiment, the polypeptide comprises mutations T256D, T307R and Q311I. In an embodiment, the polypeptide comprises mutations T256D, T307R and Q311L. In an embodiment, the polypeptide comprises mutations T256D, T307R and Q311M. In an embodiment, the polypeptide comprises mutations T256D, P257L, N286D, T307R and Q311V. In an embodiment, the polypeptide comprises mutations T256D, T307R and M428L In an embodiment, the mutation is other than M252Y, S254T, T256E, L309N, T250Q, M428L, N434S, N434A, T307A, E380A, N434A, M252Y, S254T, T256E, or a combination thereof. In an embodiment, the mutation is in a residue other than residue M252, S254, T256, L309, T250, M428, N434, N434, T307, E380, N434, M252, S254, T256, or a combination thereof. In an embodiment, the polypeptide does not have one or more (e.g., 2, 3, 4, 5, 6, 7, 8, 9, or all) of the following mutation or mutations: (i) M252Y, S254T, and T256E; (ii) L309N; (iii) T250Q and M428L; (iv) M428L and N434A; (v) N434A; (vi) T307A, E380A, and N434A; (vii) M252W; (viii) V308F; (ix) V308F and N434Y; or (x) H435A.

In an embodiment, the polypeptide comprises a first mutation chosen from M252Y, S254T, T256E, L309N, T250Q, M428L, N434S, N434A, T307A, E380A, N434A, M252Y, S254T, or T256E, and a second mutation chosen from a mutation in Table 1 other than M252Y, S254T, T256E, L309N, T250Q, M428L, N434S, N434A, T307A, E380A, N434A, M252Y, S254T, and T256E.

In an embodiment, the polypeptide comprises a combination of mutations chosen from M252Y, S254T, T256E, L309N, T250Q, M428L, N434S, N434A, T307A, E380A, N434A, M252Y, S254T, or T256E, wherein the combination is other than (i) M252Y, S254T, and T256E; (ii) L309N; (iii) T250Q and M428L; (iv) M428L and N434A; (v) N434A; (vi) T307A, E380A, and N434A; (vii) M252W; (viii) V308F; (ix) V308F and N434Y; or (x) H435A.

In an embodiment, the polypeptide further comprises a mutation in the Fc region that increases an effector function. In an embodiment, the mutation is in a residue chosen from S239 (e.g., S239D), A330 (e.g., A330L), I332 (e.g., I332E), F243 (e.g., F243L), G236 (e.g., G236A), or a combination thereof, e.g., to increase an effector function.

In an embodiment, the polypeptide further comprises a mutation in the Fc region that decreases an effector function. In an embodiment, the mutation is in a residue chosen from K322 (e.g., K322A), L234 (e.g., L234A or L234F), L235 (e.g., L235A or L235E), P331 (e.g., P331S), N297, or a combination thereof, e.g., to decrease an effector function.

In an embodiment, the polypeptide further comprises a mutation in a region other than the Fc region, e.g., in a Fab region.

In an embodiment, the polypeptide further comprises a plurality of mutations, wherein at least one mutation is a compensating mutation, e.g., a compensating mutation described herein.

In an embodiment, the polypeptide is an isolated polypeptide. In an embodiment, the polypeptide is a synthetic polypeptide.

In an aspect, the disclosure features a composition, e.g., pharmaceutical composition, comprising a polypeptide described herein. In an embodiment, the composition further comprises a pharmaceutical acceptable carrier.

In an aspect, the disclosure features a nucleic acid molecule encoding a polypeptide described herein. In an aspect, the disclosure features a vector comprising a nucleic acid molecule described herein. In an aspect, the disclosure features a cell, e.g., an isolated cell, comprising a nucleic acid molecule described herein or a vector described herein. In an aspect, the disclosure features a kit comprising a polypeptide described herein and instructions to use of the polypeptide. In an aspect, the disclosure features a container comprising a polypeptide described herein.

In an aspect, the disclosure features a method of producing a polypeptide described herein, the method comprising culturing a cell described herein under conditions that allow production of an antibody molecule, thereby producing the polypeptide. In an embodiment, the method further comprises isolating or purifying the polypeptide.

In an aspect, the disclosure features a method of treating a disorder (e.g., a disorder described herein), the method comprising administering to a subject in need thereof an effective amount of a polypeptide described herein or a composition described herein, thereby treating the disorder.

In an aspect, the disclosure features a polypeptide described herein for use in a method of treating a disorder (e.g., a disorder described herein). In another aspect, the disclosure features use of a polypeptide described herein in the manufacture of a medicament in the treatment of a disorder (e.g., a disorder described herein).

In an aspect, the disclosure features a method of detecting a molecule, the method comprising contacting a cell or a sample from a subject with polypeptide described herein, thereby detecting the molecule.

The disclosure contemplates all combinations of any one or more of the foregoing aspects and/or embodiments, as well as combinations with any one or more of the embodiments set forth in the detailed description and examples.

Other features, objects, and advantages of the compositions and methods herein will be apparent from the description and drawings, and from the claims.

BRIEF DESCRIPTION OF THE DRAWINGS

FIG. 12 depicts biophysical properties of Fc engineered variants.

FIG. 17A depicts the binding of exemplary Fc variants to FcγRI, FcγRIIA, FcγRIIB, FcγRIIIA, and C1q.

FIG. 17B depicts the binding of FcMut213 to FcγRIIIA compared to wild-type.

FIG. 18 depicts the CDC activity of exemplary Fc variants (Rituximab Fab). Calculation is based on concentration that achieves 50% lysis, not the mid-point of the four-parameter fit.

FIG. 26 depicts binding of motavizumab Fab with Fc variants to TRIM21.

DETAILED DESCRIPTION

Figure 1:
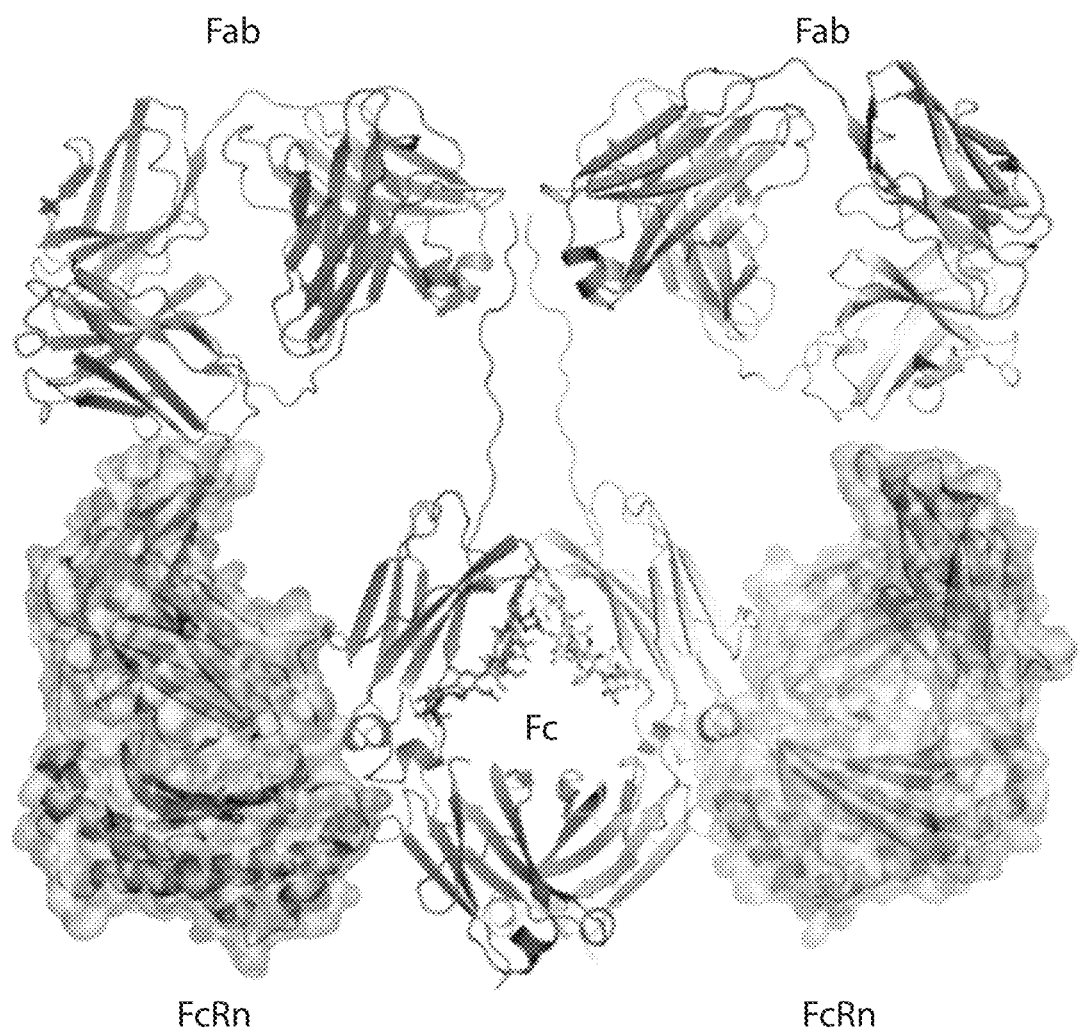
FIG. 1 depicts the binding between FcRn and IgG1.

Disclosed herein are polypeptides (e.g., antibody molecules or fusion proteins) that bind to a target molecule or cell, e.g., a human protein or cell, with high affinity and specificity. Advantageously, several of the polypeptides (e.g., antibody molecules or fusion proteins) describe herein have one or more improved or desired pharmacokinetic properties, such as circulating half-life. Without wishing to be bound theory, it is believed that polypeptides can have a range of circulating half-lives in humans, and circulating half-life can affect, e.g., interaction with serum and cell components, rate of fluid phase pinocytosis, interaction with FcRn, receptor mediated endocytosis, drug doses, and generation of anti-drug antibodies. Nucleic acid molecules encoding the polypeptides (e.g., antibody molecules or fusion proteins), expression vectors, host cells, compositions (e.g., pharmaceutical compositions), kits, containers, and methods for making the polypeptides (e.g., antibody molecules or fusion proteins), are also provided. The polypeptides (e.g., antibody molecules or fusion proteins) and pharmaceutical compositions disclosed herein can be used (alone or in combination with other agents or therapeutic modalities) to treat, prevent, and/or diagnose disorders and conditions, e.g., disorders and conditions associated with a target molecule (e.g., protein) or cell, e.g., a disorder or condition described herein.

Without wishing to be bound by theory, it is believed that in some embodiments, the long circulating half-life of IgGs is attributed to its ability to minimize its endosomal degradation by associating with the neonatal Fc receptor (FcRn). FcRn plays an important role in placental transfer of IgG molecules from mother to fetus and in serum IgG homeostasis (Leach et al., *J Immunol*, 1996. 157(8): 3317-22; Simister et al., *Eur J Immunol*, 1996. 26(7): 1527-31; Kristoffersen, *APMIS Suppl*, 1996. 64: 5-36; Roopenian et al., *J Immunol*, 2003. 170(7): 3528-33; Junghans and Anderson, *Proc Natl Acad Sci USA*, 1996. 93(11): 5512-6). The acidic environment of the early endosome can allow for binding of IgG and albumin to FcRn, which protects the IgG from undergoing degradation and helps trafficking the IgG back to the extracellular environment, where, upon exposure to physiological pH, the molecules are released back into circulation. This pathway can be largely responsible for the prolonged serum half-life of both IgG and albumin (Junghans and Anderson, *Proc Natl Acad Sci USA*, 1996. 93(11): 5512-6; Chaudhury et al., *J Exp Med*, 2003. 197(3): 315-22).

The Fc domain of an antibody is primarily responsible for binding to FcRn to facilitate antibody recycling. In some embodiments, antibodies with identical Fc regions can have different circulating half-lives, at least in part, because a number of factors such as thermal stability, interaction with serum and cell components, presence of anti-drug antibodies, high dose, receptor mediated endocytosis, and fluid phase pinocytosis, can promote antibody degradation and negatively influence its half-life. The interaction of IgG with FcRn can serve to protect the antibody from endosomal degradation and extend the half-life of the antibody. Modification of Fc can be used to promote FcRn interaction and therefore extend the half-life of antibodies (Ghetie et al., *Nat Biotechnol*, 1997. 15(7): p. 637-40; Dall'Acqua et al., *J Biol Chem*, 2006. 281(33): 23514-24; Hinton et al., *J Biol Chem*, 2004. 279(8): 6213-6; Vaccaro et al., *Nat Biotechnol*, 2005. 23(10): 1283-8; Zalevsky et al., *Nat Biotechnol*, 2010. 28(2): 157-9; Dall'Acqua et al., *J Immunol*, 2002. 169(9): 5171-80; Monnet et al., *MAbs*, 2014. 6(2): 422-36; Monnet et al., *Front Immunol*, 2015. 6: 39; Shields et al., *J Biol Chem*, 2001. 276(9): 6591-604; Robbie et al., *Antimicrob Agents Chemother*, 2013. 57(12): 6147-53).

The Fc of IgG can also bind to various other receptors such as FcγRI, FcγRIIa, FcγRIIb, FcγRIII, C1q, and TRIM21, and these interactions mediate various effector functions such as antibody dependent cellular cytotoxicity (ADCC), complement dependent cytotoxicity (CDC), antibody dependent cellular phagocytosis (ADCP), and antibody dependent intracellular neutralization (ADIN). Traditional approaches used to identify the Fc variants have largely relied on random mutagenesis and display formats and often compromise certain important attributes of the antibody, be it effector functions or biophysical stability.

Without wishing to be bound by theory, it is believed that in some embodiment, the engineering of Fc for FcRn binding or half-life extension as disclosed herein is performed in the context of the various effector functions mediated by Fc. For example, a structural and network based framework can be used to interrogate the interaction of Fc with FcRn at neutral and acidic pH. Using this framework, different pathways for improving FcRn binding, e.g., decreasing the $k_{off}$ of interaction, can be identified. The interaction networks of mutations can be mapped and mutations can be combined and assessed for binding to FcRn and other Fc receptors. For example, Fc variants that confer enhancement in half-life and retain and in some cases enhance effector functions such as ADCC and CDC can be identified. With the increasing use of antibodies and fusion proteins as therapeutics for prevention and treatment of different diseases, there have been greater needs to develop antibodies and fusion proteins with long half-life, e.g., to treat or prevent chronic diseases.

Definitions

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The compositions and methods disclosed herein encompass polypeptides and nucleic acids having the sequences specified, or sequences substantially identical or similar thereto, e.g., sequences at least 85%, 90%, 95% identical or higher to the sequence specified.

In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a typical embodiment, the length of a reference sequence aligned for comparison purposes is at least 30%, e.g., at least 40%, 50%, 60%, e.g., at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch ((1970) *J. Mol. Biol.* 48:444-453) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In certain embodiments, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. One suitable set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to a nucleic acid as described herein. BLAST protein searches can be performed with the XBLAST program, score=50, wordlength=3 to obtain amino acid sequences homologous to protein molecules described herein. To obtain gapped alignments for comparison purposes, Gapped BLAST can be utilized as described in Altschul et al., (1997) *Nucleic Acids Res.* 25:3389-3402. When utilizing BLAST and gapped BLAST programs, the default parameters of the respective programs (e.g., XBLAST and NBLAST) can be used. See www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions 4) are suitable conditions and the ones that should be used unless otherwise specified.

It is understood that the molecules described herein may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide," "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures. In an embodiment, the polypeptide is an antibody molecule. In another embodiment, the polypeptide is a fusion protein.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

As used herein, the term "treat," e.g., a disorder described herein, means that a subject (e.g., a human) who has a disorder, e.g., a disorder described herein, and/or experiences a symptom of a disorder, e.g., a disorder described herein, will, in an embodiment, suffer less a severe symptom and/or recover faster when an antibody molecule is administered than if the antibody molecule were never administered. Treatment can, e.g., partially or completely, alleviate, ameliorate, relieve, inhibit, or reduce the severity of, and/or reduce incidence, and optionally, delay onset of, one or more manifestations of the effects or symptoms, features, and/or causes of the disorder. In an embodiment, treatment is of a subject who does not exhibit certain signs of the disorder, and/or of a subject who exhibits only early signs of the disorder. In an embodiment, treatment is of a subject who exhibits one or more established signs of a disorder. In an embodiment, treatment is of a subject diagnosed as suffering from a disorder.

As used herein, the term "prevent," a disorder, means that a subject (e.g., a human) is less likely to have the disorder, if the subject receives a polypeptide (e.g., antibody molecule).

Various aspects of the compositions and methods herein are described in further detail below. Additional definitions are set out throughout the specification.

Antibody Molecules

Disclosed herein are antibody molecules, e.g., antibody molecules comprising an Fc region, e.g. an Fc region having one or more mutations described herein, and/or having one or more structural or functional properties described herein.

In an embodiment, the antibody molecule is engineered or derived from an antibody molecule (e.g., a parental antibody molecule) that contains an Fc region. For example, the engineered antibody molecule, or antibody molecule derivative, can have a different Fc region than the parental antibody molecule. In another embodiment, the antibody molecule is engineered or derived from an antibody molecule (e.g., a parental antibody molecule) that does not contain an Fc region. For example, the engineered antibody molecule, or antibody molecule derivative, can have an Fc region, directly or indirectly, fused to the parental antibody molecule or a functional fragment thereof.

As used herein, the term "antibody molecule" refers to a protein, e.g., an immunoglobulin chain or a fragment thereof, comprising at least one immunoglobulin variable domain sequence. The term "antibody molecule" includes, for example, full-length, mature antibodies and antigen-binding fragments of an antibody. For example, an antibody molecule can include a heavy (H) chain variable domain sequence (abbreviated herein as VH), and a light (L) chain variable domain sequence (abbreviated herein as VL). In another example, an antibody molecule includes two heavy (H) chain variable domain sequences and two light (L) chain variable domain sequence, thereby forming two antigen binding sites, such as Fab, Fab', F(ab')2, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The antibody molecules can be monoclonal or polyclonal. The antibody molecule can also be a human, humanized, CDR-grafted, or in vitro generated antibody. The antibody molecule can have a heavy chain constant region chosen from, e.g., IgG1, IgG2, IgG3, or IgG4. The antibody molecule can also have a light chain chosen from, e.g., kappa or lambda. The term "immunoglobulin" (Ig) is used interchangeably with the term "antibody" herein.

Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments may be obtained using any suitable method, including several conventional techniques known to those with skill in the art, and the fragments can be screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

The antibody molecule can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

The antibody molecules disclosed herein can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to some aspects, a single domain antibody is a naturally occurring single domain antibody known as heavy chain antibody devoid of light chains. Such single domain antibodies are disclosed in WO 94/04678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are also contemplated.

The VH and VL regions can be subdivided into regions of hypervariability, termed "complementarity determining regions" (CDR), interspersed with regions that are more conserved, termed "framework regions" (FR or FW). The terms "complementarity determining region," and "CDR," as used herein refer to the sequences of amino acids within antibody variable regions which confer antigen specificity and binding affinity. As used herein, the terms "framework," "FW" and "FR" are used interchangeably.

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). In an embodiment, the following definitions are used: AbM definition of CDR1 of the heavy chain variable domain and Kabat definitions for the other CDRs. In an embodiment, Kabat definitions are used for all CDRs. In addition, embodiments described with respect to Kabat or AbM CDRs may also be implemented using Chothia hypervariable loops. Each VH and VL typically includes three CDRs and four FRs, arranged from amino-terminus to carboxy-terminus in the following order: FR1, CDR1, FR2, CDR2, FR3, CDR3, and FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding region" refers to the part of an antibody molecule that comprises determinants that form an interface that binds to an antigen, or an epitope thereof. With respect to proteins (or protein mimetics), the antigen-binding region typically includes one or more loops (of at least, e.g., four amino acids or amino acid mimics) that form an interface that binds to the antigen. Typically, the antigen-binding region of an antibody molecule includes at least one or two CDRs and/or hypervariable loops, or more typically at least three, four, five or six CDRs and/or hypervariable loops.

The terms "compete" or "cross-compete" are used interchangeably herein to refer to the ability of an antibody molecule to interfere with binding of another antibody molecule, to a target. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a FACS assay, an ELISA or BIACORE assay. In an embodiment, a competition binding assay is a quantitative competition assay. In an embodiment, a first antibody molecule is said to compete for binding to the target with a second antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.* 32:180-190 (1990)) and also because of potential allergic reactions (see, e.g., LoBuglio et al., *Hybridoma*, 5:5117-5123 (1986)).

The antibody molecule can be a polyclonal or a monoclonal antibody. In some embodiments, the antibody can be recombinantly produced, e.g., produced by any suitable phage display or combinatorial methods.

Various phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In an embodiment, the antibody molecule is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. In an embodiment, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see e.g., Wood et al. International Application WO 91/00906, Kucherlapati et al. PCT publication WO 91/10741; Lonberg et al. International Application WO 92/03918; Kay et al. International Application 92/03917; Lonberg et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by any suitable recombinant DNA technique. Several are known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immunoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to lipopolysaccharide. In an embodiment, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In some embodiments, the donor immunoglobulin is a non-human (e.g., rodent). The acceptor framework is typically a naturally-occurring (e.g., a human) framework or a consensus framework, or a sequence about 85% or higher, e.g., 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by any suitable method, and several such methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare humanized antibodies (UK Patent Application GB 2188638A, filed on Mar. 26, 1987; Winter U.S. Pat. No. 5,225,539), the contents of which is expressly incorporated by reference.

Also provided are humanized antibodies in which specific amino acids have been substituted, deleted or added. Criteria for selecting amino acids from the donor are described in, e.g., U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In an embodiment, the antibody molecule has a heavy chain constant region chosen from, e.g., the heavy chain constant regions of IgG1, IgG2 (e.g., IgG2a), IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody molecule (e.g., to increase or decrease one or more of: Fc receptor binding, antibody glycosylation, the number of cysteine residues, effector cell function, and/or complement function). In an embodiment, the antibody molecule has effector function and can fix complement. In another embodiment, the antibody molecule does not recruit effector cells or fix complement. In certain embodiments, the antibody molecule has reduced or no ability to bind an Fc receptor. For example, it may be an isotype or subtype, fragment or other mutant, which does not support binding to an Fc receptor, e.g., it has a mutagenized or deleted Fc receptor binding region.

In an embodiment, a constant region of the antibody molecule is altered. Methods for altering an antibody constant region are known in the art. Antibody molecules s with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference) Amino acid mutations which stabilize antibody structure, such as S228P (EU nomenclature, S241P in Kabat nomenclature) in human IgG4 are also contemplated. Similar type of alterations could be described which if applied to the murine, or other species immunoglobulin would reduce or eliminate these functions.

In an embodiment, the only amino acids in the antibody molecule are canonical amino acids. In an embodiment, the antibody molecule comprises naturally-occurring amino acids; analogs, derivatives and congeners thereof; amino acid analogs having variant side chains; and/or all stereoisomers of any of any of the foregoing. The antibody molecule may comprise the D- or L-optical isomers of amino acids and peptidomimetics.

A polypeptide of an antibody molecule described herein may be linear or branched, it may comprise modified amino acids, and it may be interrupted by non-amino acids. The antibody molecule may also be modified; for example, by disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The antibody molecule described herein can be used alone in unconjugated form, or can be bound to a substance, e.g., a toxin or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the antibody molecule can be coupled to a radioactive isotope such as an $\alpha$-, $\beta$-, or $\gamma$-emitter, or a $\beta$- and $\gamma$-emitter.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a toxin, a pharmaceutical agent, and/or a protein or peptide that can mediate association of the antibody or antibody portion with another molecule (such as a streptavidin core region or a polyhistidine tag).

Some types of derivatized antibody molecule are produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an anti-dengue antibody molecule may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-napthalenesulfonyl chloride, phycoerythrin and the like. An antibody may also be derivatized with detectable enzymes, such as alkaline phosphatase, horseradish peroxidase, $\beta$-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibody molecules can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An antibody molecule may be conjugated to another molecular entity, typically a label or a therapeutic (e.g., antimicrobial (e.g., antibacterial or bactericidal), immunomodulatory, immunostimularoty, cytotoxic, or cytostatic) agent or moiety. Radioactive isotopes can be used in diagnostic or therapeutic applications. Radioactive isotopes that can be coupled to the antibody molecules include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In), technetium ($^{99}$mTc), phosphorus ($^{32}$P), carbon ($^{14}$C), and tritium ($^{3}$H), or one or more of the therapeutic isotopes listed above.

The present disclosure provides radiolabeled antibody molecules and methods of labeling the same. In an embodiment, a method of labeling an antibody molecule is disclosed. The method includes contacting an antibody molecule, with a chelating agent, to thereby produce a conjugated antibody. The conjugated antibody is radiolabeled with a radioisotope, e.g. $^{111}$Indium, $^{90}$Yttrium and $^{177}$Lutetium, to thereby produce a labeled antibody molecule.

In some aspects, this disclosure provides a method of making an antibody molecule disclosed herein. The method includes: providing an antigen, or a fragment thereof; obtaining an antibody molecule that specifically binds to the antigen; evaluating efficacy of the antibody molecule in modulating activity of the antigen and/or organism expressing the antigen. The method can further include administering the antibody molecule, including a derivative thereof (e.g., a humanized antibody molecule) to a subject, e.g., a human.

This disclosure provides an isolated nucleic acid molecule encoding the above antibody molecule, vectors and host cells thereof. The nucleic acid molecule includes, but is not limited to, RNA, genomic DNA and cDNA.

Fusion Proteins

Disclosed herein are fusion proteins, e.g., fusion proteins comprising an Fc region, e.g. an Fc region having one or more mutations described herein, and/or having one or more structural or functional properties described herein.

In an embodiment, the fusion protein is engineered or derived from a polypeptide (e.g., a fusion protein) that contains an Fc region (e.g., a parental polypeptide). For example, the engineered polypeptide, or derivative, can have a different Fc region than the parental polypeptide. In another embodiment, the fusion protein is engineered or derived from a polypeptide that does not contain an Fc region (e.g., a parental polypeptide). For example, the engineered antibody molecule, or antibody molecule derivative, can have an Fc region, directly or indirectly, fused to the parental polypeptide.

As used herein, the term "fusion protein" refers to a protein, comprising two or more protein or peptide components. The two or more protein or peptide components can be obtained from different sources or encoded by different genes. A fusion protein is sometimes also referred to as a chimeric protein. An Fc-fusion protein (also known as Fc chimeric fusion protein, Fc-Ig, Ig-based chimeric fusion protein, or Fc-tag protein) can include an Fc region of an immunoglobulin (e.g., an Fc region described herein) linked (e.g., fused) to a protein or peptide. The Fc region can be linked (e.g., fused genetically) to the protein or peptide directly or indirectly, e.g., through a linker In an embodiment, the Fc region is derived from the Fc region of IgG, e.g., human IgG, e.g., IgG1, IgG2, IgG3, or IgG4. In an embodiment, the Fc region is derived from the Fc region of IgG1, e.g., human IgG1.

The Fc-fused binding partner can include a variety of proteins or peptides, or fragments thereof. For example, the Fc region can be fused to a peptide (e.g., a therapeutic peptide), a ligand (e.g., a ligand that activates upon binding with a cell surface receptor), a signaling molecule, the extracellular domain of a receptor, or a bait protein (e.g., used to identify a binding partner, e.g., in a protein microarray).

In an embodiment, the Fc fusion protein comprises an extracellular domain of a receptor or a soluble receptor, or a ligand binding portion thereof. In an embodiment, the receptor is a growth factor receptor. In an embodiment, the receptor is a cytokine receptor. In an embodiment, the receptor is an immune checkpoint molecule.

In an embodiment, the fusion protein comprises a vascular endothelia growth factor (VEGF)-binding portion from the extracellular domain of human VEGF receptors 1 and 2, fused to the Fc region of human IgG1. In an embodiment, the fusion protein is aflibercept. In an embodiment, the fusion protein (e.g., aflibercept) is used to treat a disorder described herein, e.g., an eye disorder (e.g., wet macular degeneration) or a cancer (e.g., a colorectal cancer).

In another embodiment, the fusion protein comprises a soluble tumor necrosis factor (TNF) receptor 2 fused to the Fc region of the human IgG1. In an embodiment, the fusion protein is etanercept. In an embodiment, the Fc fusion protein (e.g., etanercept) is used to treat a disorder described herein, e.g., an autoimmune disorder (e.g., rheumatoid arthritis).

In yet another embodiment, the fusion protein comprises ligand-binding domains of the extracellular portions of human interleukin-1 receptor 1 (IL-1R1) and IL-1 receptor accessory protein (IL-1RAcP) fused to the Fc region of human IgG1. In an embodiment, the fusion protein is rilonacept. In an embodiment, the fusion protein (e.g., rilonacept) is used to treat a disorder described herein, e.g., a cryopyrin-associated periodic syndrome (CAPS), e.g., familial cold autoinflammatory syndrome, Muckle-Wells syndrome, or a neonatal onset multisystem inflammatory disease.

In still another embodiment, the fusion protein comprises the extracellular domain of CTLA-4 fused to the Fc region of human IgG1. In an embodiment, the fusion protein is abatacept or belatacept. In an embodiment, the fusion protein (e.g., abatacept or belatacept) is used to treat a disorder described herein, e.g., an organ rejection, an autoimmune disorder (e.g., rheumatoid arthritis), or a cancer.

In an embodiment, the Fc fusion protein comprises a peptide, e.g., a therapeutic peptide. In an embodiment, the fusion protein comprises a thrombopoietin-binding peptide fused to the Fc region of human IgG1. In an embodiment, the fusion protein is romiplostim. In an embodiment, the fusion protein (e.g., romiplostim) is used to treat a disorder described herein, e.g., chronic idiopathic (immune) thrombocytopenic purpura (ITP).

In an embodiment, the fusion protein comprises the extracellular CD2-binding portion of the human leukocyte function antigen-3 (LFA-3) fused to the Fc region of human IgG1. In an embodiment, the fusion protein is alefacept. In an embodiment, the fusion protein (e.g., alefacept) is used to treat a disorder described herein, e.g., an autoimmune disorder (e.g., psoriasis) or a cancer (e.g., a cutaneous T-cell lymphoma or a T-cell non-Hodgkin lymphoma).

In an embodiment, the fusion protein comprises a coagulation factor.

In an embodiment, the fusion protein comprises Factor IX fused with the Fc region of IgG1. In another embodiment, the fusion protein comprises Factor VIII fused with the Fc region of IgG1. In an embodiment the fusion protein (e.g., the FIX-Fc fusion or FVIII-Fc fusion) is used to treat a disorder described herein, e.g., hemophilia A or hemophilia B.

In an embodiment, the fusion protein comprises one or more glycosylation sites, or is glycosylated. In another embodiment, the fusion protein does not have a glycosylation site, or is not glycosylated.

In an embodiment, the only amino acids in the fusion protein are canonical amino acids. In an embodiment, the fusion protein comprises naturally-occurring amino acids; analogs, derivatives and congeners thereof; amino acid analogs having variant side chains; and/or all stereoisomers of any of any of the foregoing. The fusion protein may comprise the D- or L-optical isomers of amino acids and peptidomimetics.

In an aspect, this disclosure provides a method of making a fusion protein disclosed herein. The fusion proteins described herein can be produced by any suitable recombinant DNA technique. In an embodiment, the method includes culturing a cell containing a nucleic acid encoding the fusion protein under conditions that allow production of the fusion protein. In another embodiment, the method further includes isolating or purifying the fusion protein. In yet another embodiment, the method further includes evaluating efficacy of the fusion protein in a cell-based assay or in an animal model. In still another embodiment, the method further includes administering the fusion protein to a subject, e.g., a human.

This disclosure provides an isolated nucleic acid molecule encoding the above fusion proteins, vectors and host cells thereof. The nucleic acid molecule includes, but is not limited to, RNA, genomic DNA and cDNA.

Fc Region

A fragment crystallizable region, or Fc region, refers to a region of an immunoglobulin that is capable of interacting with an Fc receptor. In an embodiment, the Fc region is also capable of interacting with a protein of the complement system. While without wishing to be bound by theory, it is believed that in an embodiment, the interaction between the Fc region with an Fc receptor, allows for activation of the immune system.

In IgG, IgA and IgD antibody isotypes, the naturally-occurring Fc region generally comprises two identical protein fragments, derived from the second and third constant domains of the antibody's two heavy chains. Naturally-occurring IgM and IgE Fc regions generally comprise three heavy chain constant domains ($C_H$ domains 2-4) in each polypeptide chain. The Fc regions of IgGs can contain a highly conserved N-glycosylation site (Stadlmann et al. (2008). *Proteomics* 8 (14): 2858-2871; Stadlmann (2009) *Proteomics* 9 (17): 4143-4153). While not wishing to be bound by theory, it is believed that in an embodiment, glycosylation of the Fc fragment contributes to Fc receptor-mediated activities (Peipp et al. (2008) *Blood* 112 (6): 2390-2399). In an embodiment, the N-glycans attached to this site are predominantly core-fucosylated diantennary structures of the complex type. In another embodiment, small amounts of these N-glycans also contain bisecting GlcNAc and/or α-2,6 linked sialic acid residues.

An exemplary Fc region amino acid sequence is shown below.

(SEQ ID NO: 1)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVL<u>H</u>QDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEAL<u>HNH</u>YTQKSLSLSPGK

In SEQ ID NO: 1, the first amino acid residue in this sequence is referred to as position 118 herein. The three Histidines in bold and underlined are positions 310, 433 and 435, respectively.

A polypeptide (e.g., an antibody molecule or fusion protein) described herein can have one or more (e.g., 2, 3, 4, 5, 6, 7, 8, 9, 10, 11, 12, 13, 14, 15, 16, 17, 18, 19, 20, 21, 22, 23, 24, 25, or more) of mutations or combinations of mutations described in Table 1.

TABLE 1

Exemplary Fc mutations

| Name | Mutation |
| --- | --- |
| FcMut001 | I253M |
| FcMut002 | L309H_D312A_N315D |
| FcMut003 | L309N |
| FcMut004 | M252E_S254R |
| FcMut005 | M252E_S254R_R255Y |
| FcMut006 | S254H |
| FcMut007 | S254M |
| FcMut008 | T256D_T307R |
| FcMut009 | T256L_N286I_T307I |
| FcMut010 | T256I_N286I_T307I |
| FcMut011 | K248S_D376Q |
| FcMut012 | K248S_D376N |
| FcMut013 | D376Q_E380A |
| FcMut014 | D376N_E380A |
| FcMut015 | D376Q_M428L |
| FcMut016 | K248S_A378I |
| FcMut017 | L314K |
| FcMut018 | T250Q_M428L |
| FcMut019 | M428L_N434A |
| FcMut020 | N434A |
| FcMut021 | T307A_E380A_N434A |
| FcMut022 | M252W |
| FcMut023 | V308F |
| FcMut024 | V308F_N434Y |
| FcMut026 | T256D_T307R_D376N |
| FcMut027 | L309R_D312E |
| FcMut028 | L309R_Q311P_D312E |
| FcMut029 | K246N_P247A |
| FcMut030 | K246N_P247A_D376N |
| FcMut031 | T256E_T307R |
| FcMut032 | T256R_T307D |
| FcMut033 | T256R_T307E |
| FcMut034 | Q311P |
| FcMut035 | D376Q |
| FcMut036 | L234A_L235A |
| FcMut037 | L235V_G236A |
| FcMut038 | L234P_L235P |
| FcMut039 | L235P |
| FcMut040 | P329G |
| FcMut041 | P329E |

TABLE 1-continued

Exemplary Fc mutations

| Name | Mutation |
|---|---|
| FcMut042 | E233K |
| FcMut043 | T256D_N286D_A287S_T307R |
| FcMut044 | T256D_P257L_T307R |
| FcMut045 | T256D_T307R_Q311V |
| FcMut046 | P247D_T256D_T307R |
| FcMut047 | P247D_N286D_A287S_Q311V |
| FcMut048 | P257M_V308N |
| FcMut049 | V279I_Q311L_N315T |
| FcMut050 | M428L_N434S |
| FcMut051 | N434S |
| FcMut052 | H433G_N434P |
| FcMut053 | V259I_V308F_M428L |
| FcMut067 | T256D_N286D_T307R |
| FcMut068 | T256D_N286E_T307R |
| FcMut069 | T256D_N286Q_T307R |
| FcMut070 | T256D_P257T_T307R |
| FcMut071 | T256D_P257V_T307R |
| FcMut072 | T256D_T307R_Q311I |
| FcMut073 | T256D_T307R_Q311L |
| FcMut074 | T256D_T307R_Q311M |
| FcMut075 | T256D_P257L_N286D_T307R_Q311V |
| FcMut076 | T256D_T307R_M428L |
| FcMut077 | M428L |
| FcMut078 | M252Y_S254T_T256Q |
| FcMut079 | M252Y_S254T_T256E_K288E |
| FcMut080 | T256K_K288E |
| FcMut081 | T256D_E258T |
| FcMut082 | E283Q_H285E |
| FcMut083 | R344D_D401R |
| FcMut084 | K248E_E380K |
| FcMut085 | K248E_E380R |
| FcMut086 | K246H |
| FcMut087 | K248H |
| FcMut088 | T250I |
| FcMut089 | T250V |
| FcMut090 | L251F |
| FcMut091 | L251M |
| FcMut093 | P257V |
| FcMut094 | N276D |
| FcMut095 | H285N |
| FcMut096 | H285D |
| FcMut097 | K288H |
| FcMut098 | K288Q |
| FcMut099 | K288E |
| FcMut100 | T307E |
| FcMut101 | T307Q |
| FcMut102 | V308P |
| FcMut103 | V308I |
| FcMut104 | V308L |
| FcMut105 | L309H |
| FcMut106 | L309M |
| FcMut107 | Q311H |
| FcMut108 | L314F |
| FcMut109 | Y319H |
| FcMut110 | I336T |
| FcMut111 | P343D |
| FcMut112 | P343V |
| FcMut113 | E345Q |
| FcMut114 | P346V |
| FcMut115 | P374T |
| FcMut116 | D376N |
| FcMut117 | A378S |
| FcMut118 | A431T |
| FcMut119 | A431P |
| FcMut120 | A431G |
| FcMut121 | L432V |
| FcMut122 | L432I |
| FcMut123 | L432Q |
| FcMut124 | N434T |
| FcMut125 | H435N |
| FcMut126 | Y436H |
| FcMut127 | K439Q |
| FcMut128 | T256D |
| FcMut129 | T307R |
| FcMut130 | A378T |
| FcMut131 | A378D |
| FcMut132 | A378H |
| FcMut133 | A378Y |
| FcMut134 | A378V |
| FcMut135 | D376R |
| FcMut136 | D376F |
| FcMut137 | D376W |
| FcMut138 | L314H |
| FcMut139 | L432E_T437Q |
| FcMut140 | D376Q_A378T |
| FcMut141 | D376Q_I377M_A378T |
| FcMut142 | P244Q_D376Q |
| FcMut143 | P247T_A378T |
| FcMut144 | P247N_A378T |
| FcMut145 | T256D_T307R_L309T |
| FcMut146 | A339T_S375E_F404Y |
| FcMut147 | L235V_G236A_T256D_T307R |
| FcMut148 | L235V_G236A_D376Q_M428L |
| FcMut149 | L314N |
| FcMut150 | N315D |
| FcMut151 | A378T |
| FcMut152 | T437Q |
| FcMut153 | L432E |
| FcMut154 | Y436R |
| FcMut155 | L314M |
| FcMut156 | L234A_L235A_T256D_T307R_Q311V |
| FcMut157 | L234A_L235A_T256D_P257V_T307R |
| FcMut158 | L234A_L235A_T256D_P257L_N286D_T307R_Q311V |
| FcMut159 | L235V_G236A_T256D_T307R_Q311V |
| FcMut160 | L235V_G236A_T256D_P257V_T307R |
| FcMut161 | L235V_G236A_T256D_P257L_N286D_T307R_Q311V |
| FcMut162 | S267T_A327N_A330M |
| FcMut163 | S267T_A327N |
| FcMut164 | L235V_G236A_S267T_A327N_A330M |
| FcMut165 | L235V_G236A_S267T_A327N |
| FcMut166 | M252Y_S254T |
| FcMut167 | T256E |
| FcMut168 | G236A_I332E |
| FcMut169 | S239D_I332E |
| FcMut170 | G236A_S239D_I332E |
| FcMut171 | T256D_N286D_T307R_Q311V |
| FcMut172 | T256D_E258T_T307R |
| FcMut173 | T256D_E258T_T307R_Q311V |
| FcMut174 | T256D_P257V_E258T_T307R |
| FcMut175 | T256D_P257L_E258T_N286D_T307R_Q311V |
| FcMut176 | T256D_E258T_N286D_T307R_Q311V |
| FcMut177 | A378V_M428L |
| FcMut178 | A378V_M428I |
| FcMut179 | A378V_M428V |
| FcMut180 | T256D_N286D |
| FcMut181 | T256D_A378T |
| FcMut182 | T256D_Q311V |
| FcMut183 | T256D_Q311V_A378V |
| FcMut184 | T256D_T307R_A378V |
| FcMut185 | T256D_N286D_A378V |
| FcMut186 | T256D_T307R_Q311V_A378V |
| FcMut187 | H285_A378V |
| FcMut188 | H285D_Q311V |
| FcMut189 | T256D_H285D |
| FcMut190 | T256D_H285D_Q311V |
| FcMut191 | T256D_H285D_T307R |
| FcMut192 | T256D_H285D_T307R_A378V |
| FcMut193 | H285D_L314M_A378V |
| FcMut194 | T256D_E258T_H285D_Q311H |
| FcMut195 | T256D_E258T_H285D |
| FcMut196 | H285D_N315D |
| FcMut197 | H285N_T307Q_N315D |
| FcMut198 | H285D_L432E_T437Q |
| FcMut199 | T256D_E258T_N315D |
| FcMut200 | P257V_H285N |
| FcMut201 | H285N_L432F |
| FcMut202 | H285N_L432F |
| FcMut203 | T256D_E258T_L314M |
| FcMut204 | T256D_E258T_T307Q |
| FcMut205 | T256D_E258T_A378V |
| FcMut206 | V308P_A378V |
| FcMut207 | P257V_A378T |

TABLE 1-continued

Exemplary Fc mutations

| Name | Mutation |
|---|---|
| FcMut208 | P257V_V308P_A378V |
| FcMut209 | N315D_A378T |
| FcMut210 | H285N_L314M |
| FcMut211 | L314M_L432E_T437Q |
| FcMut212 | T307Q_N315D |
| FcMut213 | H285D_T307Q_A378V |
| FcMut214 | L314M_N315D |
| FcMut215 | T307Q_Q311V_A378V |
| FcMut216 | H285D_Q311V_A378V |
| FcMut217 | Q311V_N315D_A378V |
| FcMut218 | T256D_E258T_Q311V |
| FcMut219 | T256D_N315D_A378V |
| FcMut220 | T256D_Q311V_N315D |
| FcMut221 | T256D_T307Q_A378V |
| FcMut222 | T256D_T307Q_Q311V |
| FcMut223 | T256D_H285D_A378V |
| FcMut224 | T256D_H285D_T307R_Q311V |
| FcMut225 | T256D_H285D_N286D_T307R |
| FcMut226 | T256D_H285D_N286D_T307R_Q311V |
| FcMut227 | T256D_H285D_N286D_T307R_A378V |
| FcMut228 | T256D_N286D_T307R_Q311V_A378V |
| FcMut229 | T256D_H285D_T307R_Q311V_A378V |
| FcMut230 | V308P_Q311V_A378V |
| FcMut231 | T256D_V308P_A378V |
| FcMut232 | T256D_V308P_Q311V |
| FcMut233 | T256D_E258T_V308P |
| FcMut234 | H285D_V308P_Q311V |
| FcMut242 | E258T |
| FcMut243 | N286D |
| FcMut244 | Q311V |
| YTE | M252Y_S254T_T256E |

In an embodiment, the Fc region comprises FcMut001. In an embodiment, the Fc region comprises FcMut002. In an embodiment, the Fc region comprises FcMut003. In an embodiment, the Fc region comprises FcMut004. In an embodiment, the Fc region comprises FcMut005. In an embodiment, the Fc region comprises FcMut006. In an embodiment, the Fc region comprises FcMut007. In an embodiment, the Fc region comprises FcMut008. In an embodiment, the Fc region comprises FcMut009. In an embodiment, the Fc region comprises FcMut010. In an embodiment, the Fc region comprises FcMut011. In an embodiment, the Fc region comprises FcMut012. In an embodiment, the Fc region comprises FcMut013. In an embodiment, the Fc region comprises FcMut014. In an embodiment, the Fc region comprises FcMut015. In an embodiment, the Fc region comprises FcMut016. In an embodiment, the Fc region comprises FcMut017. In an embodiment, the Fc region comprises FcMut018. In an embodiment, the Fc region comprises FcMut019. In an embodiment, the Fc region comprises FcMut020. In an embodiment, the Fc region comprises FcMut021. In an embodiment, the Fc region comprises FcMut022. In an embodiment, the Fc region comprises FcMut023. In an embodiment, the Fc region comprises FcMut024. In an embodiment, the Fc region comprises FcMut026. In an embodiment, the Fc region comprises FcMut027. In an embodiment, the Fc region comprises FcMut028. In an embodiment, the Fc region comprises FcMut029. In an embodiment, the Fc region comprises FcMut030. In an embodiment, the Fc region comprises FcMut031. In an embodiment, the Fc region comprises FcMut032. In an embodiment, the Fc region comprises FcMut033. In an embodiment, the Fc region comprises FcMut034. In an embodiment, the Fc region comprises FcMut035. In an embodiment, the Fc region comprises FcMut036. In an embodiment, the Fc region comprises FcMut037. In an embodiment, the Fc region comprises FcMut038. In an embodiment, the Fc region comprises FcMut039. In an embodiment, the Fc region comprises FcMut040. In an embodiment, the Fc region comprises FcMut041. In an embodiment, the Fc region comprises FcMut042. In an embodiment, the Fc region comprises FcMut043. In an embodiment, the Fc region comprises FcMut044. In an embodiment, the Fc region comprises FcMut045. In an embodiment, the Fc region comprises FcMut046. In an embodiment, the Fc region comprises FcMut047. In an embodiment, the Fc region comprises FcMut048. In an embodiment, the Fc region comprises FcMut049. In an embodiment, the Fc region comprises FcMut050. In an embodiment, the Fc region comprises FcMut051. In an embodiment, the Fc region comprises FcMut052. In an embodiment, the Fc region comprises FcMut053. In an embodiment, the Fc region comprises FcMut067. In an embodiment, the Fc region comprises FcMut068. In an embodiment, the Fc region comprises FcMut069. In an embodiment, the Fc region comprises FcMut070. In an embodiment, the Fc region comprises FcMut071. In an embodiment, the Fc region comprises FcMut072. In an embodiment, the Fc region comprises FcMut073. In an embodiment, the Fc region comprises FcMut074. In an embodiment, the Fc region comprises FcMut075. In an embodiment, the Fc region comprises FcMut076. In an embodiment, the Fc region comprises FcMut077. In an embodiment, the Fc region comprises FcMut078. In an embodiment, the Fc region comprises FcMut079. In an embodiment, the Fc region comprises FcMut080. In an embodiment, the Fc region comprises FcMut081. In an embodiment, the Fc region comprises FcMut082. In an embodiment, the Fc region comprises FcMut083. In an embodiment, the Fc region comprises FcMut084. In an embodiment, the Fc region comprises FcMut085. In an embodiment, the Fc region comprises FcMut086. In an embodiment, the Fc region comprises FcMut087. In an embodiment, the Fc region comprises FcMut088. In an embodiment, the Fc region comprises FcMut089. In an embodiment, the Fc region comprises FcMut090. In an embodiment, the Fc region comprises FcMut091. In an embodiment, the Fc region comprises FcMut093. In an embodiment, the Fc region comprises FcMut094. In an embodiment, the Fc region comprises FcMut095. In an embodiment, the Fc region comprises FcMut096. In an embodiment, the Fc region comprises FcMut097. In an embodiment, the Fc region comprises FcMut098. In an embodiment, the Fc region comprises FcMut099. In an embodiment, the Fc region comprises FcMut100. In an embodiment, the Fc region comprises FcMut101. In an embodiment, the Fc region comprises FcMut102. In an embodiment, the Fc region comprises FcMut103. In an embodiment, the Fc region comprises FcMut104. In an embodiment, the Fc region comprises FcMut105. In an embodiment, the Fc region comprises FcMut106. In an embodiment, the Fc region comprises FcMut107. In an embodiment, the Fc region comprises FcMut108. In an embodiment, the Fc region comprises FcMut109. In an embodiment, the Fc region comprises FcMut110. In an embodiment, the Fc region comprises FcMut111. In an embodiment, the Fc region comprises FcMut112. In an embodiment, the Fc region comprises FcMut113. In an embodiment, the Fc region comprises FcMut114. In an embodiment, the Fc region comprises FcMut115. In an embodiment, the Fc region comprises FcMut116. In an embodiment, the Fc region comprises FcMut117. In an embodiment, the Fc region comprises FcMut118. In an embodiment, the Fc region comprises FcMut119. In an embodiment, the Fc region comprises FcMut120. In an embodiment, the Fc region comprises FcMut121. In an embodiment, the Fc region comprises FcMut122. In an embodiment, the Fc region comprises FcMut123. In an embodiment, the Fc region comprises FcMut124. In an embodiment, the Fc region comprises FcMut125. In an embodiment, the Fc region comprises FcMut126. In an embodiment, the Fc region comprises FcMut127. In an embodiment, the Fc region comprises FcMut128. In an embodiment, the Fc region comprises FcMut129. In an embodiment, the Fc region comprises FcMut130. In an embodiment, the Fc region comprises FcMut131. In an embodiment, the Fc region comprises FcMut132. In an embodiment, the Fc region comprises FcMut133. In an embodiment, the Fc region comprises FcMut134. In an embodiment, the Fc region comprises FcMut135. In an embodiment, the Fc region comprises FcMut136. In an embodiment, the Fc region comprises FcMut137. In an embodiment, the Fc region comprises FcMut138. In an embodiment, the Fc region comprises FcMut139. In an embodiment, the Fc region comprises FcMut140. In an embodiment, the Fc region comprises FcMut141. In an embodiment, the Fc region comprises FcMut142. In an embodiment, the Fc region comprises FcMut143. In an embodiment, the Fc region comprises FcMut144. In an embodiment, the Fc region comprises FcMut145. In an embodiment, the Fc region comprises FcMut146. In an embodiment, the Fc region comprises FcMut147. In an embodiment, the Fc region comprises FcMut148. In an embodiment, the Fc region comprises FcMut149. In an embodiment, the Fc region comprises FcMut150. In an embodiment, the Fc region comprises FcMut151. In an embodiment, the Fc region comprises FcMut152. In an embodiment, the Fc region comprises FcMut153. In an embodiment, the Fc region comprises FcMut154. In an embodiment, the Fc region comprises FcMut155. In an embodiment, the Fc region comprises FcMut156. In an embodiment, the Fc region comprises FcMut157. In an embodiment, the Fc region comprises FcMut158. In an embodiment, the Fc region comprises FcMut159. In an embodiment, the Fc region comprises FcMut160. In an embodiment, the Fc region comprises FcMut161. In an embodiment, the Fc region comprises FcMut162. In an embodiment, the Fc region comprises FcMut163. In an embodiment, the Fc region comprises FcMut164. In an embodiment, the Fc region comprises FcMut165. In an embodiment, the Fc region comprises FcMut166. In an embodiment, the Fc region comprises FcMut167. In an embodiment, the Fc region comprises FcMut168. In an embodiment, the Fc region comprises FcMut169. In an embodiment, the Fc region comprises FcMut170. In an embodiment, the Fc region comprises FcMut171. In an embodiment, the Fc region comprises FcMut172. In an embodiment, the Fc region comprises FcMut173. In an embodiment, the Fc region comprises FcMut174. In an embodiment, the Fc region comprises FcMut175. In an embodiment, the Fc region comprises FcMut176. In an embodiment, the Fc region comprises FcMut177. In an embodiment, the Fc region comprises FcMut178. In an embodiment, the Fc region comprises FcMut179. In an embodiment, the Fc region comprises FcMut180. In an embodiment, the Fc region comprises FcMut181. In an embodiment, the Fc region comprises FcMut182. In an embodiment, the Fc region comprises FcMut183. In an embodiment, the Fc region comprises FcMut184. In an embodiment, the Fc region comprises FcMut185. In an embodiment, the Fc region comprises FcMut186. In an embodiment, the Fc region comprises FcMut187. In an embodiment, the Fc region comprises FcMut188. In an embodiment, the Fc region comprises FcMut189. In an embodiment, the Fc region comprises FcMut190. In an embodiment, the Fc region comprises FcMut191. In an embodiment, the Fc region comprises FcMut192. In an embodiment, the Fc region comprises FcMut193. In an embodiment, the Fc region comprises FcMut194. In an embodiment, the Fc region comprises FcMut195. In an embodiment, the Fc region comprises FcMut196. In an embodiment, the Fc region comprises FcMut197. In an embodiment, the Fc region comprises FcMut198. In an embodiment, the Fc region comprises FcMut199. In an embodiment, the Fc region comprises FcMut200. In an embodiment, the Fc region comprises FcMut201. In an embodiment, the Fc region comprises FcMut202. In an embodiment, the Fc region comprises FcMut203. In an embodiment, the Fc region comprises FcMut204. In an embodiment, the Fc region comprises FcMut205. In an embodiment, the Fc region comprises FcMut206. In an embodiment, the Fc region comprises FcMut207. In an embodiment, the Fc region comprises FcMut208. In an embodiment, the Fc region comprises FcMut209. In an embodiment, the Fc region comprises FcMut210. In an embodiment, the Fc region comprises FcMut211. In an embodiment, the Fc region comprises FcMut212. In an embodiment, the Fc region comprises FcMut213. In an embodiment, the Fc region comprises FcMut214. In an embodiment, the Fc region comprises FcMut215. In an embodiment, the Fc region comprises FcMut216. In an embodiment, the Fc region comprises FcMut217. In an embodiment, the Fc region comprises FcMut218. In an embodiment, the Fc region comprises FcMut219. In an embodiment, the Fc region comprises FcMut220. In an embodiment, the Fc region comprises FcMut221. In an embodiment, the Fc region comprises FcMut222. In an embodiment, the Fc region comprises FcMut223. In an embodiment, the Fc region comprises FcMut224. In an embodiment, the Fc region comprises FcMut225. In an embodiment, the Fc region comprises FcMut226. In an embodiment, the Fc region comprises FcMut227. In an embodiment, the Fc region comprises FcMut228. In an embodiment, the Fc region comprises FcMut229. In an embodiment, the Fc region comprises FcMut230. In an embodiment, the Fc region comprises FcMut231. In an embodiment, the Fc region comprises FcMut232. In an embodiment, the Fc region comprises FcMut233. In an embodiment, the Fc region comprises FcMut234. In an embodiment, the Fc region comprises FcMut242. In an embodiment, the Fc region comprises FcMut243. In an embodiment, the Fc region comprises FcMut244.

In an embodiment, the Fc region comprises one or more (e.g., 2, 3, 4, 5, 6, 7, 8, 9, or more) of mutations or combinations of mutations chosen from FcMut045, FcMut171, FcMut183, FcMut186, FcMut190, FcMut197, FcMut213, FcMut215, FcMut216, FcMut219, FcMut222, FcMut223, FcMut224, FcMut226, FcMut227, FcMut228, or FcMut229. In an embodiment, the Fc region comprises one or more (e.g., 2, 3, 4, 5, 6, or all) of mutations or combinations of mutations chosen from FcMut045, FcMut183, FcMut197, FcMut213, FcMut215, FcMut228, or FcMut156. In another embodiment, the Fc region comprises one or more (e.g., 2, 3, 4, 5, or all) of mutations or combinations of mutations chosen from FcMut183, FcMut197, FcMut213, FcMut215, FcMut228, or FcMut229.

In an embodiment, the Fc region does not comprise one or more (e.g., 2, 3, 4, or all) of mutations or combinations of mutations chosen from FcMut018, FcMut021, FcMut050, FcMut102, or YTE. In an embodiment, the Fc region comprises one or more (e.g., 2, 3, 4, or all) of mutations or combinations of mutations chosen from FcMut018, FcMut021, FcMut050, FcMut102, or YTE, and one or more other mutations or combinations of mutations described in Table 1.

T307R/Q311V and a mutation or a combination of mutations capable of disrupting an Fc effector function, e.g., L234A/L235A.

A reference Fc region amino acid sequence (including the numbering used herein) is provided below (e.g., for identification of the mutation positions described herein). The CH2 domain sequence is underlined; the hinge region sequence is in italics, and the CH3 domain sequence is in bold.

(SEQ ID NO: 1)
```
118  ASTKGPSVFPLAPSSKSTSGGTAALGCLVKDYFPEPVTVSWNSGALTSGVHTFPAVL

175  QSSGLYSLSSVVTVPSSSLGTQTYICNVNHKPSNTKVDKKVEPKSCDKTHTCPPCPA

232  PELLGGPSVFLFPPKPKDTLMISRTPEVTCVVVDVSHEDPEVKFNWYVDGVEVHN

287  AKTKPREEQYNSTYRVVSVLTVLHQDWLNGKEYKCKVSNKALPAPIEKTISKAKGQP

344  REPQVYTLPPSRDELTKNQVSLTCLVKGFYPSDIAVEWESNGQPENNYKTTPPVLDS

401  DGSFFLYSKLTVDKSRWQQGNVFSCSVMHEALHNHYTQKSLSLSPGK
```

In an embodiment, the Fc region comprises one or more (e.g., 2, 3, 4, 5, 6, 7, 8, 9, 10, 11, 12, 13, 14, 15, 16, 17, 18, 19, 20, or more) of mutations or combinations of mutations described in Table 1 that result in a synergistic effect (e.g., binding affinity or circulating half-life) as described herein.

In an embodiment, the Fc region comprises one or more (e.g., 2, 3, 4, 5, 6, or 7) mutations in residues chosen from T256, H285, N286, T307, Q311, N315, or A378. In an embodiment, the Fc region comprises one or more (e.g., 2, 3, 4, 5, 6, or 7) mutations chosen from T256D, H285N, N286D, T307Q, Q311V, N315D, or A378V.

In an embodiment, the Fc region comprises a half-life enhancing mutation, a mutation that is capable of disrupting an Fc effector function, or both. In an embodiment, the Fc region comprises one or more mutations or combinations of mutations described herein, e.g., chosen from M252W, V308F/N434Y, R255Y, P257L/N434Y, V308F, P257N/M252Y, G385N, P257N/V308Y, N434Y, M252Y/S254T/T256E ("YTE"), M428L/N434S ("LS"), or any combination thereof. Alternatively, or additionally, in an embodiment, the Fc region comprises (a) one or more (e.g., 2, 3, 4, 5, or all) combinations of mutations chosen from: T256D/Q311V/A378V, H285N/T307Q/N315D, H285D/T307Q/A378V, T307Q/Q311V/A378V, T256D/N286D/T307R/Q311V/A378V, or T256D/T307R/Q311V; (b) a mutation or a combination of mutations capable of disrupting an Fc effector function, e.g., L234A/L235A (also known as "LALA" mutation), or (c) both (a) and (b).

In an embodiment, the Fc region comprises mutations T256D/Q311V/A378V and a mutation or a combination of mutations capable of disrupting an Fc effector function, e.g., L234A/L235A. In an embodiment, the Fc region comprises mutations H285N/T307Q/N315D and a mutation or a combination of mutations capable of disrupting an Fc effector function, e.g., L234A/L235A. In an embodiment, the Fc region comprises mutations H285D/T307Q/A378V and a mutation or a combination of mutations capable of disrupting an Fc effector function, e.g., L234A/L235A. In an embodiment, the Fc region comprises mutations T307Q/Q311V/A378V and a mutation or a combination of mutations capable of disrupting an Fc effector function, e.g., L234A/L235A. In an embodiment, the Fc region comprises mutations T256D/N286D/T307R/Q311V/A378V and a mutation or a combination of mutations capable of disrupting an Fc effector function, e.g., L234A/L235A. In an embodiment, the Fc region comprises mutations T256D/

Any of the half-life extension mutations described herein can be used in combination with any Fc mutation capable of enhancing or disrupting an Fc effector function.

The Fc region can bind to various cell receptors (e.g., Fc receptors) and complement proteins. The Fc region can also mediate different physiological effects of antibody molecules, e.g., detection of opsonized particles; cell lysis; degranulation of mast cells, basophils, and eosinophils; and other processes.

There are several different types of Fc receptors (FcR), which can be classified based on the type of antibody that they recognize.

Fcγ receptors (FcγR) belong to the immunoglobulin superfamily, and are involved, e.g., in inducing phagocytosis of opsonized microbes. This family includes several members, FcγRI (CD64), FcγRIIA (CD32), FcγRIIB (CD32), FcγRIIIA (CD16a), FcγRIIIB (CD16b), which differ in their antibody affinities due to their different molecular structure. For instance, FcγRI can bind to IgG more strongly than FcγRII or FcγRIII does. FcγRI also has an extracellular portion comprising three immunoglobulin (Ig)-like domains, one more domain than FcγRII or FcγRIII has. This property allows FcγRI to bind a sole IgG molecule (or monomer), but Fcγ receptors generally need to bind multiple IgG molecules within an immune complex to be activated.

The Fcγ receptors differ in their affinity for IgG and the different IgG subclasses can have unique affinities for each of the Fcγ receptors. These interactions can be further tuned by the glycan (oligosaccharide) at certain position of IgG. For example, by creating steric hindrance, fucose containing CH2-84.4 glycans reduce IgG affinity for FcγRIIIA, whereas G0 glycans, which lack galactose and terminate instead with GlcNAc moieties, have increased affinity for FcγRIIIA (Maverakis et al. (2015) *Journal of Autoimmunity* 57 (6): 1-13)

The neonatal Fc receptor (FcRn) is expressed on multiple cell types and is similar in structure to MHC class I. This receptor also binds IgG and is involved in preservation of this antibody (Zhu et al. (2001). *Journal of Immunology* 166 (5): 3266-76.). FcRn is also involved in transferring IgG from a mother either via the placenta to her fetus or in milk to her suckling infant. This receptor may also play a role in the homeostasis of IgG serum levels.

FcαRI (or CD89) belongs to the FcαR subgroup. FcαRI is found on the surface of neutrophils, eosinophils, monocytes, macrophages (including Kupffer cells), and dendritic cells. It comprises two extracellular Ig-like domains, and is a member of both the immunoglobulin superfamily and the multi-chain immune recognition receptor (MIRR) family. It signals by associating with two FcRγ signaling chains.

Fc-alpha/mu receptor (Fcα/μR) is a type I transmembrane protein. It can bind IgA, although it has higher affinity for IgM (Shibuya and Honda (2006) *Springer Seminars in Immunopathology* 28 (4): 377-82). With one Ig-like domain in its extracellular portion, this Fc receptor is also a member of the immunoglobulin superfamily.

There are two known types of FcεR. The high-affinity receptor FcεRI is a member of the immunoglobulin superfamily (it has two Ig-like domains). FcεRI is found on epidermal Langerhans cells, eosinophils, mast cells and basophils. This receptor can play a role in controlling allergic responses. FcεRI is also expressed on antigen-presenting cells, and controls the production of immune mediators, e.g., cytokines that promote inflammation (von Bubnoff et al. (2003) *Clinical and Experimental Dermatology* 28 (2): 184-7). The low-affinity receptor FcεRII (CD23) is a C-type lectin. FcεRII has multiple functions as a membrane-bound or soluble receptor. It can also control B cell growth and differentiation and blocks IgE-binding of eosinophils, monocytes, and basophils (Kikutani et al. (1989) *Ciba Foundation Symposium* 147: 23-31).

In an embodiment, the Fc region can be engineered to contain an antigen-binding site to generate an Fcab fragment (Wozniak-Knopp et al. (2010) *Protein Eng Des* 23 (4): 289-297). Fcab fragments can be inserted into a full immunoglobulin by swapping the Fc region, thus obtaining a bispecific antibody (with both Fab and Fcab regions containing distinct binding sites).

The binding and recycling of FcRn can be illustrated below. For example, IgG and albumin are internalized into vascular endothelial cells through pinocytosis. The pH of the endosome is 6.0, facilitating association with membrane-bound FcRn. The contents of endosomes can be processed in one of two ways: either recycling back to the apical cell membrane or transcytosis from the apical to the basolateral side. IgG not associated with FcRn is degraded by lysosomes.

While not wishing to be bound by theory, it is believed that FcRn interaction with IgG is mediated through Fc. The binding of Fc to FcRn is pH specific, e.g., no significant binding at pH 7.4 and strong binding in acidic environment. Structure of FcRn in complex with Fc domain of IgG1 molecule is known in FIG. 1. Each FcRn molecule generally binds to an Fc-monomer. In an embodiment, Fab domains can also influence binding of IgG to FcRn, e.g., have either a negative or no influence on the affinity of the IgG for FcRn.

There can be multiple considerations when an Fc region is engineered to enhance half-life of a polypeptide. For example, prolonging half-life and efficient recirculation of antibody molecules or fusion proteins often requires pH specific affinity enhancement (e.g., only at low pH of the endosome). FcRn binds proximal to the linker region between CH2 and CH3 domains of a Fc region. Modifications to the linker can impact Fc engagement with Fcγ receptors. Modifications on the Fc region can impact thermal stability and aggregation properties of the polypeptide.

FcRn Binding Optimization: Reducing Impact on Other Effector Functions

In an embodiment, the polypeptide (e.g., antibody molecule or fusion protein) described herein has the same affinity function, or does not substantially alter (e.g., decrease by more than 10%, 20%, 30%, 40%, 50%, 60%, 70%, 80%, or 90%) an effector function (e.g., an effector function described herein). In an embodiment, the effector function is not associated with the binding between an Fc region and an FcRn.

Figure 2:
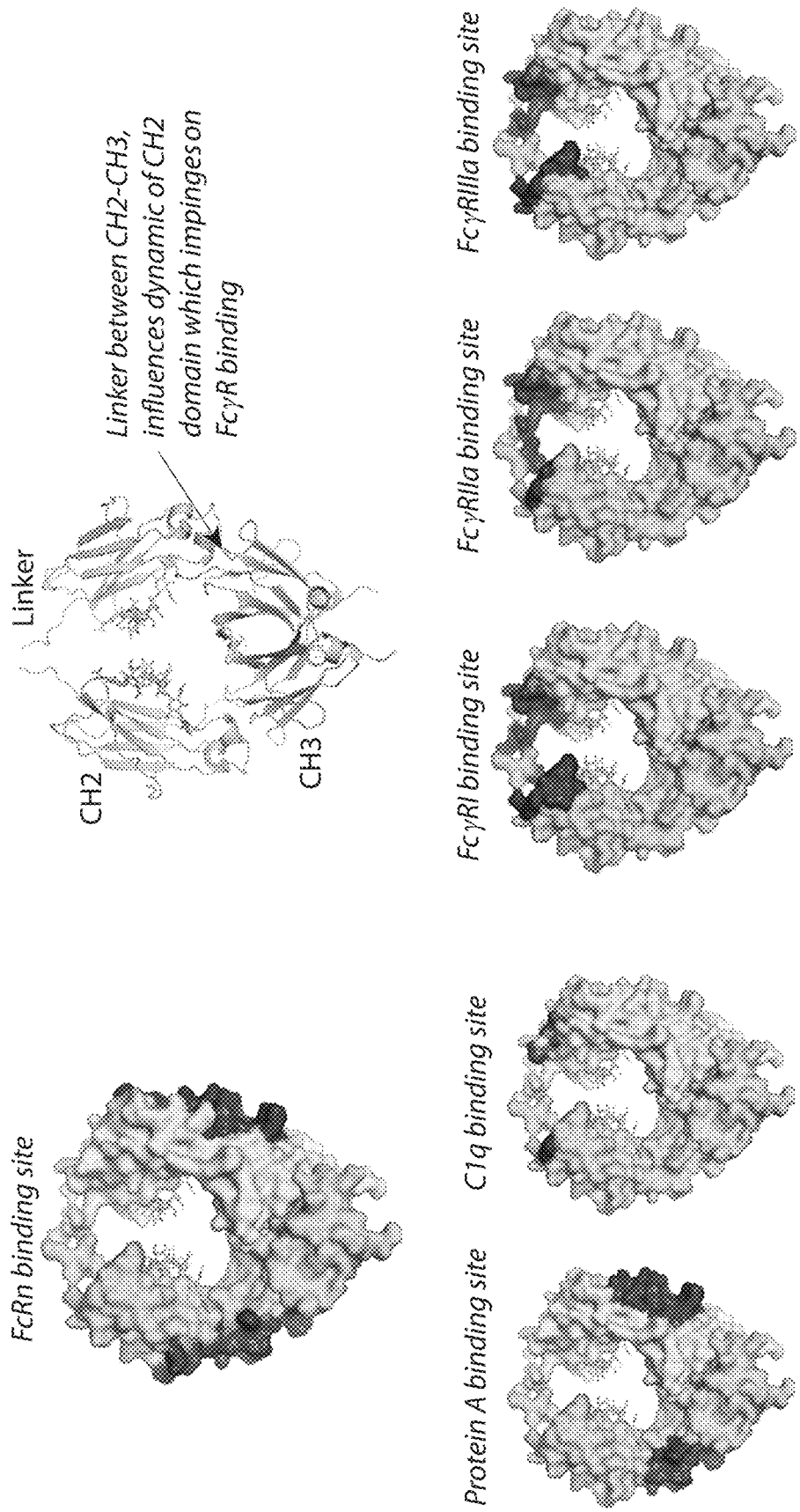
FIG. 2 depicts various binding sites in the Fc region.

The amino acid residues to be mutated can be selected, at least in part, based on the structural or functional properties of one or more binding sites on the Fc region. These binding sites include, but are not limited to, a Protein A binding site, a C1q binding site, an FcγRI binding site, an FcγRIIa binding site, an FcγRIIIa binding site, or an FcRn binding site, e.g., as shown in FIG. 2. The binding sites can also include a TRIM21 binding site, e.g., one or more residues chosen from loop 308-316, loop 252-256, or loop 429-436 of an IgG. In an embodiment, the linker region between the CH2 and CH3 domain can influence the dynamics of the CH2 domain which impinges on FcγR binding.

Structural Basis for pH Specific Engagement of FcRn

Without wishing to be bound by theory, it is believed that low pH of the endosome leads to protonation of surface histidines on the CH2 and CH3 domains. For example, protonation of residue H310 on CH2 and/or H433 on CH3 can be important for FcRn engagement, e.g., at low pH (e.g., at pH 6.0). Protonation can also lead to change in the conformational dynamics of the region, such as better exposure or shielding of the linker region for solvent or ligand molecule binding. Accordingly, in an embodiment, the polypeptide (e.g., antibody molecule or fusion protein) comprises a mutation in residue H310, a mutation in residue H433, or both. One or more residues adjacent to residues H310 and/or H433 can also be mutated. The polypeptide can also include a compensating or beneficial mutation, e.g., a mutation that compensates, or beneficial, for any of the aforesaid mutations, e.g., to reduce a negative consequence of that mutation (e.g., polar vs. non-polar, charged vs. no charge, positively-charged (basic) vs. negatively charged (acidic), or hydrophobic vs. hydrophilic). For example, P247D can be a compensating or beneficial mutation.

Figure 3:
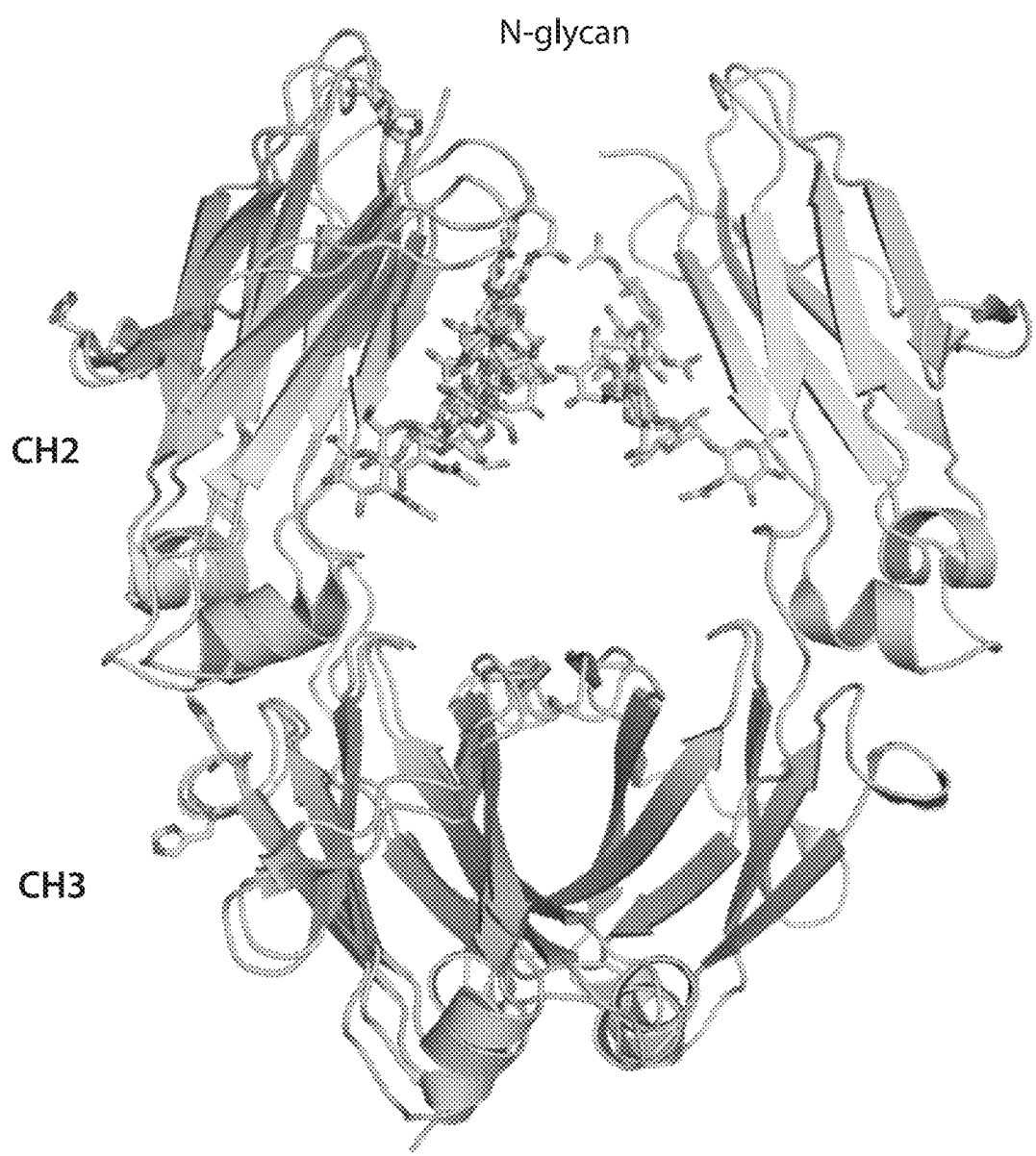
FIG. 3 depicts the structural basis for pH specific engagement of FcRn.

In an embodiment, protonation of histidine can result in additional conformational changes including, e.g., movement/displacement of the linker/CH2/CH3 interface residues. Crystal structures of Fc fragments have been crystallized at different pHs. As shown in FIG. 3, an analysis of two high resolution crystal structures of Fc fragments crystallized and pH 6.5 (cyan) and 5.0 (green) indicated potential differences.

Mapping of Fc-FcRn Interaction Interface

In an embodiment, the polypeptide (e.g., antibody molecule or fusion protein) described herein comprises a mutation that can alter the interaction between an Fc region and an FcRn. In an embodiment, the mutation is selected based, at least in part, on a structural feature of the Fc-FcRn interaction interface.

Figure 4:
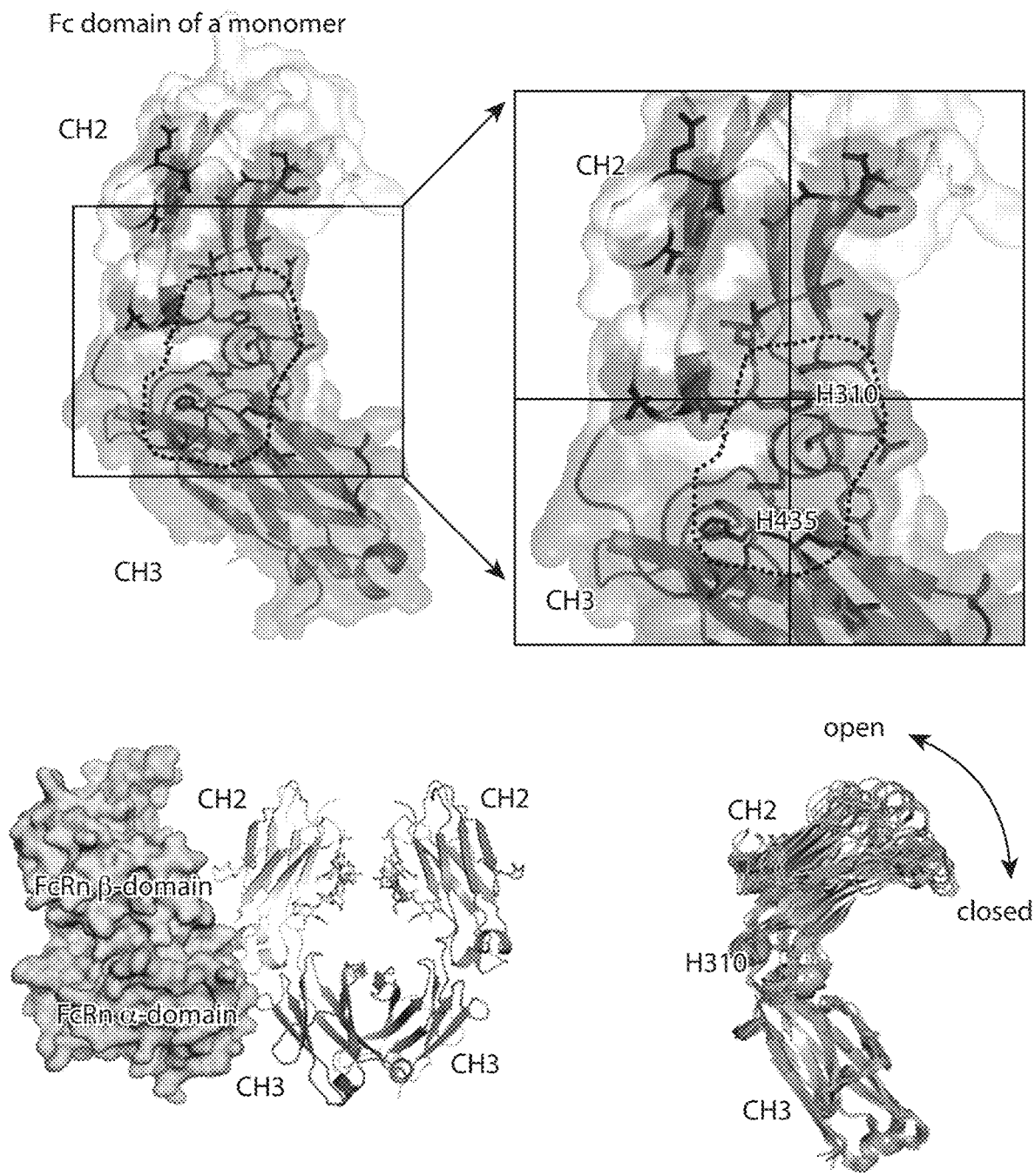
FIG. 4 depicts mapping of Fc-FcRn interaction interface. CH2 and CH3 domains are indicated and shown by different gray shades.

In an embodiment, the Fc region of an immunoglobulin monomer can have the structure shown in FIG. 4. As shown in FIG. 4, the black dotted line indicates the Fc-FcRn interaction interface. The structure includes FcRn contact residues and FcRn affinity enhancing Fc residues, e.g., as described herein. Residues H310 and H435, which are located in the CH2 and CH3 domains, respectively, are primarily responsible for the pH dependent Fc-FcRn interactions. In an embodiment, the FcRn binds the Fc region between its CH2 and CH3 domains. In another embodiment, the Fc-FcRn binding site is located across both the CH2 and CH3 domains of the Fc monomer.

Network View of Fc-FcRn Engagement Provides Insights on Co-Substitutions of Amino Acids In an embodiment, the polypeptide (e.g., antibody molecule or fusion protein) described herein comprises a plurality of mutations that can alter the interaction between an Fc region and an FcRn. In an embodiment, the mutation is selected based, at least in part, on a network view of the Fc-FcRn interaction.

Figure 5:
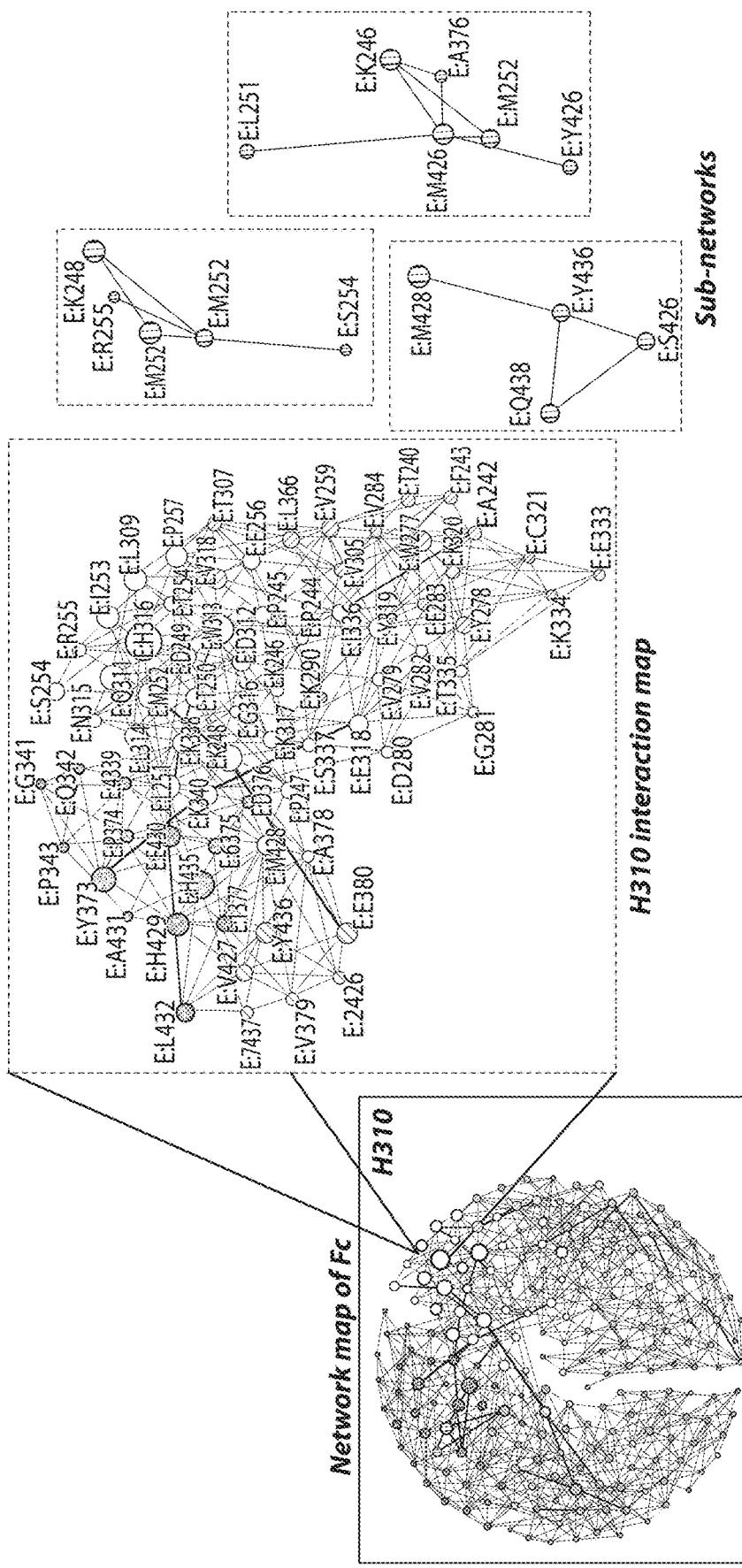
FIG. 5 depicts a network view of Fc-FcRn engagement.

Without wishing to be bound by theory, it is believed that in an embodiment, residue H310 plays a central role in engagement with the FcRn, e.g., as determined by a network analysis of the Fc-FcRn complex. As shown in FIG. 5, residue H310 is highly interconnected to multiple other highly networked residues. In an embodiment, a mutation in the H310 cluster, and neighboring (connected nodes), can strengthen the H310 network. Analysis of sub-networks informs introduction of synergistic mutations for favorable FcRn interaction; with reduced or minimal impact on other Fc residues.

Design Considerations for Optimizing FcRn Binding

In an embodiment, the polypeptide (e.g., antibody molecule or fusion protein) described herein can be designed for optimizing Fc-FcRn binding.

In an embodiment, the polypeptide having a mutation in the Fc region has a pH-specific affinity enhancement, compared to a reference polypeptide (e.g., an otherwise identical polypeptide without the mutation). In an embodiment, affinity enhancement is achieved by increasing van der Waal interaction. In an embodiment, affinity enhancement is not achieved by introduction of hydrogen bonds and/or electrostatic interaction. In an embodiment, the mutation does not alter, or has reduced or minimal perturbation to, the conformation of the linker region between the CH2 and CH3 domains. In an embodiment, the polypeptide comprises a plurality of mutations across both domains (four quadrants). In an embodiment, the polypeptide does not contain a large cluster of hydrophobic or aromatic residues on the surface.

In an embodiment, the polypeptide comprises a mutation that enhances the strength of interaction between an Fc region and FcRn or reduces the dissociation constant ($K_d$) for FcRn, e.g., at an acidic pH. In an embodiment, the polypeptide comprises a mutation that reduces the rate of dissociation ($k_{off}$) for FcRn, e.g., at an acidic pH. In an embodiment, the polypeptide comprises a mutation that increases the rate of association ($k_{on}$) for FcRn, e.g., at an acidic pH. In an embodiment, the polypeptide comprises a mutation that reduces the rate of dissociation ($k_{off}$) for FcRn, and increases the rate of association ($k_{on}$) for FcRn, e.g., at an acidic pH. In an embodiment, the polypeptide comprises a mutation that reduces the rate of dissociation ($k_{off}$) for FcRn, and does not, or does not significantly, affect the rate of association ($k_{on}$) for FcRn, e.g., at an acidic pH. Without wishing to be bound by theory, it is believed that in an embodiment, the reduction of the dissociation constant $K_d$ for FcRn is primarily resulted from the reduction of the rate of dissociation ($k_{off}$) for FcRn, rather than the increase of the rate of association ($k_{on}$).

Experimental Evaluation: Fc Mutations Assessed Along Multiple Dimensions and by Different Assay Platforms The polypeptides (e.g., antibody molecules or fusion proteins) described herein can be evaluated by a number of methods. The pH-specific Fc-FcRn binding (e.g., binding at pH6.0 and pH7.4) can be determined, e.g., by an Octet-based assay, a competition assay (e.g., flow cytometry), or surface plasmon resonance (SPR).

Biophysical characterization (e.g., thermal stability, aggregation, or expression) can be performed. Thermal stability can be determined, e.g., by SYPRO orange. Aggregation can be measured, e.g., by SEC or RP-HPLC.

Effector functions, e.g., relating to FcγRI (e.g., by an Octet-based assay), FcγRIIIa, FcγRIIa, FcγRIIb (e.g., by ELISA), C1q, ADCC, or CDC, can be tested.

Tripartite Motif-Containing Protein 21 (TRIM21) binding can be tested. TRIM21 is a cytosolic receptor that binds with Fc of IgG. TRIM21 plays a role in mediating intracellular recognition and neutralization of Fc bound pathogens such as viruses, bacteria and fungus. For example, TRIM21 plays an important role in the neutralization of non-enveloped viruses (McEwan et al. *Nat Immunol.* 2013; 14(4):327-36). Its role has been further expanded to include directing of immune complexes for degradation (McEwan et al. *Proc Natl Acad Sci USA.* 2017; 114(3):574-579). TRIM21 binds to the CH2:CH3 interface of the antibody Fc region, which overlaps with the FcRn binding site. Some Fc mutations that increase FcRn affinity decrease TRIM21 affinity (Foss et al. *J Immunol.* 2016; 196(8):3452-3459). Key contact residues include, e.g., positions 253, 433, 434, and 435. The LS variant (M428L/N434S) contains a mutation at position 434, and it has been shown that the N434S mutation causes a 10 fold decrease in TRIM21 binding. TRIM21-mediated neutralization is known as antibody dependent intracellular neutralization (ADIN).

Mucosal uptake can be tested. FcRn transports IgG across different cellular barriers such as the mucosal epithelium lining the intestine and the alveolar surfaces. Modification of FcRn binding provides a mechanism to enhance mucosal localization that confers immune protection.

The half-life of the polypeptide can be measured, e.g., using transgenic mice (e.g., Tg32 and Tg276 mice from Jackson's lab), or in primates (e.g., cynomolgus monkeys).

Exemplary assays are described in more detail as follows:

1. FcRn Binding Assays a. Octet Assay with Immobilization of FcRn to NiNTA Biosensors Immobilization of FcRn to a NiNTA biosensor via a 6× histidine tag (SEQ ID NO: 2) allows for subsequent interrogation of binding to IgG molecules under acidic (pH 6.0) and physiological (pH 7.4) conditions. This strategy has been previously described (1) and this method details an adaptation of the referenced protocol. Briefly, recombinant human FcRn at 5 µg/mL is loaded onto a NiNTA biosensor for 180 seconds. After a 60 second baseline step in 1×PBS pH 6.0, the FcRn loaded tip is exposed to IgG at a concentration of 250 nM (37.5 µg/mL) for 60 seconds, followed by dissociation for 60 seconds in PBS pH 6.0, and an additional 30 seconds in PBS pH 7.4. After assay completion, a quantitative assessment of the affinity constant ($K_D$) at pH 6.0 is performed using the ForteBio octet software and a qualitative assessment is performed by plotting the response rate over time, allowing for visualization of the association of IgG to FcRn at pH 6.0 and the subsequent dissociation at pH 6.0 and pH 7.4.

b. Octet Assay with Immobilization of IgG to Anti-CH1 Biosensors

Immobilization of IgG to an anti-CH1 biosensor allows for subsequent interrogation of binding to FcRn molecules under acidic (pH 6.0) and physiological (pH 7.4) conditions. This strategy has been previously described (2) and this method details an adaptation of the referenced protocol. Briefly, purified IgG at 5 µg/mL is loaded onto an anti-CH1 biosensor for 180 seconds. After a 60 second baseline step in 1×PBS pH 6.0, the IgG loaded tip is exposed to FcRn at a concentration of 50 µg/mL for 60 seconds, followed by dissociation for 60 seconds in PBS pH 6.0, and an additional 30 seconds in PBS pH 7.4. After assay completion, a quantitative assessment of the affinity constant ($K_D$) at pH 6.0 is performed using the ForteBio octet software and a qualitative assessment is performed by plotting the response rate over time, allowing for visualization of the association of IgG to FcRn at pH 6.0 and the subsequent dissociation at pH 6.0 and pH 7.4.

c. Cell Based Assay

Cell-based assays are also used to analyze the interactions between FcRn and IgG (Ref: PMID: 23384837). Expression of membrane-anchored FcRn on the cell surface closely represents the physiological presentation of FcRn, where the plasma membrane and molecular orientations influence interactions between FcRn and IgG. The assay used here is a competition assay in which IgGs of interest are evaluated for their ability to compete with cell binding of a fluorescently-labeled, high affinity Fc competitor reagent (Fc-A488). Expi293 cells expressing the full-length, membrane-bound FcRn heterodimer are incubated with mixtures of a static concentration of Fc-A488 (0.5 ug/ml) and varying concentrations of IgG of interest (0.001-10 µM). Cell-bound fluorescence is detected by flow cytometry. IgGs with improved binding to FcRn will compete off the Fc competitor at lower IgG concentrations. This assay is robust, linear, and specific and can be used to show differences in relative binding of IgG/Fc variants to FcRn.

2. Thermal Stability Assay

The stability of the IgG variants was assessed by Differential Scanning Fluorimetry (DSF) is an assay using SYPRO® Orange dye to monitor protein unfolding under thermal stress. SYPRO® Orange is a fluorescent dye that non-specifically binds to hydrophobic surfaces and its fluorescence is quenched in aqueous environments. Proteins begin to lose their secondary structure and unfold with increasing temperatures thus exposing their hydrophobic core residues, and allowing the dye to fluoresce. Maximum fluorescent signal is attained at complete unfolding, after which the protein begins to aggregate, reducing the exposed hydrophobic residues, and thus reducing the fluorescent signal. At the midpoint between native state and fully unfolded protein is the transition temperature, or melt temperature (Tm), which can be used to directly compare protein constructs or formulation conditions for relative stability.

In an embodiment, factors other than FcRn binding can also affect the observed half-life of a polypeptide (e.g., an antibody molecule or fusion protein). These factors can include, e.g., aggregation propensity, non-specific binding, stability, or Fab composition.

In an embodiment, a mutation in a non-Fc region is introduced, e.g., to provide a substantial improvement in half-life in the context of a suboptimal template. For example, polypeptides (e.g., antibody molecules or fusion proteins) with lower starting half-life may indicate the presence of suboptimal properties. Engineering efforts can also focus on mitigating the root cause of lower half-life, e.g., to maintain requisite binding profile (e.g., affinity and/or specificity), or to obtain suitable developability characteristics (e.g., stability, solubility, expression level, or aggregation). In an embodiment, additional engineering is performed for polypeptide (e.g., antibody molecules or fusion proteins) with suboptimal biophysical properties to realize maximal half-life extension.

Pharmacokinetics

The polypeptides (e.g., antibody molecules or fusion proteins) described herein can have one or more desired pharmacokinetic properties, e.g., one or more (e.g., 2, 3, 4, 5, or more) of the pharmacokinetic properties described herein.

Pharmacokinetics (PK) can be used to determine the fate of substances administered to a living organism. PK studies can be used to analyze drug metabolism and to identify the fate of a drug from the moment that it is administered up to the point at which it is completely eliminated from the body. Pharmacokinetics describes, e.g., how the body affects a specific drug after administration through the mechanisms of absorption and distribution, the chemical changes of the substance in the body (e.g. by metabolic enzymes such as cytochrome P450 or glucuronosyltransferase enzymes), or the effects and routes of excretion of the metabolites of the drug. Pharmacokinetic properties of drugs may be affected by elements such as the site of administration and the dose of administered drug, which may affect the absorption rate. Pharmacokinetics can be analyzed in conjunction with pharmacodynamics (e.g., the study of the biochemical and physiologic effects of drugs).

A number of different models have been developed for pharmacokinetics. For example, pharmacokinetic modelling can be performed by noncompartmental or compartmental methods.

Noncompartmental methods estimate the exposure to a drug by estimating the area under the curve of a concentration-time graph. Noncompartmental PK analysis is highly dependent on estimation of total drug exposure. Total drug exposure is often estimated by area under the curve (AUC) methods, with the trapezoidal rule (numerical integration) the most common method. Due to the dependence on the length of 'x' in the trapezoidal rule, the area estimation is highly dependent on the blood/plasma sampling schedule. That is, the closer time points are, the closer the trapezoids reflect the actual shape of the concentration-time curve.

Compartmental methods estimate the concentration-time graph using kinetic models. Compartmental PK analysis uses kinetic models to describe and predict the concentration-time curve. PK compartmental models are often similar to kinetic models used in other scientific disciplines such as chemical kinetics and thermodynamics. The advantage of compartmental over some noncompartmental analyses is the ability to predict the concentration at any time. Compartment-free modelling based on curve stripping does not suffer this limitation. The simplest PK compartmental model is the one-compartmental PK model with IV bolus administration and first-order elimination. The more complex PK models (e.g., PBPK models) rely on the use of physiological information to ease development and validation.

In a single-compartment model, the graph of the relationship between the various factors involved (e.g., dose, blood plasma concentrations, or elimination) gives a straight line or an approximation to one (i.e., linear pharmacokinetics). For drugs to be effective they need to be able to move rapidly from blood plasma to other body fluids and tissues.

In multi-compartmental models, the graph for the non-linear relationship between the various factors is represented by a curve, the relationships between the factors can then be found by calculating the dimensions of different areas under the curve. The models used in non-linear pharmacokinetics are largely based on Michaelis-Menten kinetics.

The various compartments that the model is divided into are commonly referred to as the ADME scheme (also referred to as LADME if liberation is included as a separate step from absorption): liberation (e.g., the process of release of a drug from the pharmaceutical formulation); absorption (e.g., the process of a substance entering the blood circulation); distribution (e.g., the dispersion or dissemination of substances throughout the fluids and tissues of the body); metabolism (or biotransformation, or inactivation) (e.g., the recognition by the organism that a foreign substance is present and the irreversible transformation of parent compounds into daughter metabolites); and excretion (e.g., the removal of the substances from the body). In rare cases, some drugs irreversibly accumulate in body tissue. The two phases of metabolism and excretion can also be grouped together under the title elimination.

All these parameters can be represented through mathematical formulas that have a corresponding graphical representation. The use of these models allows an understanding of the characteristics of a molecule, as well as how a particular drug will behave given information regarding some of its basic characteristics such as its acid dissociation constant (pKa), bioavailability and solubility, absorption capacity and distribution in the organism.

The model outputs for a drug can be used in industry (for example, in calculating bioequivalence when designing generic drugs) or in the clinical application of pharmacokinetic concepts. Clinical pharmacokinetics provides a number of performance guidelines for effective and efficient use of drugs for human-health professionals and in veterinary medicine.

Exemplary pharmacokinetic properties include, but are not limited to, dose (e.g., the amount of drug administered), dosing interval (e.g., the time between drug dose administrations), $C_{max}$ (e.g., the peak plasma concentration of a drug after administration), $t_{max}$ (e.g., the time to reach $C_{max}$), (e.g., the lowest concentration that a drug reaches before the next dose is administered), volume of distribution (e.g., the apparent volume in which a drug is distributed, e.g., relating drug concentration to drug amount in the body), concentration (e.g., the amount of drug in a given volume of plasma), half-life or elimination half-life (e.g., the time required for the concentration of the drug to reach half of its original value), elimination rate constant (e.g., the rate at which a drug is removed from the body), infusion rate (e.g., the rate of infusion required to balance elimination), area under the curve (e.g., the integral of the concentration-time curve, e.g., after a single dose or in steady state), clearance (e.g., the volume of plasma cleared of the drug per unit time), bioavailability (e.g., the systemically available fraction of a drug), or fluctuation (e.g., the peak trough fluctuation within one dosing interval at steady state).

Pharmacokinetic properties can be measured by various methods. For example, bioanalytical methods can be used to construct a concentration-time profile. Chemical techniques can be employed to measure the concentration of drugs in biological matrix, e.g., plasma. Proper bioanalytical methods should be selective and sensitive. For example, microscale thermophoresis can be used to quantify how the biological matrix/liquid affects the affinity of a drug to its target (Baaske et al. (2010). *Angew. Chem. Int. Ed.* 49 (12): 1-5; Wienken et al. (2010). *Nature Communications* 1 (7): 100).

Pharmacokinetic properties can also be studied using mass spectrometry, e.g., when there is a need for high sensitivity to observe concentrations after a low dose and a long time period. A common instrumentation used in this application is LC-MS with a triple quadrupole mass spectrometer. Tandem mass spectrometry can be employed for added specificity. Standard curves and internal standards can be used for quantitation of a pharmaceutical in the samples. The samples represent different time points as a pharmaceutical is administered and then metabolized or cleared from the body. Blank samples taken before administration are used in determining background and ensuring data integrity with such complex sample matrices. The standard curve can be linear, or curve fitting can be used with more complex functions such as quadratics since the response of most mass spectrometers is less than linear across large concentration ranges (Hsieh and Korfmacher (2006) Current Drug Metabolism 7 (5): 479-89; Covey et al. (1986) Anal. Chem. 58 (12): 2453-60; Covey et al. (1985). Anal. Chem. 57 (2): 474-81).

Exemplary Antibody Molecules

The methods described herein can be used to engineer a variety of antibody molecules, e.g., any antibody molecule containing an Fc region.

In an embodiment, the antibody molecule is a chimeric antibody molecule, a humanized antibody molecule, or a human antibody molecule.

In an embodiment, the antibody molecule is a whole monoclonal antibody. In another embodiment, the antibody molecule is an Fc region-containing derivative of an antibody molecule that does not contain an Fc region (e.g., an antigen-binding fragment described herein). Exemplary antigen-binding fragments include, but are not limited to, Fab, F(ab')2, Fab', scFv, di-scFv, or sdAb. In another embodiment, the antibody molecule is a bispecific monoclonal antibody, e.g., a trifunctional antibody (3funct) or bi-specific T-cell engager (BiTE).

In an embodiment, the antibody molecule targets a molecule (e.g., a protein) associated with an infectious disease (e.g., a viral infection, a bacterial infection, or a fungal infection). In another embodiment, the antibody molecule targets a molecule (e.g., a protein) or cell associated with a cancer. In another embodiment, the antibody molecule targets a molecule (e.g., a protein) or cell associated with an immune disorder. In another embodiment, the antibody molecule targets a molecule (e.g., a protein) or cell associated with a cardiovascular disorder. In another embodiment, the antibody molecule targets a molecule (e.g., a protein) or cell associated with a metabolic disorder. In another embodiment, the antibody molecule targets a molecule (e.g., a protein) or cell associated with a neurological disorder.

Exemplary antibody molecules include, but are not limited to, antibody molecules that target one or more (e.g., 2) of the following molecules or cells: β-amyloid, 4-1BB, SAC, 5T4, ACF9, ACFIX, activin receptor-like kinase 1, ACVR2B, an adenocarcinoma antigen, AGS-22M6, alpha-fetoprotein, angiopoietin 2, angiopoietin 3, a protective antigen of anthrax toxin, AOC3 (VAP-1), B7-H3, *bacillus anthracisanthrax*, BAFF, B-lymphoma cell, C242 antigen, C5, CA-125 (imitation), calcitonin, *canis lupus familiaris* IL31, carbonic anhydrase 9 (CA-IX), cardiac myosin, CCL11 (eotaxin-1), CCR2, CCR4, CCR5, CD11, CD18, CD125, CD140a, CD147 (basigin), CD15, CD152, CD154 (CD40L), CD19, CD2, CD20, CD200, CD22, CD221, CD23 (IgE receptor), CD25 (a chain of IL-2 receptor), CD27, CD274, CD276, CD28, CD3, CD3 epsilon, CD30 (TNFRSF8), CD33, CD37, CD38 (cyclic ADP ribose hydrolase), CD4, CD40, CD40 ligand, CD41 (integrin alpha-IIb), CD44 v6, CD5, CD51, CD52, CD56, CD6, CD70, CD74, CD79B, CD80, CEA, a CEA-related antigen, CFD, CGRP, ch4D5, CLDN18.2, *Clostridium difficile*, clumping factor A, coagulation factor III, CSF1R, CSF2, CTGF, CTLA-4, C—X—C chemokine receptor type 4, cytomegalovirus, cytomegalovirus glycoprotein B, dabigatran, DLL3, DLL4, DPP4, DRS, *E. coli* shiga toxintype-1, *E. coli* shiga toxintype-2, EGFL7, EGFR, endoglin, endotoxin, EpCAM, ephrin receptor A3, episialin, ERBB3, *Escherichia coli*, F protein of respiratory syncytial virus, FAP, fibrin II beta chain, fibronectin extra domain-B, folate hydrolase, folate receptor 1, folate receptor alpha, Frizzled receptor, ganglioside GD2, GCGR, GD2, GD3 ganglioside, GDF-8, glypican 3, GMCSF receptor α-chain, GPNMB, growth differentiation factor8, GUCY2C, hemagglutinin, hepatitis B surface antigen, hepatitis B virus, HER1, HER2/neu, HER3, HGF, HHGFR, histone complex, HIV-1, HLA-DR, HNGF, Hsp90, human scatter factor receptor kinase, human TNF, human beta-amyloid, ICAM-1 (CD54), ICOSL, IFN-α, IFN-γ, IgE, IgE Fc region, IGF-1 receptor, IGF-I, IGHE, IL 20, IL-1, IL-12, IL-13, IL-17, IL-17A, IL-17F, IL-1β, IL2, IL-22, IL-23, IL23A, IL31RA, IL-4, IL-4, IL-5, IL6, IL-6 receptor (IL6R), IL-9, ILGF2, influenza A virus hemagglutinin (HA), insulin-like growth factor I receptor, integrin α4, integrin α4β7, integrin α5β1, integrin α7β7, integrin αIIbβ3, integrin αvβ3, interferon receptor, interferon α/β receptor, interferon gamma-induced protein, ITGA2, ITGB2 (CD18), kallikrein, KIR2D, KLRC1, Lewis-Y antigen, LFA-1 (CD11a), LFA-1 (CD11a), LINGO-1, lipoteichoic acid, LOXL2, L-selectin (CD62L), LTA, MCP-1, mesothelin, MIF, MS4A1, MSLN, MUC1, mucin CanAg, myelin-associated glycoprotein, myostatin, NCA-90 (granulocyte antigen), NCA-90 (granulocyte antigen), neural apoptosis-regulated proteinase 1, neural apoptosis-regulated proteinase 1, NGF, NGF, N-glycolylneuraminic acid, NOGO-A, Notch 1, Notch receptor, NRP1, *Oryctolagus cuniculus*, OX-40, oxLDL, PCSK9, PD-1, PD-1, PDCD1, PDGF-R α, phosphate-sodium co-transporter, phosphatidylserine, platelet-derived growth factor receptor beta, prostatic carcinoma cells, *Pseudomonas aeruginosa, Pseudomonas aeruginosa* type III secretion system, rabies virus glycoprotein, rabies virus glycoprotein, RANKL, respiratory syncytial virus, respiratory syncytial virus, RHD, Rhesus factor, Rhesus factor, RON, RTN4, sclerostin, SDC1, selectin P, SLAMF7, SOST, sphingosine-1-phosphate, *Staphylococcus aureus*, STEAP1, TAG-72, T-cell receptor, TEM1, tenascin C, TFPI, TGF beta 1, TGF beta 2, TGF-β, TNFR superfamily member 4, TNF-α, TRAIL-R1, TRAIL-R2, TSLP, tumor antigen CTAA16.88, tumor specific glycosylation of MUC1, tumor-associated calcium signal transducer 2, TWEAK receptor, TYRP1(glycoprotein 75), VEGFA, VEGFR-1, VEGFR2, vimentin, or VWF.

Exemplary antibody molecules include, but are not limited to, antibody molecules that target one or more (e.g., 2) of the following pathogens (e.g., bacteria, viruses, or fungi): *Actinomyces gerencseriae, Actinomyces israelii, Actinomycetoma* species, Alphavirus, *Anaplasma phagocytophilum, Anaplasma* species, *Ancylostoma braziliense, Ancylostoma duodenale, Angiostrongylus, Anisakis, Arcanobacterium haemolyticum, Ascaris lumbricoides, Aspergillus* species, Astroviridae family, *Babesia* species, *Bacillus anthracis, Bacillus cereus*, bacterial vaginosis microbiota, *Bacteroides* species, *Balantidium coli, Bartonella, Bartonella bacilliformis, Bartonella henselae, Batrachochytrium dendrabatidis, Baylisascaris* species, BK virus, *Blastocystis* species, *Blastomyces dermatitidis, Bordetella pertussis, Borrelia afzelii, Borrelia burgdorferi, Borrelia garinii, Borrelia hermsii, Borrelia recurrentis, Borrelia* species, *Brucella* species, *Brugia malayi*, Bunyaviridae family, *Burkholderia cepacia, Burkholderia mallei, Burkholderia pseudomallei, Burkholderia* species, Caliciviridae family, *Campylobacter* species, *Candida albicans, Candida* species, *Capillaria aerophila, Capillaria hepatica, Capillaria philippinensis, Chlamydia trachomatis, Chlamydia trachomatis, Chlamydia trachomatis, Chlamydophila pneumoniae, Chlamydophila psittaci, Clonorchis sinensis, Clostridium botulinum, Clostridium difficile, Clostridium perfringens, Clostridium perfringens, Clostridium tetani, Clostridium* species, *Coccidioides immitis, Coccidioides immitis, Coccidioides posadasii, Coccidioides posadasii*, Colorado tick fever virus (CTFV), coronaviruses, *Corynebacterium diphtheriae, Coxiella burnetii*, Coxsackie A virus and Enterovirus 71 (EV71), Crimean-Congo hemorrhagic fever virus, *Cryptococcus neoformans, Cryptosporidium* species, *Cyclospora cayetanensis*, Cytomegalovirus, Dengue viruses (DEN-1, DEN-2, DEN-3 or DEN-4), *Dientamoeba fragilis, Diphyllobothrium, Dracunculus medinensis*, Ebolavirus (EBOV), *Echinococcus* species, *Ehrlichia chaffeensis, Ehrlichia ewingii, Ehrlichia* species, *Entamoeba histolytica*, Enterobacteriaceae family, *Enterobius vermicularis, Enterococcus* species, Enterovirus species, Enteroviruses, Entomophthorales order (Entomophthoramycosis), *Epidermophyton floccosum*, Epstein-Barr Virus (EBV), *Escherichia coli* O157:H7, *Eumycetoma* species, *Fasciola hepatica* and *Fasciola gigantica, Fasciolopsis buski*, Filarioidea superfamily, Flavivirus, *Fonsecaea pedrosoi, Francisella tularensis, Fusobacterium* species, *Geotrichum candidum, Giardia lamblia, Gnathostoma hispidum, Gnathostoma spinigerum*, Green algae *Desmodesmus armatus*, Group A *Streptococcus*, Guanarito virus, *Haemophilus ducreyi, Haemophilus influenzae*, Heartland virus, *Helicobacter pylori*, Hepatitis A virus, Hepatitis B virus, Hepatitis C virus, Hepatitis D Virus, Hepatitis E virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), *Hymenolepis diminuta, Hymenolepis nana, Isospora belli*, JC virus, Junin virus, *Kingella kingae, Klebsiella granulomatis*, Lassa virus, *Legionella pneumophila, Leishmania* species, *Leptospira* species, *Listeria monocytogenes*, Lymphocytic choriomeningitis virus (LCMV), Machupo virus, *Malassezia* species, Marburg virus, Measles virus, Measles virus, *Metagonimus yokagawai*, Microsporidia phylum, Middle East respiratory syndrome coronavirus, *Molluscum contagiosum* virus (MCV), Monkeypox virus, Mucorales order (Mucormycosis), Mumps virus, *Mycobacterium leprae, Mycobacterium lepromatosis, Mycobacterium tuberculosis, Mycobacterium ulcerans, Mycoplasma pneumoniae, Naegleria fowleri, Necator americanus, Neisseria gonorrhoeae, Neisseria gonorrhoeae, Neisseria meningitidis, Nocardia asteroids, Nocardia* species, O111 and O104:H4, *Onchocerca volvulus, Opisthorchis felineus, Opisthorchis viverrini*, Orthomyxoviridae family, *Paracoccidioides brasiliensis, Paragonimus westermani, Paragonimus* species, parasitic dipterous fly larvae, Parvovirus B19, *Pasteurella* species, *Pediculus humanus capitis, Pediculus humanus corporis, Phthirus pubis, Piedraia hortae, Plasmodium* species, *Pneumocystis jirovecii*, Poliovirus, *Prevotella* species, PRNP, *Propionibacterium propionicus*, Rabies virus, Respiratory syncytial virus (RSV), *Rhinosporidium seeberi*, Rhinovirus, rhinoviruses, *Rickettsia, Rickettsia akari, Rickettsia prowazekii, Rickettsia rickettsii, Rickettsia typhi, Rickettsia* species, Rift Valley fever virus, Rotavirus, Rubella virus, Sabia, *Salmonella enterica* subsp. *enterica, Salmonella* species, Sarcoptes scabiei, SARS coronavirus, *Schistosoma* species, serovar *typhi, Shigella* species, Sin Nombre virus, *Sporothrix schenckii, Staphylococcus, Staphylococcus* species, *Staphylococcus* species, *Streptococcus agalactiae, Streptococcus pneumoniae, Streptococcus pyogenes, Strongyloides stercoralis, Taenia solium, Taenia* species, *Toxocara canis, Toxocara cati, Toxoplasma gondii, Treponema pallidum*,

*Trichinella spiralis, Trichomonas vaginalis, Trichophyton mentagrophytes, Trichophyton rubrum, Trichophyton rubrum, Trichophyton tonsurans, Trichophyton species, Trichosporon beigelii, Trichuris trichiura, Trypanosoma brucei, Trypanosoma cruzi, Ureaplasma urealyticum*, Varicella zoster virus (VZV), Variola major, Variola minor, Venezuelan equine encephalitis virus, *Vibrio cholerae, Vibrio parahaemolyticus, Vibrio vulnificus*, West Nile virus, *Wuchereria bancrofti*, Yellow fever virus, *Yersinia enterocolitica, Yersinia pestis, Yersinia pseudotuberculosis*, or Zika virus, Exemplary antibody molecules include, but are not limited to, 3f8, 8h9, abagovomab, abciximab, abituzumab, abrilumab, actoxumab, adalimumab, adecatumumab, aducanumab, afasevikumab, afelimomab, afutuzumab, alacizumab pegol, ald518, alemtuzumab, alirocumab, altumomab pentetate, amatuximab, anatumomab mafenatox, anetumab ravtansine, anifrolumab, anrukinzumab (ima-638), apolizumab, arcitumomab, ascrinvacumab, aselizumab, atezolizumab, atinumab, atlizumab (tocilizumab), atorolimumab, avelumab, bapineuzumab, basiliximab, bavituximab, bectumomab, begelomab, belimumab, benralizumab, bertilimumab, besilesomab, bevacizumab, bezlotoxumab, biciromab, bimagrumab, bimekizumab, bivatuzumab mertansine, bleselumab, blinatumomab, blontuvetmab, blosozumab, bococizumab, brazikumab, brentuximab vedotin, briakinumab, brodalumab, brolucizumab, brontictuzumab, cabiralizumab, canakinumab, cantuzumab mertansine, cantuzumab ravtansine, caplacizumab, capromab pendetide, carlumab, carotuximab, catumaxomab, cbr96-doxorubicin immunoconjugate, cedelizumab, cergutuzumab amunaleukin, certolizumab pegol, cetuximab, ch.14.18, citatuzumab bogatox, cixutumumab, clazakizumab, clenoliximab, clivatuzumab tetraxetan, codrituzumab, coltuximab ravtansine, conatumumab, concizumab, crenezumab, crotedumab, cr6261, dacetuzumab, daclizumab, dalotuzumab, dapirolizumab pegol, daratumumab, dectrekumab, demcizumab, denintuzumab mafodotin, denosumab, derlotuximab biotin, detumomab, dinutuximab, diridavumab, domagrozumab, dorlimomab aritox, drozitumab, duligotumab, dupilumab, durvalumab, dusigitumab, ecromeximab, eculizumab, edobacomab, edrecolomab, efalizumab, efungumab, eldelumab, elgemtumab, elotuzumab, elsilimomab, emactuzumab, emibetuzumab, emicizumab, enavatuzumab, enfortumab vedotin, enlimomab pegol, enoblituzumab, enokizumab, enoticumab, ensituximab, epitumomab cituxetan, epratuzumab, erenumab, erlizumab, ertumaxomab, etaracizumab, etrolizumab, evinacumab, evolocumab, exbivirumab, fanolesomab, faralimomab, farletuzumab, fasinumab, fbta05, felvizumab, fezakinumab, fibatuzumab, ficlatuzumab, figitumumab, firivumab, flanvotumab, fletikumab, fontolizumab, foralumab, foravirumab, fresolimumab, fulranumab, futuximab, galcanezumab, galiximab, ganitumab, gantenerumab, gavilimomab, gemtuzumab ozogamicin, gevokizumab, girentuximab, glembatumumab vedotin, golimumab, gomiliximab, guselkumab, ibalizumab, ibritumomab tiuxetan, icrucumab, idarucizumab, igovomab, imab362, imalumab, imciromab, imgatuzumab, inclacumab, indatuximab ravtansine, indusatumab vedotin, inebilizumab, infliximab, intetumumab, inolimomab, inotuzumab ozogamicin, ipilimumab, iratumumab, isatuximab, itolizumab, ixekizumab, keliximab, labetuzumab, lambrolizumab, lampalizumab, lanadelumab, landogrozumab, lapritiuximab emtansine, lebrikizumab, lemalesomab, lendalizumab, lenzilumab, lerdelimumab, lexatumumab, libivirumab, lifastuzumab vedotin, ligelizumab, lilotomab satetraxetan, lintuzumab, lirilumab, lodelcizumab, lokivetmab, lorvotuzumab mertansine, lucatumumab, lulizumab pegol, lumiliximab, lumretuzumab, mapatumumab, margetuximab, maslimomab, mavrilimumab, matuzumab, mepolizumab, metelimumab, milatuzumab, minretumomab, mirvetuximab soravtansine, mitumomab, mogamulizumab, monalizumab, morolimumab, motavizumab, moxetumomab pasudotox, muromonab-cd3, nacolomab tafenatox, namilumab, naptumomab estafenatox, naratuximab emtansine, narnatumab, natalizumab, navicixizumab, navivumab, nebacumab, necitumumab, nemolizumab, nerelimomab, nesvacumab, nimotuzumab, nivolumab, nofetumomab merpentan, obiltoxaximab, obinutuzumab, ocaratuzumab, ocrelizumab, odulimomab, ofatumumab, olaratumab, olokizumab, omalizumab, onartuzumab, ontuxizumab, opicinumab, oportuzumab monatox, oregovomab, orticumab, otelixizumab, otlertuzumab, oxelumab, ozanezumab, ozoralizumab, pagibaximab, palivizumab, pamrevlumab, panitumumab, pankomab, panobacumab, parsatuzumab, pascolizumab, pasotuxizumab, pateclizumab, patritumab, pembrolizumab, pemtumomab, perakizumab, pertuzumab, pexelizumab, pidilizumab, pinatuzumab vedotin, pintumomab, placulumab, plozalizumab, pogalizumab, polatuzumab vedotin, ponezumab, prezalizumab, priliximab, pritoxaximab, pritumumab, pro 140, quilizumab, racotumomab, radretumab, rafivirumab, ralpancizumab, ramucirumab, ranibizumab, raxibacumab, refanezumab, regavirumab, reslizumab, rilotumumab, rinucumab, risankizumab, rituximab, rivabazumab pegol, robatumumab, roledumab, romosozumab, rontalizumab, rovalpituzumab tesirine, rovelizumab, ruplizumab, sacituzumab govitecan, samalizumab, sapelizumab, sarilumab, satumomab pendetide, secukinumab, seribantumab, setoxaximab, sevirumab, sibrotuzumab, sgn-cd19a, sgn-cd33a, sifalimumab, siltuximab, simtuzumab, siplizumab, sirukumab, sofituzumab vedotin, solanezumab, solitomab, sonepcizumab, sontuzumab, stamulumab, sulesomab, suvizumab, tabalumab, tacatuzumab tetraxetan, tadocizumab, talizumab, tamtuvetmab, tanezumab, taplitumomab paptox, tarextumab, tefibazumab, telimomab aritox, tenatumomab, teneliximab, teplizumab, teprotumumab, tesidolumab, tetulomab, tezepelumab, tgn1412, ticilimumab (tremelimumab), tildrakizumab, tigatuzumab, timolumab, tisotumab vedotin, tnx-650, tocilizumab (atlizumab), toralizumab, tosatoxumab, tositumomab, tovetumab, tralokinumab, trastuzumab, trastuzumab emtansine, trbs07, tregalizumab, tremelimumab, trevogrumab, tucotuzumab celmoleukin, tuvirumab, ublituximab, ulocuplumab, urelumab, urtoxazumab, ustekinumab, utomilumab, vadastuximab talirine, vandortuzumab vedotin, vantictumab, vanucizumab, vapaliximab, varlilumab, vatelizumab, vedolizumab, veltuzumab, vepalimomab, vesencumab, visilizumab, vobarilizumab, volociximab, vorsetuzumab mafodotin, votumumab, xentuzumab, zalutumumab, zanolimumab, zatuximab, ziralimumab, zolimomab aritox, or derivative thereof.

In an embodiment, the antibody molecule comprises one, two, or three CDRs of the VH region of an antibody molecule described herein, using the Kabat or Chothia definitions of CDRs. In an embodiment, the antibody molecule comprises one, two, or three CDRs of the VL region of an antibody molecule described herein, using the Kabat or Chothia definitions of CDRs. In an embodiment, the antibody molecule comprises one or more (e.g., two or three) CDRs of the VH region and/or one or more (e.g., two or three) CDRs of the VL region of an antibody molecule described herein, using the Kabat or Chothia definitions of CDRs.

In an embodiment, the antibody molecule comprises one, two, three, or four frameworks of the VH region of an antibody molecule described herein. In an embodiment, the antibody molecule comprises one, two, three, or four frameworks of the VL region of an antibody molecule described herein. In an embodiment, the antibody molecule comprises one or more (e.g., two, three, or four) frameworks of the VH region and/or one or more (e.g., two, three, or four) frameworks of the VL region of an antibody molecule described herein.

In an embodiment, the antibody molecule comprises a heavy chain variable region of an antibody molecule described herein, or a heavy chain variable region having an amino acid sequence substantially identical thereto (e.g., an amino acid sequence at least about 85%, 90%, 95%, 99% or more identical thereto, or which differs by no more than 1, 2, 5, 10, or 15 amino acid residues). In an embodiment, the antibody molecule comprises a light chain variable region of an antibody molecule described herein, or a light chain variable region having an amino acid sequence substantially identical thereto (e.g., an amino acid sequence at least about 85%, 90%, 95%, 99% or more identical thereto, or which differs by no more than 1, 2, 5, 10, or 15 amino acid residues). In an embodiment, the antibody molecule comprises a heavy chain variable region, or a heavy chain variable region having an amino acid sequence substantially identical thereto (e.g., an amino acid sequence at least about 85%, 90%, 95%, 99% or more identical thereto, or which differs by no more than 1, 2, 5, 10, or 15 amino acid residues), and a light chain variable region of an antibody molecule described herein, or a light chain variable region having an amino acid sequence substantially identical thereto (e.g., an amino acid sequence at least about 85%, 90%, 95%, 99% or more identical thereto, or which differs by no more than 1, 2, 5, 10, or 15 amino acid residues).

In an embodiment, the antibody molecule further comprises a heavy chain constant region, e.g., a heavy chain constant region of an antibody molecule described herein, or a heavy chain constant region having an amino acid sequence substantially identical thereto (e.g., an amino acid sequence at least about 85%, 90%, 95%, 99% or more identical thereto, or which differs by no more than 1, 2, 5, 10, or 15 amino acid residues). In an embodiment, the antibody molecule further comprises a light chain constant region, e.g., a light chain constant region of an antibody molecule described herein, or a light chain constant region having an amino acid sequence substantially identical thereto (e.g., an amino acid sequence at least about 85%, 90%, 95%, 99% or more identical thereto, or which differs by no more than 1, 2, 5, 10, or 15 amino acid residues). In an embodiment, the antibody molecule further comprises a heavy chain constant region, or a heavy chain constant region having an amino acid sequence substantially identical thereto (e.g., an amino acid sequence at least about 85%, 90%, 95%, 99% or more identical thereto, or which differs by no more than 1, 2, 5, 10, or 15 amino acid residues), and a light chain constant region, or a light chain constant region having an amino acid sequence substantially identical thereto (e.g., an amino acid sequence at least about 85%, 90%, 95%, 99% or more identical thereto, or which differs by no more than 1, 2, 5, 10, or 15 amino acid residues). In an embodiment, the antibody molecule comprises a heavy chain constant region, a light chain constant region, and heavy and light chain variable regions of an antibody molecule, as described herein.

The antibody molecules described herein can have several advantageous properties, including, but not limited to, a desired (e.g., increased) half-life. For example, the antibody molecules can be used to effectively treat, prevent or diagnose a disorder described herein.

In an embodiment, the antibody molecule is capable of binding to a target molecule or cell. For example, the engineered antibody molecule is capable of binding to the target molecule or cell, with the same, or substantially the same, binding specificity and/or affinity, as compared to the parental antibody molecule. In an embodiment, the antibody molecule binds to the target molecule or cell with high affinity, e.g., with a dissociation constant ($K_d$) of less than about 100 nM, typically about 10 nM, and more typically, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, or 0.01 nM. In an embodiment, the antibody molecule binds to the target molecule or cell with a $K_{off}$ slower than $1\times10^{-4}$, $5\times10^{-5}$, or $1\times10^{-5}$ $s^{-1}$. In an embodiment, the antibody molecule binds to the target molecule or cell with a $K_{on}$ faster than $1\times10^4$, $5\times10^4$, $1\times10^5$, or $5\times10^5$ $M^{-1}s^{-1}$.

In an embodiment, the antibody molecule is capable of inhibiting or activating a biological function of a target molecule or cell. For example, the engineered antibody molecule is capable of inhibiting or activating a biological function of the target molecule or cell, with the same, or substantially the same, level of effectiveness, as compared to the parental antibody molecule, e.g., as determined by IC50, EC50, or LD50.

In an embodiment, the antibody molecule is capable of binding to an epitope on a target molecule or cell. For example, the engineered antibody molecule is capable of binding to the same, or substantially the same, epitope on the target molecule or cell, as compared to the parental antibody molecule.

Exemplary Fusion Proteins

The methods described herein can be used to engineer a variety of fusion proteins, e.g., any Fc fusion protein containing an Fc region.

Exemplary Fc fusion proteins include, but are not limited to, a CTLA-4 Fc fusion protein (e.g., belatacept or abatacept), a vascular endothelial growth factor receptor (VEGFR) Fc fusion protein (e.g., a VEGFR1/VEGFR2 Fc fusion protein, e.g., aflibercept or KH902), an IL-1R Fc fusion protein (e.g., (rilonacept), a thrombopoietin-binding peptide Fc fusion protein (e.g., romiplostim), an LFA-3 Fc fusion protein (e.g., alefacept), an anti-CD40L Fc fusion protein (e.g., a dimeric fusion protein comprising the C-terminus of the domain antibody (dAb) targeting the CD40 ligand (CD40L or CD154) linked to an Fc fragment of IgG1, e.g., BMS-986004 or letolizumab), an TNF receptor (TNFR) Fc fusion protein (e.g., a recombinant TNF receptor 2 (TNFR2) fused to an IgG1 Fc domain, e.g., OPRX-106 or etanercept), a coagulation Factor VIII-Fc fusion protein (e.g., BIIB031, efraloctocog-α, or rFVIIIFc), a coagulation Factor IX-Fc Fusion Protein (e.g., BIIB029 or eftrenonacog-α), a Factor IX Fc fusion protein (e.g., rFIXFc), a granulocyte colony-stimulating factor Fc fusion protein (e.g., F-627), a follicle stimulating hormone (FSH) Fc fusion protein (e.g., KN015), an activin type 2B receptor Fc fusion protein (e.g., STM 434), an activin receptor-like kinase 1 (ALK-1) inhibitor receptor Fc fusion protein (e.g., dalantercept), an RNase Fc fusion (e.g., RSLV-132), an anti-angiopoietin peptibody (e.g., a peptide with angiopoietin-binding properties that is fused to the Fc region, e.g., AMG 386), a tissue nonspecific alkaline phosphatase (TNSALP) Fc fusion protein (e.g., asfotase alfa or ENB-0040), a CD24 Fc fusion protein, a BAFF-Fc fusion protein (e.g., blisibimod), a GLP1 peptide analog Fc fusion protein (e.g., dulaglutide or LY2189265), an erythropoietin-mimetic peptide Fc fusion protein (e.g., an erythropoietin-mimetic peptide-IgG1 Fc mimetibody (e.g., CNTO 528), or an erythropoietin-mimetic peptide-IgG4 Fc fusion protein mimetibody (e.g., CNTO 530)), or a CD95 Fc fusion (e.g., APG 101 or apocept).

Animal Models

The polypeptides (e.g., antibody molecules or fusion proteins) described herein can be evaluated in vivo, e.g., using various animal models. For example, an animal model can be used to test the efficacy of a polypeptide (e.g., antibody molecule or fusion proteins) described herein in modulating a biological function of a target molecule or cell. As another example, an animal model can also be used to test the efficacy of a polypeptide (e.g., antibody molecule) described herein in in treating, preventing, or diagnosing a disorder described herein. Animal models can also be used, e.g., to investigate for side effects, measure concentrations of antibody molecules in situ, demonstrate correlations between a function of a target molecule or cell and a disorder described herein.

Exemplary animal models for other disorders described herein are also known in the art. Exemplary types of animals that can be used to evaluate the antibody molecules described herein include, but are not limited to, mice, rats, rabbits, guinea pigs, and monkeys. Non-human primates and transgenic mice expressing human FcRn are typically used as the model of choice for PK analysis (Avery et al. *MAbs.* 2016; 8(6):1064-78; Fan et al. *MAbs.* 2016; 8(5):848-53; Tam et al. *MAbs.* 2013; 5(3):397-405).

For example, humanized FcRn mice can be established on the C57BL/6J background in a sequential manner, including the creation of a mouse strain carrying a deletion in the mouse FcRn gene, followed by introduction of the human FcRn gene. Exemplary mouse lines include, e.g., Tg276 and Tg32 (The Jackson Laboratory stock number 004919 and 014565). With further backcrossing and sequential alterations, additional lines can be made. Exemplary mouse models that can be used to evaluate the polypeptides described herein include, but are not limited to, FcRn-null mice, humanized Tg276 FcRn mice (e.g., B6.Cg-Fcgrt<tm1Dcr>Tg(CAG-FCGRT)276Dcr/DcrJ with the Jackson Laboratory stock number 004919), humanized Tg32 FcRn mice (e.g., B6.Cg-Fcgrt<tm1Dcr>Tg(FCGRT) 32Dcr/DcrJ with the Jackson Laboratory stock number 014565), immunodeficient hFcRn mice (e.g., B6.Cg-Fcgrt<tm1Dcr>Prkdc<scid>Tg(CAG-FCGRT)276Dcr/DcrJ with the Jackson Laboratory stock number 021146), B6.Cg-Fcgrt<tm1Dcr>Prkdc <scid>Tg(FCGRT)32Dcr/DcrJ with the Jackson Laboratory stock number 018441, and B6.Cg-Rag1<tm>Mom<Fcgrt>tm1Dcr[Tg(CAG-FCGRT)276Dcr/DcrJ with the Jackson Laboratory stock number 16919), e.g., as described in Proetzel et al. *BioDrugs.* 2014; 28(2): 171-180.

Pharmaceutical Compositions and Kits

In some aspects, this disclosure provides compositions, e.g., pharmaceutically acceptable compositions, which include a polypeptide (e.g., an antibody molecule or fusion protein) described herein, formulated together with a pharmaceutically acceptable carrier.

As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g., by injection or infusion). In certain embodiments, less than about 5%, e.g., less than about 4%, 3%, 2%, or 1% of the antibody molecules in the pharmaceutical composition are present as aggregates. In other embodiments, at least about 95%, e.g., at least about 96%, 97%, 98%, 98.5%, 99%, 99.5%, 99.8%, or more of the antibody molecules in the pharmaceutical composition are present as monomers. In some embodiments, the level of aggregates or monomers is determined by chromatography, e.g., high performance liquid chromatography size exclusion chromatography (HPLC-SEC).

The compositions set out herein may be in a variety of forms. These include, for example, liquid, semi-solid and solid dosage forms, such as liquid solutions (e.g., injectable and infusible solutions), dispersions or suspensions, liposomes, and suppositories. A suitable form depends on the intended mode of administration and therapeutic application. Typical suitable compositions are in the form of injectable or infusible solutions. One suitable mode of administration is parenteral (e.g., intravenous, subcutaneous, intraperitoneal, intramuscular). In an embodiment, the polypeptide (e.g., antibody molecule or fusion proteins) is administered by intravenous infusion or injection. In another embodiment, the polypeptide (e.g., antibody molecule or fusion proteins) is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The polypeptides (e.g., antibody molecules or fusion proteins) described herein can be administered by a variety of methods. Several are known in the art, and for many therapeutic, prophylactic, or diagnostic applications, an appropriate route/mode of administration is intravenous injection or infusion. For example, the antibody molecules can be administered by intravenous infusion at a rate of less than 10 mg/min; preferably less than or equal to 5 mg/min to reach a dose of about 1 to 100 mg/m², preferably about 5 to 50 mg/m², about 7 to 25 mg/m² and more preferably, about 10 mg/m². As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, a polypeptide (e.g., an antibody molecule or fusion protein) can be orally administered, for example, with an inert diluent or an assimilable edible carrier. The antibody molecule (and other ingredients, if desired) may also be enclosed in a hard or soft shell gelatin capsule, compressed into tablets, or incorporated directly into the subject's diet. For oral therapeutic administration, the antibody molecule may be incorporated with excipients and used in the form of ingestible tablets, buccal tablets, troches, capsules, elixirs, suspensions, syrups, wafers, and the like. To administer a polypeptide (e.g., an antibody molecule) by other than parenteral administration, it may be necessary to coat the compound with, or co-administer the compound with, a material to prevent its inactivation. Therapeutic, prophylactic, or diagnostic compositions can also be administered with medical devices, and several are known in the art.

Dosage regimens are adjusted to provide the desired response (e.g., a therapeutic, prophylactic, or diagnostic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the antibody molecule and the particular therapeutic, prophylactic, or diagnostic effect to be achieved, and (b) the limitations inherent in the art of compounding such an antibody molecule for the treatment of sensitivity in individuals.

An exemplary, non-limiting range for a therapeutically, prophylactically, or diagnostically effective amount of an antibody molecule is about 0.1-50 mg/kg, e.g., about 0.1-30 mg/kg, e.g., about 1-30, 1-15, 1-10, 1-5, 5-10, or 1-3 mg/kg, e.g., about 1, 2, 3, 4, 5, 6, 7, 8, 9, 10, 15, 20, 30, 40, or 50 mg/kg. The antibody molecule can be administered by intravenous infusion at a rate of less than 10 mg/min, e.g., less than or equal to 5 mg/min to reach a dose of about 1 to 100 mg/m², e.g., about 5 to 50 mg/m², about 7 to 25 mg/m², e.g., about 10 mg/m². It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed compositions.

The pharmaceutical compositions herein may include a "therapeutically effective amount," "prophylactically effective amount," or "diagnostically effectively amount" of a polypeptide (e.g., an antibody molecule) described herein.

A "therapeutically effective amount" refers to an amount effective, at dosages and for periods of time necessary, to achieve the desired therapeutic result. A therapeutically effective amount of the polypeptide (e.g., antibody molecule or fusion protein) may vary according to factors such as the disease state, age, sex, and weight of the individual, and the ability of the antibody or antibody portion to elicit a desired response in the individual. A therapeutically effective amount is also one in which any toxic or detrimental effect of the antibody molecule is outweighed by the therapeutically beneficial effects. A "therapeutically effective dosage" typically inhibits a measurable parameter by at least about 20%, e.g., by at least about 40%, by at least about 60%, or by at least about 80% relative to untreated subjects. The measurable parameter may be, e.g., hematuria, colored urine, foamy urine, pain, swelling (edema) in the hands and feet, or high blood pressure. The ability of an antibody molecule to inhibit a measurable parameter can be evaluated in an animal model system predictive of efficacy in treating or preventing a disorder described herein. Alternatively, this property of a composition can be evaluated by examining the ability of the polypeptide (e.g., antibody molecule or fusion proteins) to modulate a biological function of a target molecule or cell, e.g., by an in vitro assay.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A "diagnostically effective amount" refers to an amount effective, at dosages and for periods of time necessary, to achieve the desired diagnostic result. Typically, a diagnostically effective amount is one in which a disorder, e.g., a disorder described herein, can be diagnosed in vitro, ex vivo, or in vivo.

Also within this disclosure is a kit that comprises a polypeptide (e.g., an antibody molecule or fusion protein), described herein. The kit can include one or more other elements including: instructions for use; other reagents, e.g., a label, a therapeutic agent, or an agent useful for chelating, or otherwise coupling, an antibody molecule to a label or therapeutic agent, or a radioprotective composition; devices or other materials for preparing the polypeptide (e.g., antibody molecule or fusion protein) for administration; pharmaceutically acceptable carriers; and devices or other materials for administration to a subject.

Nucleic Acids

The present disclosure also features nucleic acids comprising nucleotide sequences that encode polypeptides (e.g., antibody molecules or fusion proteins), e.g., Fc regions of the polypeptides, as described herein.

For example, the present disclosure features a nucleic acid encoding an Fc region described herein, e.g., an Fc region comprising one or more of the mutations described herein. The Fc region can be engineered from an Fc region of an existing polypeptide (e.g., an antibody molecule or fusion protein) described herein. The nucleic acid can comprise a nucleotide sequence encoding an amino acid sequence of an Fc region of a polypeptide (e.g., antibody molecule or fusion protein) described herein, or a nucleotide sequence substantially identical thereto (e.g., a sequence at least about 85%, 90%, 95%, 99% or more identical thereto, and/or capable of hybridizing under the stringency conditions described herein).

In an embodiment, the nucleic acid further comprises a nucleotide sequence encoding a heavy chain variable region of a polypeptide (e.g., an antibody molecule or fusion protein) described herein, or having a nucleotide sequence substantially homologous thereto (e.g., a sequence at least about 85%, 90%, 95%, 99% or more identical thereto, and/or capable of hybridizing under the stringency conditions described herein). In another embodiment, the nucleic acid further comprises a nucleotide sequence encoding a light chain variable region of a polypeptide (e.g., an antibody molecule or fusion protein) described herein, or a nucleotide sequence substantially homologous thereto (e.g., a sequence at least about 85%, 90%, 95%, 99% or more identical thereto, and/or capable of hybridizing under the stringency conditions described herein). In yet another embodiment, the nucleic acid further comprises a nucleotide sequence encoding a heavy chain variable region and a light chain variable region of a polypeptide (e.g., an antibody molecule or fusion protein) described herein, or a nucleotide sequence substantially homologous thereto (e.g., a sequence at least about 85%, 90%, 95%, 99% or more identical thereto, and/or capable of hybridizing under the stringency conditions described herein).

In an embodiment, the nucleic acid further comprises a nucleotide sequence encoding at least one, two, or three CDRs from a heavy chain variable region of a polypeptide (e.g., an antibody molecule or fusion protein) described herein, or a nucleotide sequence substantially homologous thereto (e.g., a sequence at least about 85%, 90%, 95%, 99% or more identical thereto, and/or capable of hybridizing under the stringency conditions described herein). In another embodiment, the nucleic acid further comprises a nucleotide sequence encoding at least one, two, or three CDRs from a light chain variable region of a polypeptide (e.g., an antibody molecule or fusion protein) described herein, or a nucleotide sequence substantially homologous thereto (e.g., a sequence at least about 85%, 90%, 95%, 99% or more identical thereto, and/or capable of hybridizing under the stringency conditions described herein). In yet another embodiment, the nucleic acid comprises a nucleotide sequence encoding at least one, two, three, four, five, or six CDRs from heavy and light chain variable regions of a polypeptide (e.g., an antibody molecule or fusion protein) described herein, or a nucleotide sequence substantially homologous thereto (e.g., a sequence at least about 85%, 90%, 95%, 99% or more identical thereto, and/or capable of hybridizing under the stringency conditions described herein).

In an embodiment, the nucleic acid comprises a portion of a nucleotide sequence described herein. The portion may encode, for example, an Fc region, a variable region (e.g., VH or VL); one, two, or three or more (e.g., four, five, or six) CDRs; or one, two, three, or four or more framework regions.

The nucleic acids disclosed herein include deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

In some aspects, the application features host cells and vectors containing the nucleic acids described herein. The nucleic acids may be present in a single vector or separate vectors present in the same host cell or separate host cell, as described in more detail below.

Vectors

The present disclosure features vectors that comprise nucleotide sequences encoding polypeptides (e.g., an antibody molecules or fusion proteins), e.g., Fc regions of the polypeptides, as described herein.

For example, the present disclosure features a vector comprising a nucleotide sequence encoding an Fc region described herein, e.g., an Fc region comprising one or more of the mutations described herein. The Fc region can be engineered from an Fc region of an existing polypeptide (e.g., an antibody molecule or fusion protein) described herein. The vector can comprise a nucleotide sequence encoding an amino acid sequence of an Fc region of a polypeptide (e.g., antibody molecule or fusion protein) described herein, or a nucleotide sequence substantially identical thereto (e.g., a sequence at least about 85%, 90%, 95%, 99% or more identical thereto, and/or capable of hybridizing under the stringency conditions described herein).

The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the polypeptide (e.g., antibody molecule) produced are known to those skilled in the art, and may be varied or optimized depending upon the specific expression vector and mammalian host cell employed, based upon the present description.

Cells

The present disclosure also provides host cells comprising a nucleic acid encoding a polypeptide (e.g., an antibody molecule or fusion protein) as described herein. The polypeptide (e.g., antibody molecule or fusion protein) can be engineered in accordance with a method described herein. For example, the host cells may comprise a nucleic acid molecule having a nucleotide sequence of a polypeptide described herein (e.g., an antibody molecule or fusion protein described herein), a sequence substantially homologous thereto (e.g., a sequence at least about 85%, 90%, 95%, 99% or more identical thereto, and/or capable of hybridizing under the stringency conditions described herein), or a portion of one of said nucleic acids.

In some embodiments, the host cells are genetically engineered to comprise nucleic acids encoding the polypeptide (e.g., antibody molecule or fusion protein) described herein.

In certain embodiments, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

Uses of Polypeptides

The polypeptides (e.g., antibody molecules or fusion proteins) disclosed herein, as well as the pharmaceutical compositions disclosed herein, have in vitro, ex vivo, and in vivo therapeutic, prophylactic, and/or diagnostic utilities.

In an embodiment, the polypeptide (e.g., antibody molecule or fusion protein) modulates (e.g., reduces (e.g., inhibits, blocks, or neutralizes) or increases (e.g., activates, initiates, or enhances)) one or more biological activities of a target molecule (e.g., protein) or cell. For example, these polypeptides (e.g., antibody molecules or fusion proteins) can be administered to cells in culture, in vitro or ex vivo, or to a subject, e.g., a human subject, e.g., in vivo, to modulate one or more biological activities of the target molecule or cell. Accordingly, in an aspect, the disclosure provides a method of treating, preventing, or diagnosing a disorder, e.g., a disorder described herein, in a subject, comprising administering to the subject a polypeptide (e.g., an antibody molecule or fusion protein) described herein, such that the disorder is treated, prevented, or diagnosed. For example, the disclosure provides a method comprising contacting the polypeptide (e.g., antibody molecule or fusion protein) described herein with cells in culture, e.g. in vitro or ex vivo, or administering the polypeptide (e.g., antibody molecule or fusion protein) described herein to a subject, e.g., in vivo, to treat, prevent, or diagnose a disorder, e.g., a disorder associated with a target molecule or cell (e.g., a disorder described herein).

As used herein, the term "subject" is intended to include human and non-human animals. In some embodiments, the subject is a human subject, e.g., a human patient having a disorder described herein, or at risk of having a disorder described herein. The term "non-human animals" includes mammals and non-mammals, such as non-human primates. In an embodiment, the subject is a human. The methods and compositions described herein are suitable for treating human patients for a disorder described herein. Patients having a disorder described herein include those who have developed a disorder described herein but are (at least temporarily) asymptomatic, patients who have exhibited a symptom of a disorder described herein, or patients having a disorder related to or associated with a disorder described herein.

Methods of Treating or Preventing Disorders

The polypeptides (e.g., antibody molecules or fusion proteins) described herein can be used to treat or prevent disorders or conditions. In an embodiment, the polypeptide has an optimal or improved half-life, which can be desirable for treating or preventing the disorder or condition. While not wishing to be bound by theory, it is believed that in an embodiment, the polypeptide described herein (e.g., the polypeptide having an optimal or improved half-life) can provide one or more benefits over another polypeptide having the same or similar binding affinity and/or specificity (e.g., a polypeptide that does not have, or has not been engineered to have, an optimal or improved half-life). These benefits can include, but are not limited to, an increased therapeutic or preventive efficacy, a reduced dosage regimen, or an improved pharmacokinetic property. In an embodiment, the polypeptide includes a mutated Fc region as described herein.

Exemplary disorders or conditions that can be treated or prevented by the polypeptides described herein include, but are not limited to, a cancer (e.g., a solid tumor or a hematologic cancer), an infectious disease (e.g., a bacterial infection or a viral infection), an immune disorder (e.g., an autoimmune disorder), an inflammatory disorder, a metabolic disorder (e.g., diabetes), a cardiovascular disorder, an organ transplant rejection. In an embodiment, the disorder is a chronic disorder.

Exemplary cancers that can be treated or prevented by the polypeptides described herein include, but are not limited to, acute lymphoblastic leukemia (ALL), acute myeloid leukemia (AML), adrenocortical carcinoma, Kaposi sarcoma, an AIDS-related lymphoma, primary central nervous system (CNS) lymphoma, anal cancer, appendix cancer, astrocytoma, atypical teratoid/rhabdoid tumor, basal cell carcinoma, bile duct cancer, bladder cancer, bone cancer (e.g., Ewing sarcoma or osteosarcoma and malignant fibrous histiocytoma), brain tumor (e.g., astrocytomas, brain stem glioma, central nervous system atypical teratoid/rhabdoid tumor, central nervous system embryonal tumor, central nervous system germ cell tumor, craniopharyngioma, or ependymoma), breast cancer, bronchial tumor, Burkitt lymphoma, carcinoid tumor (e.g., gastrointestinal carcinoid tumor), cardiac (heart) tumor, embryonal tumor, germ cell tumor, lymphoma, cervical cancer, cholangiocarcinoma, chordoma, chronic lymphocytic leukemia (CLL), chronic myelogenous leukemia (CML), chronic myeloproliferative neoplasm, colon cancer, colorectal cancer, craniopharyngioma, cutaneous T-cell lymphoma, ductal carcinoma in situ (DCIS), endometrial cancer, ependymoma, esophageal cancer, esthesioneuroblastoma, Ewing sarcoma, extracranial germ cell tumor, extragonadal germ cell tumor, eye cancer (e.g., intraocular melanoma or retinoblastoma), fallopian tube cancer, fibrous histiocytoma of bone, osteosarcoma, gallbladder cancer, gastric (stomach) cancer, gastrointestinal carcinoid tumor, gastrointestinal stromal tumors (GIST), germ cell tumor (e.g., central nervous system tumor, extracranial tumor, extragonadal tumor, ovarian cancer, or testicular cancer), gestational trophoblastic disease, glioma, hairy cell leukemia, head and neck cancer, hepatocellular (liver) cancer, Hodgkin lymphoma, hypopharyngeal cancer, intraocular melanoma, islet cell tumor, pancreatic neuroendocrine tumor, Kaposi sarcoma, kidney cancer (e.g., renal cell cancer or Wilms tumor), Langerhans cell histiocytosis (LCH), laryngeal cancer, leukemia (e.g., acute lymphoblastic leukemia (ALL), acute myeloid leukemia (AML), chronic lymphocytic leukemia (CLL), chronic myelogenous leukemia (CML), or hairy cell leukemia), lip and oral cavity cancer, liver cancer, lung cancer (e.g., non-small cell lung cancer (NSCLC) or small cell lung cancer), lymphoma (e.g., aids-related, Burkitt lymphoma, cutaneous T-cell lymphoma, Hodgkin lymphoma, non-Hodgkin lymphoma, or primary central nervous system (CNS) lymphoma), Waldenström macroglobulinemia, male breast cancer, malignant fibrous histiocytoma of bone and osteosarcoma, melanoma (e.g., intraocular (eye) melanoma), Merkel cell carcinoma, mesothelioma, metastatic squamous neck cancer, midline tract carcinoma, mouth cancer, multiple endocrine neoplasia syndrome, multiple myeloma/plasma cell neoplasm, mycosis fungoides, myelodysplastic syndrome, myelodysplastic/ myeloproliferative neoplasm, chronic myeloproliferative neoplasm, nasal cavity and paranasal sinus cancer, nasopharyngeal cancer, neuroblastoma, oral cancer, lip and oral cavity cancer, oropharyngeal cancer, osteosarcoma and malignant fibrous histiocytoma of bone, ovarian cancer (e.g., epithelial ovarian cancer or germ cell ovarian tumor), pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, pleuropulmonary blastoma, peritoneal cancer, prostate cancer, rectal cancer, retinoblastoma, rhabdomyosarcoma, salivary gland cancer, sarcoma (e.g., Ewing sarcoma, Kaposi sarcoma, osteosarcoma, rhabdomyosarcoma, soft tissue sarcoma, or uterine sarcoma), Sézary syndrome, skin cancer (e.g., melanoma, Merkel cell carcinoma, or nonmelanoma skin cancer), small intestine cancer, squamous cell carcinoma, testicular cancer, throat cancer, thymoma and thymic carcinoma, thyroid cancer, transitional cell cancer of the renal pelvis and ureter, urethral cancer, endometrial uterine cancer, vaginal cancer, vulvar cancer, or a metastatic lesion thereof.

Exemplary infectious diseases that can be treated or prevented by the polypeptides described herein include, but are not limited to, *Acinetobacter* infections, actinomycosis, African sleeping sickness (African trypanosomiasis), AIDS (acquired immunodeficiency syndrome), amebiasis, anaplasmosis, angiostrongyliasis, anisakiasis, anthrax, *arcanobacterium haemolyticum* infection, argentine hemorrhagic fever, ascariasis, aspergillosis, astrovirus infection, babesiosis, *Bacillus cereus* infection, bacterial pneumonia, bacterial vaginosis, *bacteroides* infection, balantidiasis, bartonellosis, *Baylisascaris* infection, bk virus infection, black piedra, blastocystosis, blastomycosis, bolivian hemorrhagic fever, botulism (and infant botulism), brazilian hemorrhagic fever, brucellosis, bubonic plague, *burkholderia* infection, buruli ulcer, calicivirus infection (norovirus and sapovirus), campylobacteriosis, candidiasis (moniliasis; thrush), capillariasis, carrion's disease, cat-scratch disease, cellulitis, chagas disease (american trypanosomiasis), chancroid, chickenpox, chikungunya, *chlamydia, chlamydophila pneumoniae* infection (taiwan acute respiratory agent or twar), cholera, chromoblastomycosis, chytridiomycosis, clonorchiasis, *Clostridium difficile* colitis, coccidioidomycosis, colorado tick fever (CTF), common cold (Acute viral rhinopharyngitis; Acute coryza), Creutzfeldt-Jakob disease (CJD), Crimean-Congo hemorrhagic fever (CCHF), cryptococcosis, cryptosporidiosis, cutaneous larva migrans (CLM), cyclosporiasis, cysticercosis, cytomegalovirus infection, dengue fever, desmodesmus infection, dientamoebiasis, diphtheria, diphyllobothriasis, dracunculiasis, ebola hemorrhagic fever, echinococcosis, ehrlichiosis, enterobiasis (pinworm infection), *enterococcus* infection, enterovirus infection, epidemic typhus, erythema infectiosum (fifth disease), exanthem subitum (sixth disease), fasciolasis, fasciolopsiasis, fatal familial insomnia (FFI), filariasis, food poisoning by *Clostridium perfringens*, free-living amebic infection, *fusobacterium* infection, gas gangrene (clostridial myonecrosis), geotrichosis, gerstmann-straussler-scheinker syndrome (GSS), giardiasis, glanders, gnathostomiasis, gonorrhea, granuloma inguinale (donovanosis), Group A streptococcal infection, Group B streptococcal infection, *Haemophilus influenzae* infection, hand, foot and mouth disease (HFMD), Hantavirus Pulmonary Syndrome (HPS), heartland virus disease, *Helicobacter pylori* infection, hemolytic-uremic syndrome (HUS), hemorrhagic fever with renal syndrome (HFRS), hepatitis A, hepatitis B, hepatitis C, hepatitis D, hepatitis E, herpes simplex, histoplasmosis, hookworm infection, human bocavirus infection, human *ewingii* ehrlichiosis, human granulocytic anaplasmosis (HGA), human metapneumovirus infection, Human monocytic ehrlichiosis, human papillomavirus (HPV) infection, Human parainfluenza virus infection, Hymenolepiasis, Epstein-Barr Virus Infectious Mononucleosis (Mono), influenza (flu), isosporiasis, kawasaki disease, keratitis, kingella kingae infection, kuru, lassa fever, legionellosis (legionnaires' disease), legionellosis (pontiac fever), leishmaniasis, leprosy, leptospirosis, listeriosis, lyme disease (lyme borreliosis), lymphatic filariasis (Elephantiasis), Lymphocytic choriomeningitis, Malaria, Marburg hemorrhagic fever (MHF), Measles, Middle East respiratory syndrome (MERS), melioidosis (Whitmore's disease), meningitis, meningococcal disease, metagonimiasis, microsporidiosis, molluscum contagiosum (MC), Monkeypox, Mumps, Murine typhus (Endemic typhus), *Mycoplasma* pneumonia, Mycetoma (disambiguation), Myiasis, Neonatal conjunctivitis (Ophthalmia neonatorum), (New) Variant Creutzfeldt-Jakob disease (vCJD, nvCJD), nocardiosis, onchocerciasis (River blindness), opisthorchiasis, paracoccidioidomycosis (South American blastomycosis), paragonimiasis, pasteurellosis, pediculosis capitis (head lice), pediculosis corporis (body lice), pediculosis pubis (pubic lice, crab lice), pelvic inflammatory disease (PID), pertussis (Whooping cough), plague, pneumococcal infection, *pneumocystis* pneumonia (PCP), pneumonia, poliomyelitis, *prevotella* infection, primary amoebic meningoencephalitis (PAM), progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley fever (RVF), Rocky Mountain spotted fever (RMSF), rotavirus infection, rubella, salmonellosis, SARS (Severe Acute Respiratory Syndrome), scabies, schistosomiasis, sepsis, shigellosis (Bacillary dysentery), shingles (Herpes zoster), smallpox (Variola), sporotrichosis, staphylococcal food poisoning, staphylococcal infection, strongyloidiasis, subacute sclerosing panencephalitis, syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manum (Ringworm of the Hand), Tinea nigra, Tinea pedis (Athlete's foot), Tinea unguium (Onychomycosis), *Tinea versicolor* (*Pityriasis versicolor*), Toxocariasis (Ocular Larva Migrans (OLM)), Toxocariasis (Visceral Larva Migrans (VLM)), Trachoma, Toxoplasmosis, Trichinosis, Trichomoniasis, Trichuriasis (Whipworm infection), Tuberculosis, Tularemia, Typhoid fever, Typhus fever, *Ureaplasma urealyticum* infection, Valley fever, Venezuelan equine encephalitis, Venezuelan hemorrhagic fever, *Vibrio vulnificus* infection, *Vibrio parahaemolyticus* enteritis, viral pneumonia, West Nile Fever, white piedra (*Tinea blanca*), *Yersinia pseudotuberculosis* infection, yersiniosis, yellow fever, Zika fever, or zygomycosis.

Exemplary immune disorders or conditions that can be treated or prevented by the polypeptides described herein include, but are not limited to, Addison's disease, agammaglobulinemia, alopecia areata, amyloidosis, ankylosing spondylitis, anti-GBM/anti-TBM nephritis, antiphospholipid syndrome (APS), autoimmune hepatitis, autoimmune inner ear disease (AIED), axonal & neuronal neuropathy (AMAN), Behcet's disease, Bullous pemphigoid, Castleman disease (CD), Celiac disease, Chagas disease, chronic inflammatory demyelinating polyneuropathy (CIDP), chronic recurrent multifocal osteomyelitis (CRMO), Churg-Strauss, Cicatricial pemphigoid/benign mucosal pemphigoid, Cogan's syndrome, Cold agglutinin disease, Congenital heart block, Coxsackie myocarditis, CREST syndrome, Crohn's disease, dermatitis herpetiformis, dermatomyositis, Devic's disease (neuromyelitis optica), Discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, fibrosing alveolitis, giant cell arteritis (temporal arteritis), giant cell myocarditis, Glomerulonephritis, Goodpasture's syndrome, Granulomatosis with Polyangiitis, Graves' disease, Guillain-Barre syndrome, Hashimoto's thyroiditis, hemolytic anemia, Henoch-Schonlein purpura (HSP), herpes gestationis or pemphigoid gestationis (PG), hypogammalglobulinemia, IgA nephropathy, IgG4-related sclerosing disease, inclusion body myositis (IBM), interstitial cystitis (IC), juvenile arthritis, juvenile diabetes (Type 1 diabetes), juvenile myositis (JM), Kawasaki disease, Lambert-Eaton syndrome, leukocytoclastic vasculitis, Lichen planus, Lichen sclerosus, Ligneous conjunctivitis, linear IgA disease (LAD), lupus, Lyme disease chronic, Meniere's disease, microscopic polyangiitis (MPA), mixed connective tissue disease (MCTD), Mooren's ulcer, Mucha-Habermann disease, multiple sclerosis (MS), Myasthenia gravis, Myositis, Narcolepsy, Neuromyelitis optica, neutropenia, ocular cicatricial pemphigoid, optic neuritis, palindromic rheumatism (PR), PANDAS (Pediatric Autoimmune Neuropsychiatric Disorders Associated with *Streptococcus*), paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, peripheral neuropathy, Perivenous encephalomyelitis, pernicious anemia (PA), POEMS syndrome (polyneuropathy, organomegaly, endocrinopathy, monoclonal gammopathy, skin changes), polyarteritis nodosa, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, Reactive Arthritis, Reflex sympathetic dystrophy, Reiter's syndrome, relapsing polychondritis, restless legs syndrome (RLS), retroperitoneal fibrosis, rheumatic fever, rheumatoid arthritis (RA), sarcoidosis, Schmidt syndrome, scleritis, scleroderma, Sjogren's syndrome, sperm & testicular autoimmunity, Stiff person syndrome (SPS), subacute bacterial endocarditis (SBE), Susac's syndrome, sympathetic ophthalmia (SO), Takayasu's arteritis, temporal arteritis/Giant cell arteritis, thrombocytopenic purpura (TTP), Tolosa-Hunt syndrome (THS), transverse myelitis, type 1 diabetes, ulcerative colitis (UC), undifferentiated connective tissue disease (UCTD), uveitis, vasculitis, vitiligo, or Wegener's granulomatosis (Granulomatosis with Polyangiitis (GPA)).

The polypeptides (e.g., antibody molecules or fusion proteins) described herein are typically administered at a frequency that keeps a therapeutically effective level of polypeptides in the patient's system until the patient recovers. For example, the polypeptides may be administered at a frequency that achieves a serum concentration sufficient for at least about 1, 2, 5, 10, 20, 30, or 40 polypeptides to bind each target molecule or cell. In an embodiment, the polypeptides are administered every 1, 2, 3, 4, 5, 6, or 7 days, every 1, 2, 3, 4, 5, or 6 weeks, or every 1, 2, 3, 4, 5, or 6 months.

Methods of administering various polypeptides (e.g., antibody molecules or fusion proteins) are known in the art and are described below. Suitable dosages of the polypeptides used will depend on the age and weight of the subject and the particular drug used.

The polypeptides can be used by themselves or conjugated to a second agent, e.g., an bacterial agent, toxin, or protein, e.g., a second polypeptide. This method includes: administering the polypeptide, alone or conjugated to a second agent, to a subject requiring such treatment. The polypeptides can be used to deliver a variety of therapeutic agents, e.g., a toxin, or mixtures thereof.

Combination Therapies

The polypeptides (e.g., antibody molecules or fusion proteins) can be used in combination with other therapies. For example, the combination therapy can include a polypeptide co-formulated with, and/or co-administered with, one or more additional therapeutic agents, e.g., one or more additional therapeutic agents described herein. In other embodiments, the polypeptides are administered in combination with other therapeutic treatment modalities, e.g., other therapeutic treatment modalities described herein. Such combination therapies may advantageously utilize lower dosages of the administered therapeutic agents, thus avoiding possible toxicities or complications associated with the various monotherapies.

Administered "in combination", as used herein, means that two (or more) different treatments are delivered to the subject before, or during the course of the subject's affliction with a disorder. In an embodiment, two or more treatments are delivered prophylactically, e.g., before the subject has the disorder or is diagnosed with the disorder. In another embodiment, the two or more treatments are delivered after the subject has developed or diagnosed with the disorder. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In an embodiment, the polypeptide is administered in combination with a second therapy (e.g., an additional agent) to treat or prevent a disorder described herein. In an embodiment, the additional agent is a second polypeptide (e.g., antibody molecule), e.g., a polypeptide (e.g., an antibody molecule) different from a first polypeptide (e.g., antibody molecule). Exemplary polypeptides (e.g., antibody molecules) that can be used in combination include, but are not limited to, any combination of the polypeptides (e.g., antibody molecules) described herein. In another embodiment, the additional agent is other than a polypeptide (e.g., antibody molecule). For example, the additional agent can be a small molecule or a nucleic acid molecule. In yet another embodiment, the second therapy is chosen from a surgery, a radiation therapy, a cell therapy (e.g., a stem cell therapy), or an organ or tissue transplantation.

In an embodiment, the second therapy comprises a therapy chosen from one or more of: an androgen replacement therapy, an antihormone therapy, an antiserum therapy, an autologous immune enhancement therapy, a biotherapy, a blood irradiation therapy, a brachytherapy, a cardiac resynchronization therapy, a cell therapy, a cell transfer therapy, a chelation therapy, a chemotherapy, a chrysotherapy, a cobalt therapy, a cold compression therapy, a cryotherapy, an electroconvulsive therapy, an electromagnetic therapy, an electron therapy, an electrotherapy, an enzyme replacement therapy, an epigenetic therapy, an estrogen replacement therapy, an extracorporeal shockwave therapy, a fast neutron therapy, a fluoride therapy, a gene therapy, a heat therapy, a helminthic therapy, a hormone therapy, a hormone replacement therapy, a host modulatory therapy, a hyperbaric oxygen therapy, a hyperthermia therapy, an immunosuppressive therapy, an immunotherapy, an intraoperative electron radiation therapy, an intraoperative radiation therapy, an inversion therapy, a laser therapy, a light therapy, a lithium therapy, a low level laser therapy, a magnet therapy, a magnetic resonance therapy, a medical gas therapy, a medical nutrition therapy, a molecular chaperone therapy, a molecular therapy, a monoclonal antibody therapy, a negative air ionization therapy, a neutron capture therapy, a neutron therapy, an oral rehydration therapy, an osmotherapy, an oxygen therapy, an ozone therapy, a palliative therapy, a particle therapy, a phage therapy, a phonemic neurological hypochromium therapy, a photodynamic therapy, a phototherapy, a photothermal therapy, a physical therapy, a prolotherapy, a protein therapy, a proton therapy, a pulsed electromagnetic field therapy, a PUVA therapy, a radiation therapy, a rehydration therapy, a respiratory therapy, salvage therapy, a serotherapy, a stem cell therapy, a stereotactic radiation therapy, a targeted therapy, a thermotherapy, a TK cell therapy, a tolerogenic therapy, a transdermal continuous oxygen therapy, an ultraviolet light therapy, or a virotherapy.

Exemplary therapies that can be used in combination with a polypeptide or composition described herein to treat or prevent other disorders are also described in the section of "Methods of Treating or Preventing Disorders" herein.

Methods of Diagnosis

In some aspects, the present disclosure provides a diagnostic method for detecting the presence of a target molecule (e.g., a protein) or cell in vitro (e.g., in a biological sample, such as a biopsy or body fluid (e.g., blood, urine, or cerebrospinal fluid) sample) or in vivo (e.g., in vivo imaging in a subject). The method includes: (i) contacting the sample with a polypeptide described herein (e.g., an antibody molecule described herein), or administering to the subject, the polypeptide (e.g., antibody molecule); (optionally) (ii) contacting a reference sample, e.g., a control sample (e.g., a control biological sample, such as a biopsy or body fluid (e.g., blood, urine, or cerebrospinal fluid) sample) or a control subject with a polypeptide described herein (e.g., an antibody molecule described herein); and (iii) detecting formation of a complex between the polypeptide (e.g., antibody molecule) and the target molecule or cell in the sample or subject, or the control sample or subject, wherein a change, e.g., a statistically significant change, in the formation of the complex in the sample or subject relative to the control sample or subject is indicative of the presence of the target molecule or cell in the sample. The polypeptide (e.g., antibody molecule) can be directly or indirectly labeled with a detectable substance to facilitate detection of the bound or unbound polypeptide (e.g., antibody molecule). Suitable detectable substances include various enzymes, prosthetic groups, fluorescent materials, luminescent materials and radioactive materials, as described herein.

The term "sample," as it refers to samples used for detecting bacteria includes, but is not limited to, cells, cell lysates, proteins or membrane extracts of cells, body fluids such as blood, urine, or CSF, or tissue samples such as biopsies.

Complex formation between the polypeptide (e.g., antibody molecule), and the target molecule or cell, can be detected by measuring or visualizing either the polypeptide (e.g., antibody molecule) bound to the target molecule or cell, or unbound polypeptide (e.g., antibody molecule). Any suitable detection assays can be used, and conventional detection assays include an enzyme-linked immunosorbent assays (ELISA), a radioimmunoassay (RIA) or tissue immunohistochemistry. Alternative to labeling the polypeptide, the presence of the target molecule or cell can be assayed in a sample by a competition immunoassay utilizing standards labeled with a detectable substance and an unlabeled polypeptide. In this assay, the biological sample, the labeled standards and the polypeptide are combined and the amount of labeled standard bound to the unlabeled binding molecule is determined. The amount of the target molecule or cell in the sample is inversely proportional to the amount of labeled standard bound to the polypeptide (e.g., antibody molecule).

The polypeptides (e.g., antibody molecules) described herein can be used to diagnose disorders that can be treated or prevented by the polypeptides described herein. The detection or diagnostic methods described herein can be used in combination with other methods described herein to treat or prevent disorders described herein.

The present disclosure also includes any of the following numbered paragraphs:

1. A polypeptide comprising an Fc region, wherein the Fc region comprises a mutation, wherein the polypeptide has 3, 4, 5, 6, 7, 8, 9, 10, 11, 12, 13, or all of the following properties:
  a) has an increased binding affinity for a neonatal Fc receptor (FcRn) at a pH between 6.0 and 6.5, compared to a reference polypeptide;
  b) has a higher binding affinity for FcRn at a pH between 6.0 and 6.5 than the binding affinity at a pH between 7.0 and 7.4;
  c) binds to an FcRn at a pH between 6.0 and 6.5 with a dissociation constant ($K_d$) of 300 nM or less;
  d) binds to the FcRn at a pH between 7.0 and 7.4 with a $K_d$ of 50 nM or more;
  e) has the same, substantially the same, or increased binding affinity for an Fcγ receptor, compared to a reference polypeptide;
  f) has the same, or substantially the same, thermal stability, compared to a reference polypeptide;
  g) has the same, substantially the same, or increased binding affinity for C1q, compared to a reference polypeptide;
  h) has the same, substantially the same, or increased binding affinity for TRIM21, compared to a reference polypeptide.
  i) has an effector function that is the same, substantially the same, or increased, compared to a reference polypeptide;
  j) has an increased half-life in vivo, compared to a reference polypeptide;
  k) has a biological function, in vitro, ex vivo, or in vivo, that is the same, substantially the same, or increased, compared to a reference polypeptide;
  l) has a developability characteristic that is the same or substantially the same, compared to a reference polypeptide;
  m) has the same, substantially the same, or increased binding affinity, specificity, or both, for an epitope, compared to a reference polypeptide; or
    n) increases mucosal uptake, compared to a reference polypeptide, and
    wherein the polypeptide has at least properties a), b), and one, two, three, four, or all of properties e), f), g), h), or i).
2. The polypeptide of paragraph 1, which has at least properties a), b), c), d), and one, two, three, four, or all of properties e), f), g), h), or i).
3. The polypeptide of paragraph 1 or 2, which has at least properties a), b), one, two, three, four, or all of properties e), f), g), h), or i), and one, two, three, four, five, six, or all of properties c), d), j), k), l), m), or n).
4. The polypeptide of any of paragraphs 1-3, which has at least 1.5, 2, 3, 4, 5, 6, 7, 8, 9, 10, 15, 20, 30, 40, or 50-fold increase in the binding affinity for the FcRn at pH 6.0, compared to a reference polypeptide, as determined by an octet-based assay or a cell-based assay.
5. The polypeptide of any of paragraphs 1-4, which has at least 1.5, 2, 3, 4, 5, 6, 7, 8, 9, 10, 15, 20, or 50-fold higher in the binding affinity for the FcRn at pH 6.0 than that at pH 7.4, as determined by an octet-based assay or a cell-based assay.
6. The polypeptide of any of paragraphs 1-5, which binds to the FcRn at pH 6.0 with a dissociation constant ($K_d$) of 250 nM or less, 200 nM or less, 150 nM or less, 100 nM or less, 50 nM or less, 25 nM or less, 10 nM or less, 5 nM or less, 2 nM or less, 1 nM or less, 0.5 nM or less, 0.2 nM or less, 0.1 nM or less, 0.05 nM or less, 0.02 nM or less, 0.01 nM or less, between 25 nM and 0.1 nM, between 20 nM and 0.5 nM, between 15 nM and 1 nM, between 10 nM and 5 nM, or between 20 nM and 10 nM, as determined by an octet-based assay or a cell-based assay.
7. The polypeptide of any of paragraphs 1-6, which binds to the FcRn at pH 7.4 with a $K_d$ of 60 nM or more, 80 nM or more, 100 nM or more, 150 nM or more, 200 nM or more, 500 nM or more, between 50 nM and 500 nM, or between 100 nM and 250 nM, as determined by an octet-based assay or a cell-based assay.
8. The polypeptide of any of paragraphs 1-7, which decreases the binding affinity for one, two, or, all of FcγRI, FcγRIIa/b, or FcγRIII by no more than 10%, 20%, 30%, 40%, or 50%, or increases the binding affinity for one, two, or all of FcγRI, FcγRIIa/b, or FcγRIII by at least 1.5, 2, 3, 4, or 5-fold, compared to a reference polypeptide, as determined by an octet-based assay or a cell-based assay.
9. The polypeptide of any of paragraphs 1-8, which increases or decreases the melting temperature by no more than 1° C., 2° C., 3° C., 4° C., 5° C., 6° C., 7° C., 8° C., 9° C., or 10° C., compared to a reference polypeptide, as determined by a sypro orange assay.
10. The polypeptide of any of paragraphs 1-9, which decreases the binding affinity for C1q by no more than 10%, 20%, 30%, 40%, or 50%, or increases the binding affinity for C1q by at least 1.5, 2, 3, 4, or 5-fold, compared to a reference polypeptide, as determined by ELISA.
11. The polypeptide of any of paragraphs 1-10, which decreases the binding affinity for TRIM21 by no more than 10%, 20%, 30%, 40%, or 50%, or increases the binding affinity for TRIM21 by at least 1.5, 2, 3, 4, or 5-fold, compared to a reference polypeptide, as determined by ELISA.
12. The polypeptide of any of paragraphs 1-11, which decreases one, two, three, or all of a complement dependent cytotoxicity (CDC), an antibody dependent cell mediated cytotoxicity (ADCC), an antibody dependent cell mediated phagocytosis (ADCP), or an antibody dependent intracellular neutralization (ADIN) by no more than 10%, 20%, 30%, 40%, or 50%, or increases one, two, three, or all of a complement dependent cytotoxicity (CDC), an antibody dependent cell mediated cytotoxicity (ADCC), an antibody dependent cell mediated phagocytosis (ADCP), or an antibody dependent intracellular neutralization (ADIN) by at least 1.5, 2, 3, 4, or 5-fold, compared to a reference polypeptide.
13. The polypeptide of any of paragraphs 1-12, which has at least 1.5, 2, 3, 4, 5, 6, 7, 8, 9, or 10-fold increase in the half-life in vivo, compared to a reference polypeptide, as determined in an animal model.
14. The polypeptide of any of paragraphs 1-13, which decreases the biological function, in vitro, ex vivo, or in vivo by no more than 10%, 20%, 30%, 40%, or 50%, or increases the biological function, in vitro, ex vivo, or in vivo by at least 1.5, 2, 3, 4, or 5-fold, compared to a reference polypeptide.
15. The polypeptide of any of paragraphs 1-14, which alters one, two, three, or all of stability, solubility, aggregation, or expression level by no more than 10%, 20%, 30%, 40%, or 50%, compared to a reference polypeptide.
16. The polypeptide of any of paragraphs 1-15, which decreases the binding affinity, specificity, or both by no more than 10%, 20%, 30%, 40%, or 50%, or increases the binding affinity, specificity, or both by at least 1.5, 2, 3, 4, or 5-fold, compared to a reference polypeptide.
17. The polypeptide of any of paragraphs 1-16, which increases mucosal uptake by at least 1.5, 2, 3, 4, 5, 6, 7, 8, 9, or 10-fold, compared to a reference polypeptide, as determined by a transcytosis assay.

18. The polypeptide of any of paragraphs 1-4 or 8-17, wherein the reference polypeptide comprises a wild-type Fc region, an Fc region comprising the amino acid sequence of SEQ ID NO: 1, or an amino acid sequence at least about 85%, 90%, 95%, 99% or more identical thereto, or which differs by no more than 1, 2, 5, 10, or 15 amino acid residues.

19. The polypeptide of any of paragraphs 1-18, wherein the mutation is in a residue in a CH2 domain.

20. The polypeptide of any of paragraphs 1-18, wherein the mutation is in a residue in a CH3 domain.

21. The polypeptide of any of paragraphs 1-20, comprising at least one mutation in a residue in a CH2 domain and at least one mutation in a residue in a CH3 domain.

22. The polypeptide of any of paragraphs 1-21, further comprising a mutation in a residue in a region other than a CH2 domain and/or a CH3 domain.

23. The polypeptide of any of paragraphs 1-22, wherein the mutation does not alter, or does not substantially alter, the conformation of the linker region between a CH2 domain and a CH3 domain.

24. The polypeptide of any of paragraphs 1-23, wherein the mutation does not introduce 3, 4, 5, 6, 7, 8, 9, 10, or more consecutive hydrophobic or aromatic residues on a surface region.

25. The polypeptide of any of paragraphs 1-24, which comprises an antibody molecule.

26. The polypeptide of any of paragraphs 1-25, which comprises an IgG.

27. The polypeptide of any of paragraphs 1-26, which comprises an IgG1, IgG2, IgG3, or IgG4.

28. The polypeptide of any of paragraphs 1-27, which comprises a heavy chain immunoglobulin variable region, a light chain immunoglobulin variable region, or both.

29. The polypeptide of any of paragraphs 1-28, which comprises a tetramer of two heavy chain immunoglobulin variable regions and two light chain immunoglobulin variable regions.

30. The polypeptide of any of paragraphs 1-29, which comprises a full length antibody molecule.

31. The polypeptide of any of paragraphs 1-30, which comprises a fragment of an antibody molecule.

32. The polypeptide of any of paragraphs 1-31, which comprises a chimeric antibody molecule or a murine antibody molecule.

33. The polypeptide of any of paragraphs 1-32, which comprises a human antibody molecule or a humanized antibody molecule.

34. The polypeptide of any of paragraphs 1-24, which comprises a fusion protein.

35. The polypeptide of any of paragraphs 1-34, comprising 1, 2, 3, 4, or all of the following:
   (i) a mutation in a residue in a surface region that interacts with FcRn;
   (ii) a mutation in a residue that is a peripheral residue along the Fc-FcRn interface;
   (iii) a mutation is in a residue that is non-contact residue in Fc-FcRn binding;
   (iv) a mutation in a residue which is a helix contact reside that enhances the conformational dynamics of a helix comprising 1, 2, 3, 4, 5, or all of P247, K248, D249, T250, L251, or M252; or
   (v) a mutation, which modulates pK of a histidine or is an introduction of a histidine along the Fc-FcRn interface.

36. The polypeptide of any of paragraphs 1-35, comprising a mutation in a residue in a surface region that interacts with FcRn.

37. The polypeptide of paragraph 36, wherein the mutation is in a residue chosen from: L251, I253, R255, P257, H285, N286, K288, T307, V308, L309, Q311, L314, H310, H433, N434, H435, or Y436.

38. The polypeptide of any of paragraphs 1-37, comprising a plurality of mutations in 2, 3, 4, 5, 6, 7, 8, 9, 10, 11, 12, 13, 14, 15, 16, or all of the residues chosen from L251, I253, R255, P257, H285, N286, K288, T307, V308, L309, Q311, L314, H310, H433, N434, H435, or Y436.

39. The polypeptide of any of paragraphs 1-38, comprising a mutation in a residue that is a peripheral residue along the Fc-FcRn interface.

40. The polypeptide of paragraph 39, wherein the mutation is in a residue chosen from M252, T256, T307, L309, Q311, H433, N434, Y436, N286, or K288.

41. The polypeptide of any of paragraphs 1-40, comprising a plurality of mutations in 2, 3, 4, 5, 6, 7, 8, 9, or all of the residues chosen from M252, T256, T307, L309, Q311, H433, N434, Y436, N286, or K288.

42. The polypeptide of any of paragraphs 1-41, comprising a mutation is in a residue that is non-contact residue in Fc-FcRn binding.

43. The polypeptide of paragraph 42, wherein the mutation is in a residue chosen from A287, V308, N315, L314, L432, H429, E430, or A431.

44. The polypeptide of any of paragraphs 1-43, comprising a plurality of mutations in 2, 3, 4, 5, 6, 7, or all of the residues chosen from A287, V308, N315, L314, L432, H429, E430, or A431.

45. The polypeptide of any of paragraphs 1-44, comprising a mutation in a residue which is a helix contact reside that enhances the conformational dynamics of a helix comprising 1, 2, 3, 4, 5, or all of P247, K248, D249, T250, L251, or M252.

46. The polypeptide of paragraph 45, wherein the mutation is in a residue chosen from P244, P245, T250, L251, P247, E380, M428, A378, D376, P257, V308, A287, L306, or H427.

47. The polypeptide of any of paragraphs 1-46, comprising a plurality of mutations in 2, 3, 4, 5, 6, 7, 8, 9, 10, 11, 12, 13, or all of the residues chosen from P244, P245, T250, L251, P247, E380, M428, A378, D376, P257, V308, A287, L306, or H427.

48. The polypeptide of any of paragraphs 1-47, comprising a mutation which is the introduction of a histidine along the Fc-FcRn interface.

49. The polypeptide of any of paragraphs 1-48, comprising 1, 2, 3, 4, 5, 6, 7, 8, 9, 10, or more mutations, or one or more combination of mutations, as described in Table 1.

50. The polypeptide of any of paragraphs 1-49, wherein the mutation is other than M252Y, S254T, T256E, L309N, T250Q, M428L, N434S, N434A, T307A, E380A, N434A, M252Y, S254T, T256E, or a combination thereof.

51. The polypeptide of any of paragraphs 1-50, wherein the mutation is in a residue other than residue M252Y, S254T, T256E, L309N, T250, M428, N434, N434, T307, E380, N434, M252, S254, T256, or a combination thereof.

52. The polypeptide of any of paragraphs 1-51, which does not have 1, 2, 3, 4, 5, 6, 7, 8, 9, or all of the following mutation or mutations: (i) M252Y, S254T, and T256E; (ii) L309N; (iii) T250Q and M428L; (iv) M428L and N434A; (v) N434A; (vi) T307A, E380A, and N434A; (vii) M252W; (viii) V308F; (ix) V308F and N434Y; or (x) H435A.

53. The polypeptide of any of paragraphs 1-52, comprising a first mutation chosen from M252Y, S254T, T256E, L309N, T250Q, M428L, N434S, N434A, T307A, E380A, N434A, M252Y, S254T, or T256E, and a second mutation chosen from a mutation in Table 1 other than M252Y, S254T, T256E, L309N, T250Q, M428L, N434S, N434A, T307A, E380A, N434A, M252Y, S254T, and T256E.

54. The polypeptide of any of paragraphs 1-53, further comprising a mutation in the Fc region that increases an effector function.

55. The polypeptide of paragraph 54, wherein the mutation is in a residue chosen from S239, A330, I332, F243, G236, or a combination thereof.

56. The polypeptide of any of paragraphs 1-55, further comprising a mutation in the Fc region that decreases an effector function.

57. The polypeptide of paragraph 56, wherein the mutation is in a residue chosen from K322, L234, L235, P331, N297, or a combination thereof.

58. The polypeptide of any of paragraphs 1-57, wherein the Fc region comprises:
(a) 1, 2, 3, 4, 5, or all of the combinations of mutations chosen from: T256D/Q311V/A378V, H285N/T307Q/N315D, H285D/T307Q/A378V, T307Q/Q311V/A378V, T256D/N286D/T307R/Q311V/A378V, or T256D/T307R/Q311V;
(b) a mutation or a combination of mutations capable of disrupting an Fc effector function, or
(c) both (a) and (b).

59. The polypeptide of any of paragraphs 1-58, which comprises mutations in residues chosen from: (i) T256, Q311, and A378; (ii) H285, T307, and N315; (iii) H285, T307, and A378; (iv) T307, Q311, and A378; (v) T256, N286, T307, Q311, and A378; or (vi) T256, H285, T307, Q311, and A378.

60. The polypeptide of any of paragraphs 1-59, which comprises mutations chosen from: (i) T256D, Q311V, and A378V; (ii) H285N, T307Q, and N315D; (iii) H285D, T307Q, and A378V; (iv) T307Q, Q311V, and A378V; (v) T256D, N286D, T307R, Q311V, and A378V; or (vi) T256D, H285D, T307R, Q311V, and A378V.

61. The polypeptide of any of paragraphs 1-60, further comprising a mutation in a region other than the Fc region.

62. The polypeptide of any of paragraphs 1-61, comprising a plurality of mutations, wherein at least one mutation is a compensating or beneficial mutation.

63. The polypeptide of any of paragraphs 1-62, which is an isolated polypeptide.

64. The polypeptide of any of paragraphs 1-62, which is a synthetic polypeptide.

65. A composition comprising a polypeptide of any of paragraphs 1-64.

66. The composition of paragraph 65, further comprising a pharmaceutical acceptable carrier.

67. A nucleic acid molecule encoding a polypeptide of any of paragraphs 1-64.

68. A vector comprising a nucleic acid molecule of paragraph 67.

69. A cell comprising a nucleic acid molecule of paragraph 67 or a vector of paragraph 68.

70. A kit comprising a polypeptide of any of paragraphs 1-64 and instructions to use of the polypeptide.

71. A container comprising a polypeptide of any of paragraphs 1-64.

72. A method of producing a polypeptide, the method comprising culturing a cell of paragraph 69 under conditions that allow production of an antibody molecule, thereby producing the polypeptide.

73. The method of paragraph 72, further comprising isolating or purifying the polypeptide.

74. A method of treating a disorder, the method comprising administering to a subject in need thereof an effective amount of a polypeptide of any of paragraphs 1-64 or a composition of paragraph 65 or 66, thereby treating the disorder.

75. A polypeptide of any of paragraphs 1-64, or a composition of paragraph 65 or 66, for use in treating a disorder in a subject.

76. Use of a polypeptide of any of paragraphs 1-64, or a composition of paragraph 65 or 66, in the manufacture of a medicament for the treatment of a disorder in a subject.

77. A method of detecting a molecule, the method comprising contacting a cell or a sample from a subject with a polypeptide of any of paragraphs 1-64, thereby detecting the molecule.

EXAMPLES

A structure and network based framework was developed to interrogate the engagement of IgG with multiple Fc receptors (e.g., FcRn, C1q, TRIM21, FcγRI, FcγRIIa/b, and FcγRIIIa). Using this framework, features that govern Fc-FcRn interaction and multiple distinct pathways for enhancing FcRn binding in a pH specific manner were identified. Network analysis provided a lens to study the allosteric impact of FcRn optimization mutations on the distal FcγR engagement. Applying these principles, a panel of distinct Fc variants that enhance FcRn binding with robust biophysical properties and wild-type like binding to activating receptors were engineered. Control polypeptides with these Fc variants have shown a half-life improvement of >9 fold and robust effector functions such as ADCC, ADCP, CDC and ADIN mediated by TRIM21.

Figure 20A:
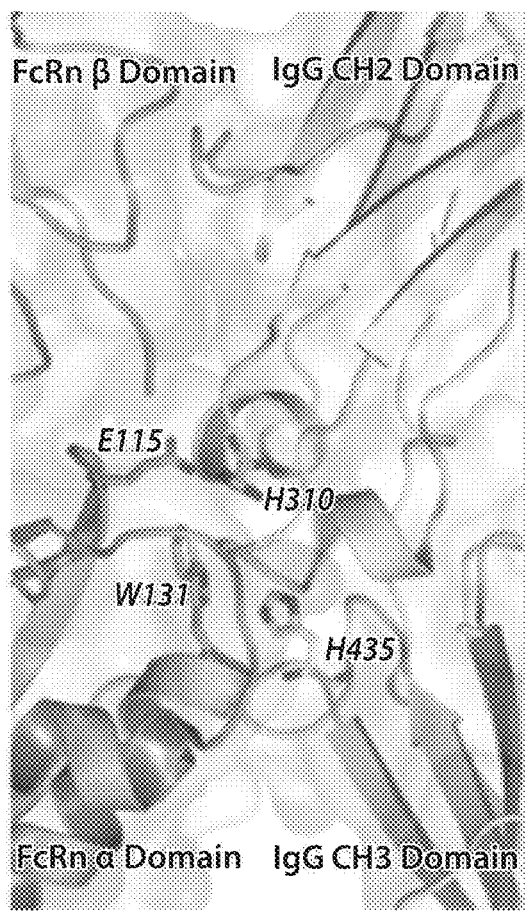
FIG. 20A depicts the IgG Fc structure and Fc-FcRn interaction.

Example 1: Structure Characterization and Molecular Features of Fc-FcRn Interaction A co-crystal structure of the human FcRn protein in complex with the Fc domain of a human IgG1 and human serum albumin was recently reported (Oganesyan et al., *J Biol Chem*, 2014. 289 (11): 7812-2). Inspection of the structure (FIG. 20A) shows that both the alpha and beta subunits of the FcRn molecule participate in binding to the Fc-domain, making contact with both CH2 and CH3 domains of the Fc. The primary interaction is mediated by the alpha-subunit on the FcRn side and CH2 domain on the Fc side. The pH specific nature of binding is driven by the histidine residues at positions 310 and 435 (Kabat numbering) which undergo protonation at acidic pH and make critical contacts with FcRn glutamate at position 115 and aspartate at position 130. Mutation of either of the two histidine residues significantly reduces the binding affinity of Fc with FcRn (Oganesyan et al., *J Biol Chem*, 2014. 289(43): 29874-80; Raghavan et al., *Biochemistry*, 1995. 34(45): 14649-57). In addition to the H310 and H435, a number of other Fc residues (L251, I253, R255, P257, H285, N286, K288, T307, V308, L309, Q311, L314, H433, N434, and Y436) are involved in making molecular contacts with FcRn.

Figure 20B:
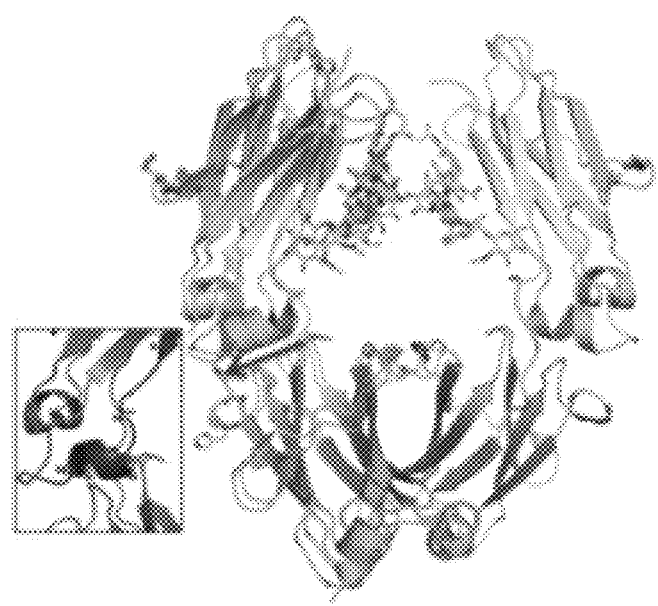
FIG. 20B depicts the structures of Fc at two different pHs.

The structure of Fc has been solved at different pHs (Crispin et al., *Proc Natl Acad Sci USA*, 2013. 110(38):

E3544-6; Ahmed et al., *J Mol Biol*, 2014. 426(18): 3166-79; Chen et al., *ACS Chem Biol*, 2016. 11(7): 1852-61). Superposition of the crystal structure of Fc at pH 4.0 (pdb id 4BYH) and 6.5 (pdb id 4Q7D) reveals a number of subtle changes, including lateral displacement of the 250-helix and differences in the relative orientation of CH2 (FIG. 20B). Given that FcRn binding amino acid residues such as M252 and I253 are located on the 250-helix, the observed displacement of the helix is expected to influence the FcRn binding (Oganesyan et al., *J Biol Chem*, 2014. 289 (11): 7812-2). Further, the difference in the relative orientation of CH2 with respect to CH3 highlights the conformational flexibility of the CH2 region (FIG. 20B) (Frank et al., *J Mol Biol*, 2014. 426(8): 1799-811). Given that the FcRn-Fc interface is found across both the CH2/CH3 domains of the Fc, the conformation dynamics of the CH2 domain is also expected to influence the FcRn binding. Deuterium exchange studies on the Fc residues in the presence and absence of FcRn at acidic and neutral pHs showed that FcRn binding to Fc molecule offers protection to its binding Fc residues; however, in the absence of FcRn molecule the 250-helix residues at acidic pH showed enhanced Deuterium exchange suggesting that pH change induces conformational change for this region (Walters et al., *J Biol Chem*, 2016. 291(4): 1817-25; Jensen et al., *Mol Cell Proteomics*, 2017. 16(3): 451-456).

Analysis of the strength of engagement of Fc with FcRn at acidic pH reveals that human FcRn binds to human Fc domain with weak affinity (>600 nM). The kinetic parameters further show that while the rate of association ($k_{on}$~$10^5$ $M^{-1}$ $s^{-1}$) of Fc-FcRn interaction is comparable to a typical antibody-antigen interaction, the lower binding affinity is primarily due to the fast dissociation rate ($k_{off}$~0.1 $s^{-1}$) of Fc-FcRn interaction (Suzuki et al., *J Immunol*, 2010. 184(4): 1968-76). The conformational flexibility of the CH2 subdomain is thought to contribute to the poor $k_{off}$ of FcRn binding. Improving the off rate of Fc-FcRn interaction can serve as a key facet for improved half-life (Datta-Mannan et al., *J Biol Chem*, 2007. 282(3): 1709-17).

Figures 21A, 21B:
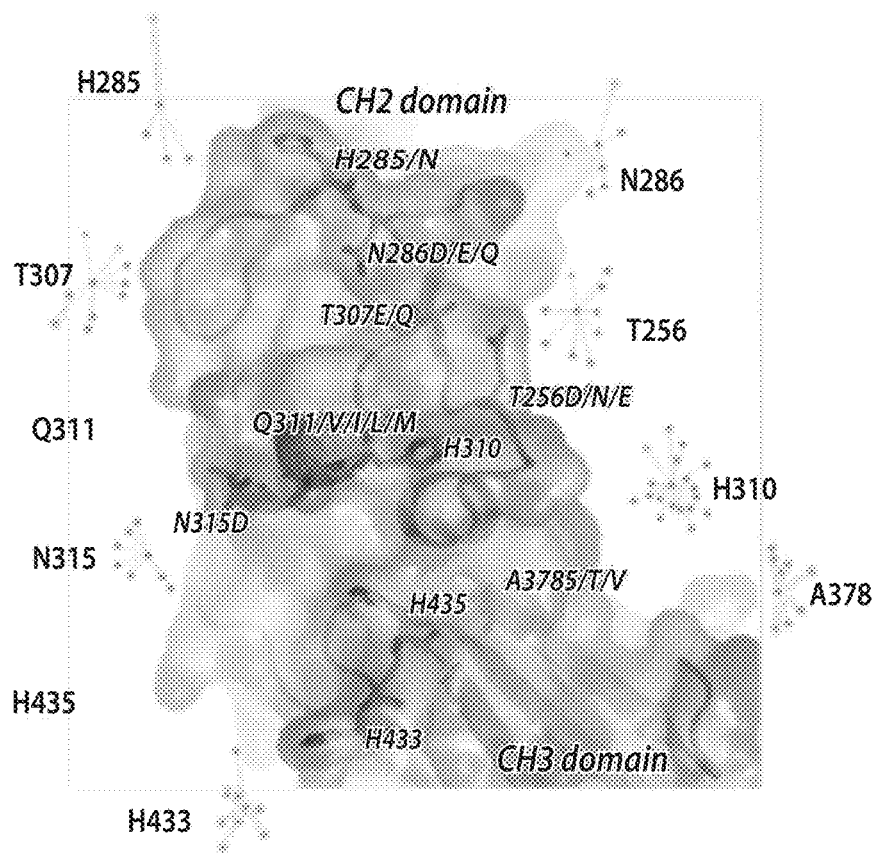
FIG. 21A depicts the types of residues with potential to mediate Fc-FcRn interaction.
FIG. 21B depicts the molecular interaction of key residues of exemplary engineered Fc variants.

Towards that, four sets of Fc residues, mutations to which could impinge on FcRn interaction and dissociation rate ($k_{off}$), were identified (FIG. 21A). This includes residues that make direct contact with FcRn as well as peripheral and non-surface exposed residues that have the potential to modify the interaction surface and residues that have the potential to influence 250-helix dynamics. Indeed, some of these positions have been previously interrogated and half-life enhancing mutants such as M252Y/S254T/T256E (YTE), M428L/N434S (LS), T307A/E380A/N434A (AAA), T250Q/M428L (QL), V308P, include combinations of mutations at the listed sites.

In the analysis, the role of each residue was first investigated in silico, and the network of interactions mediated by the residue was identified (FIG. 21B). Specific set of mutations were designed to enhance hydrophobic interactions in the Fc-FcRn interface and to enhance polar and electrostatic interactions at the periphery of the Fc-FcRn interface. Mutations of non-contacting residues near the interface can enhance the electrostatic charge complementarity and the affinity by reducing the $k_{off}$ rate (Lee and Tidor, *Protein Sci*, 2001. 10(2): 362-77; Whitehead et al., *Nat Biotechnol*, 2012. 30(6): 543-8). The FcRn binding site on Fc has overlaps with the binding site of intracellular receptor TRIM21, protein A used for antibody purification and the Fc-Fc interaction interface formed during hexamerization of IgG for CDC activity. Substitution of at each position was assessed for impact on these binding to TRIM21, protein A and Fc. More than 30 distinct positions were chosen for substitutions. Combination of the individual mutations were designed based on the following guiding principles (a) avoiding introduction of large clusters of charge or hydrophobicity to minimize binding to solvent ions and impact on thermal stability of the IgG and (b) incorporate diversity in the types of interaction, not just electrostatic or hydrophobic (c) include mutations across CH2 and CH3 domains. Based on these considerations, more than 150 unique mutant combinations were designed and experimentally evaluated.

Figures 11A, 11B:
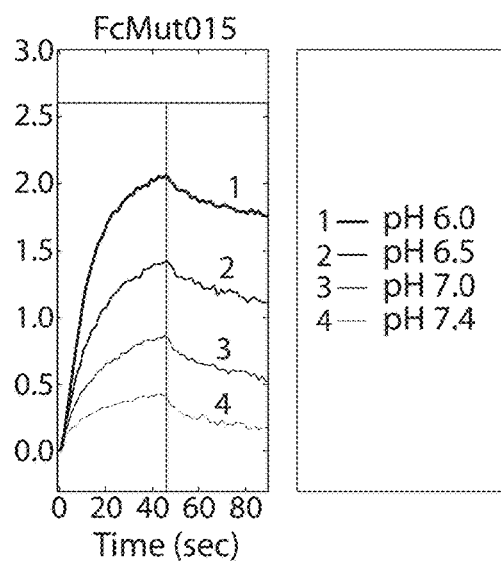
FIG. 11A depicts $K_d$, $k_{on}$ and $k_{off}$ of exemplary Fc engineered antibodies. Values presented as fold change as compared to IgG containing WT Fc.
FIG. 11B depicts improved binding to FcRn at pH 6.0 and poor binding to FcRn at pH 7.4 of a representative Fc engineered antibody.
Figure 22:
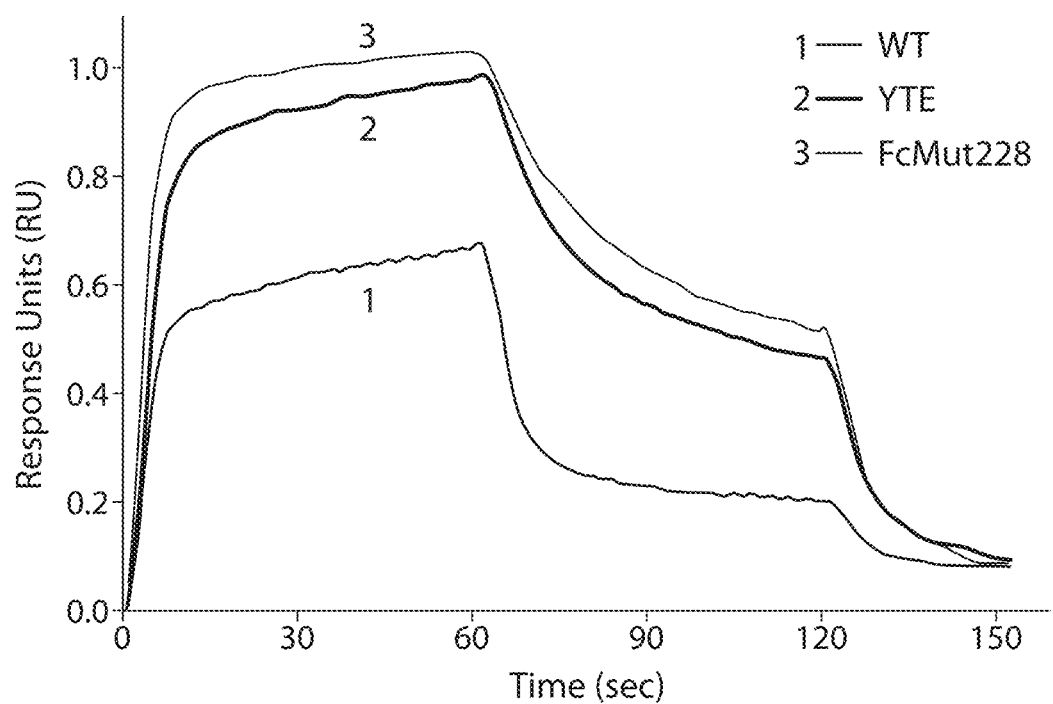
FIG. 22 depicts an exemplary Octet sensogram.

IgG1s incorporating the designed Fc variants on either actoxumab or motavizumab Fab were recombinantly expressed and evaluated for binding to human FcRn by biolayer interferometry using two different protocols: FcRn on NiNTA biosensor with IgG as the analyte, and IgG on an anti-CH1 biosensor with FcRn as the analyte. The assays were used to quantify binding at pH 6.0 followed by dissociation at pH 6.0 and pH 7.4, as well as binding and dissociation at pH 7.4 (FIG. 11A). Fc variants incorporating mutations at P257 and V308 had high affinity at pH 6.0 but displayed markedly slower off-rates at pH 7.4 and were not considered for further analyses. More than 10 distinct variants had greater than 5-fold decrease in $K_d$ as compared to IgG with WT Fc. Further, these variants decreased the $k_{off}$ by more than 2.5-fold (FIG. 22).

Figure 27A:
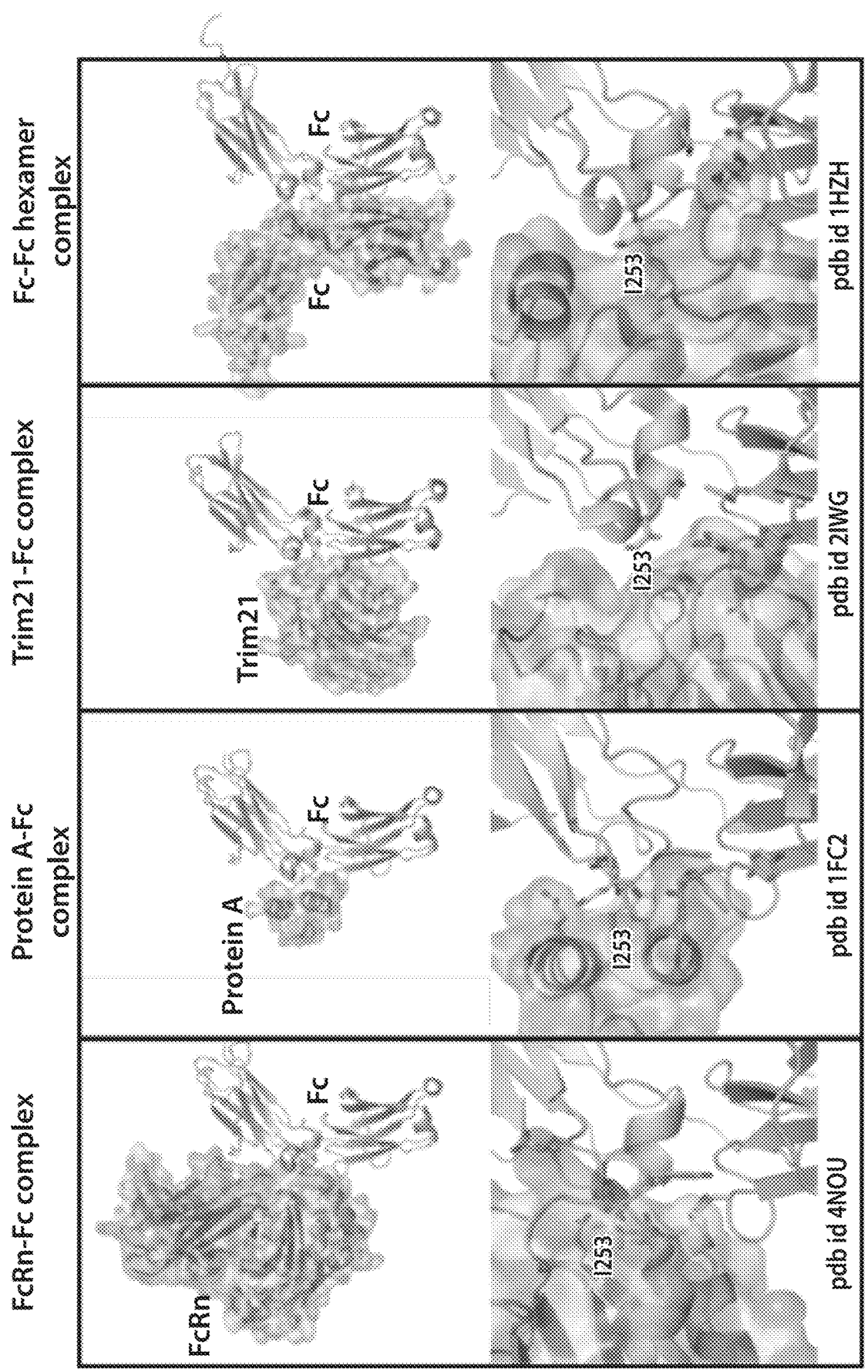
FIG. 27A depicts the structures of the FcRn-Fc complex, Protein A-Fc complex, Trim21-Fc complex, and Fc-Fc hexamer complex.
Figure 27B:
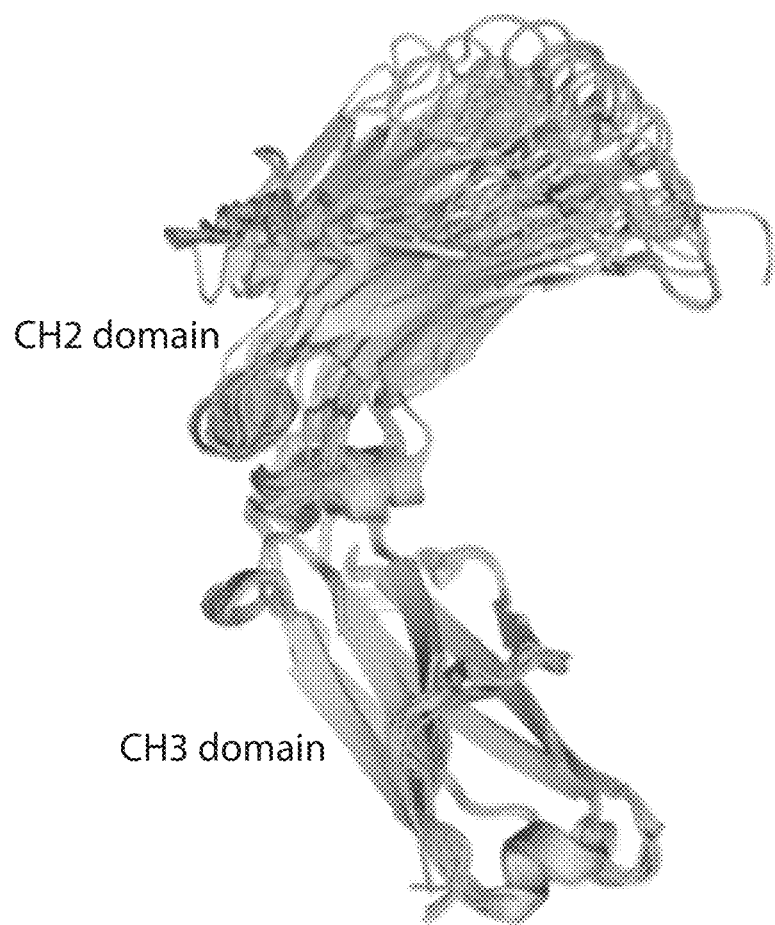
FIG. 27B depicts the superposition of crystal structures of Fc domain highlighting Fc domain dynamics.

The FcRn binding site on the Fc domain considerably overlaps with the protein A and Trim21 binding sites as determined from their complex crystal structures (FIG. 27A). The Fc domain also binds to C1q to mediate CDC, however the C1q binding site does note overlap with FcRn binding site on Fc. C1q is naturally found as hexamer and a homo-hexamer assembly of Fc domains is expected to not only have a better C1q binding and also CDC. The Fc-Fc interface for formation of homo-hexamer overlaps with the FcRn binding site (FIG. 27A). Superposition of crystal structures of Fc domain shows that the orientation of the CH2 domain in these structures varies with respect to the CH3 domain illustrating the conformational flexibility of the CH2 domain (FIG. 27B). Since the FcRn binding site is at the interface across both the CH2 and CH3 domains therefore this conformational flexibility may be important for its binding.

Example 2: Effect of Fc Region Mutations on pH Specific Fc-FcRn Binding

Figure 6:
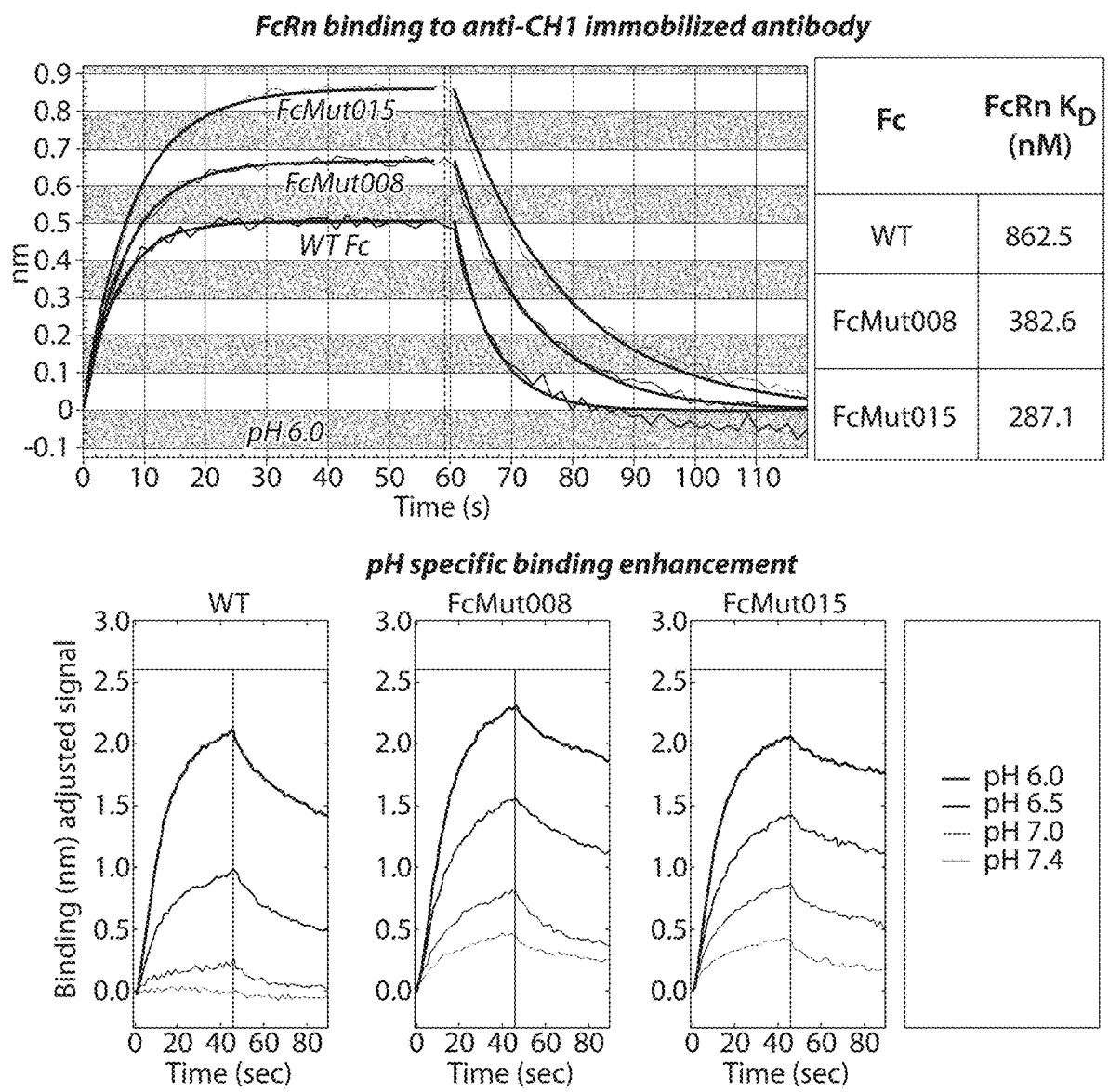
FIG. 6 depicts FcRn binding to anti-CH1 immobilized antibody and pH specific enhancement.

The FcRn binding affinity of Fc variants FcMut008 and FcMut015 was assessed by Octet. Antibody was immobilized on the Octet tip by anti-CH1 antibody and FcRn was in solution. As shown in FIG. 6, FcMut008 and FcMut015 had increased affinity to FcRn. The binding is pH specific and increased binding at pH 6.0 was observed.

Example 3: Cell-Based FcRn Binding Competition Assay

Figure 7:
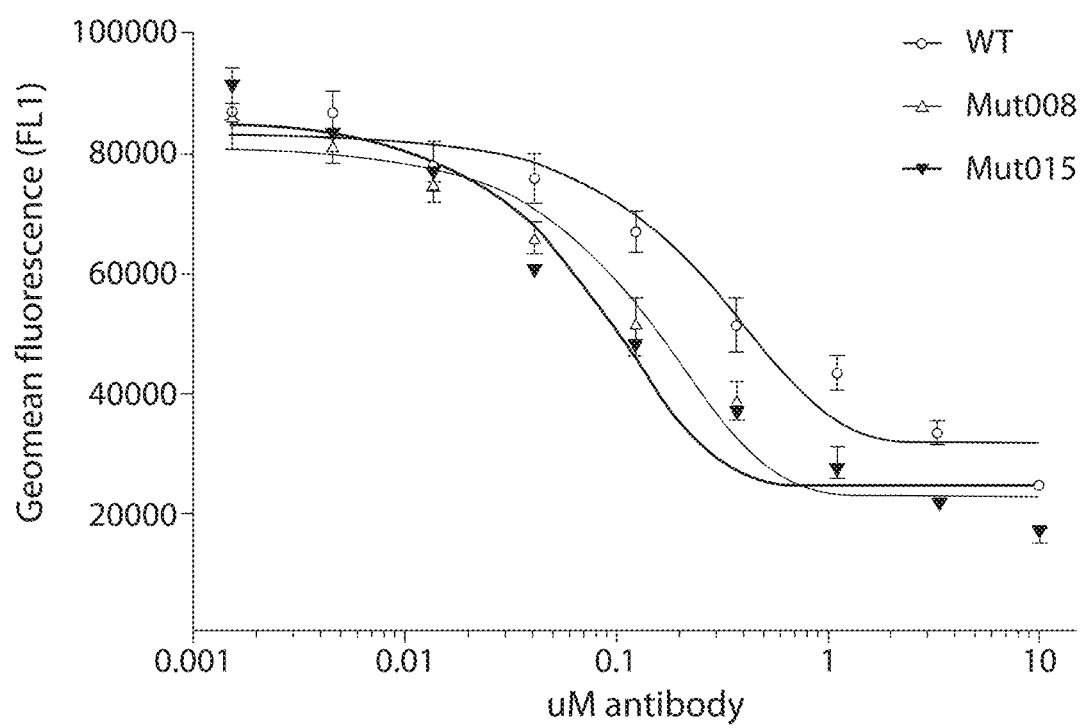
FIG. 7 depicts the results of a cell-based FcRn binding competition assay.

Cell-based competition assay provides a robust, specific, linear assay to show differences in relative binding of Fc variants. FcRn-expressing cells were obtained by transient transfection of FcRn alpha and β2m. Cells were incubated at pH6.0 with dilutions of IgG and fixed concentration of fluorescently-labeled Fc (Fc-A488). Cell-bound fluorescence was read by FACS. The results are shown in FIG. 7. FcMut008 and FcMut015 showed improved FcRn binding at pH6.0.

Example 4: Effect of Fc Region Mutations on FcγR Engagement

Figure 8:
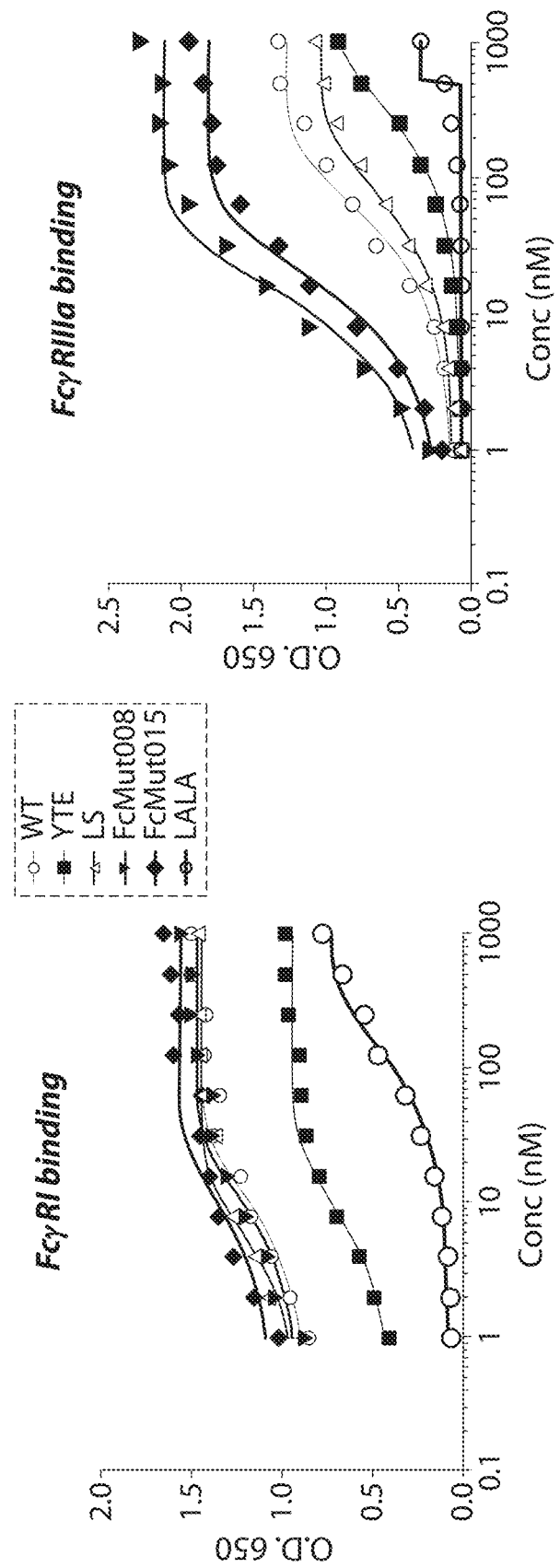
FIG. 8 depicts the binding of exemplary antibody molecules to FcγRI and FcγRIIIa.

The binding of exemplary mutant antibody molecules to FcγRI and FcγRIIIa was determined. As shown in FIG. 8, FcMut008 and FcMut015 retained and in some instance enhanced FcγR engagement.

Figure 9:
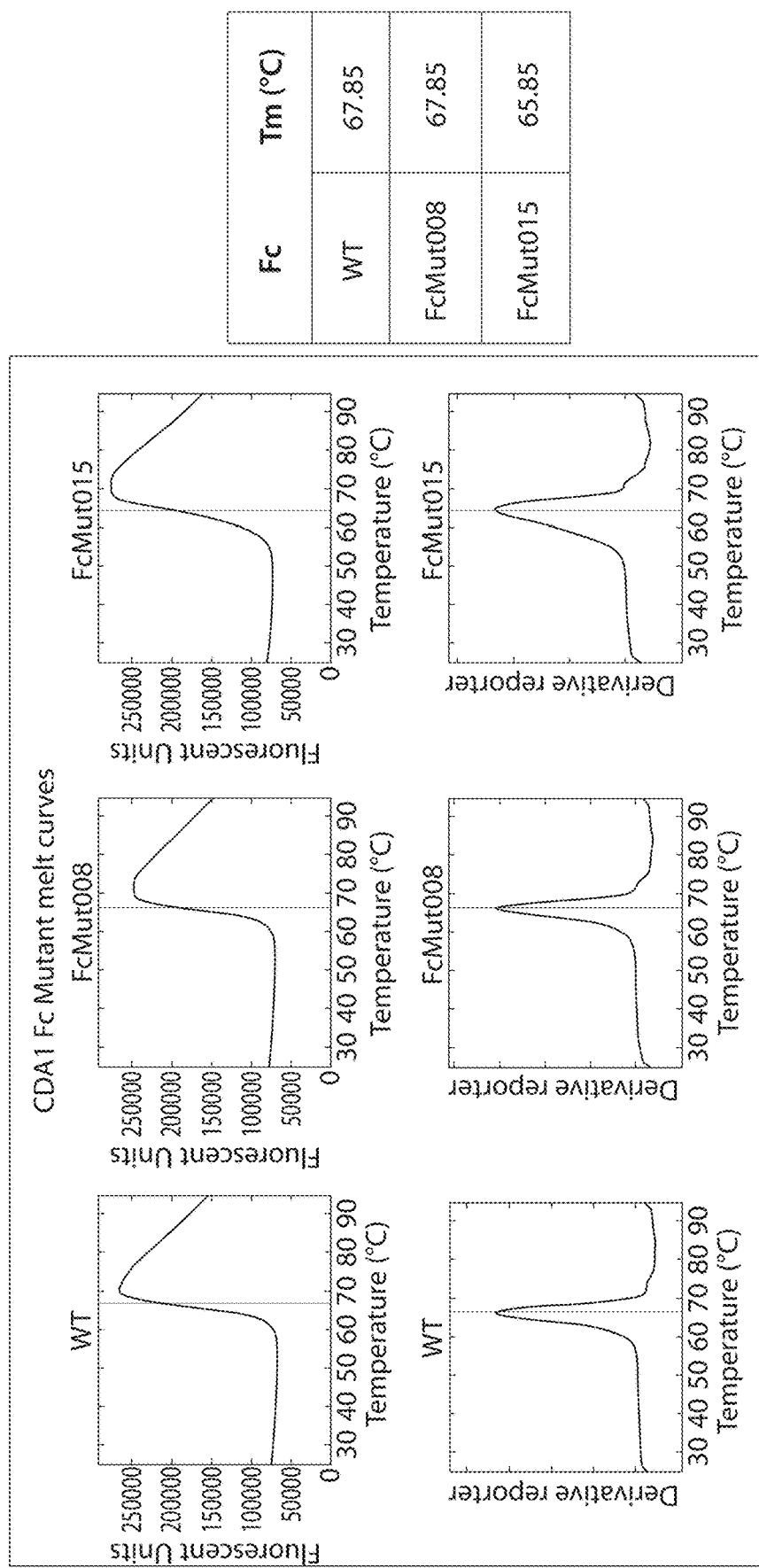
FIG. 9 depicts the thermal stability of exemplary antibody molecules.

Example 5: Effect of Fc Region Mutations on Thermal Stability and Biophysical Characterization of Fc Variants The thermal stability of exemplary mutant antibody molecules was determined. The thermal stability was measured by SYPRO orange. As shown in FIG. 9, FcMut008 and FcMut015 retained high melting temperature.

Figure 23:
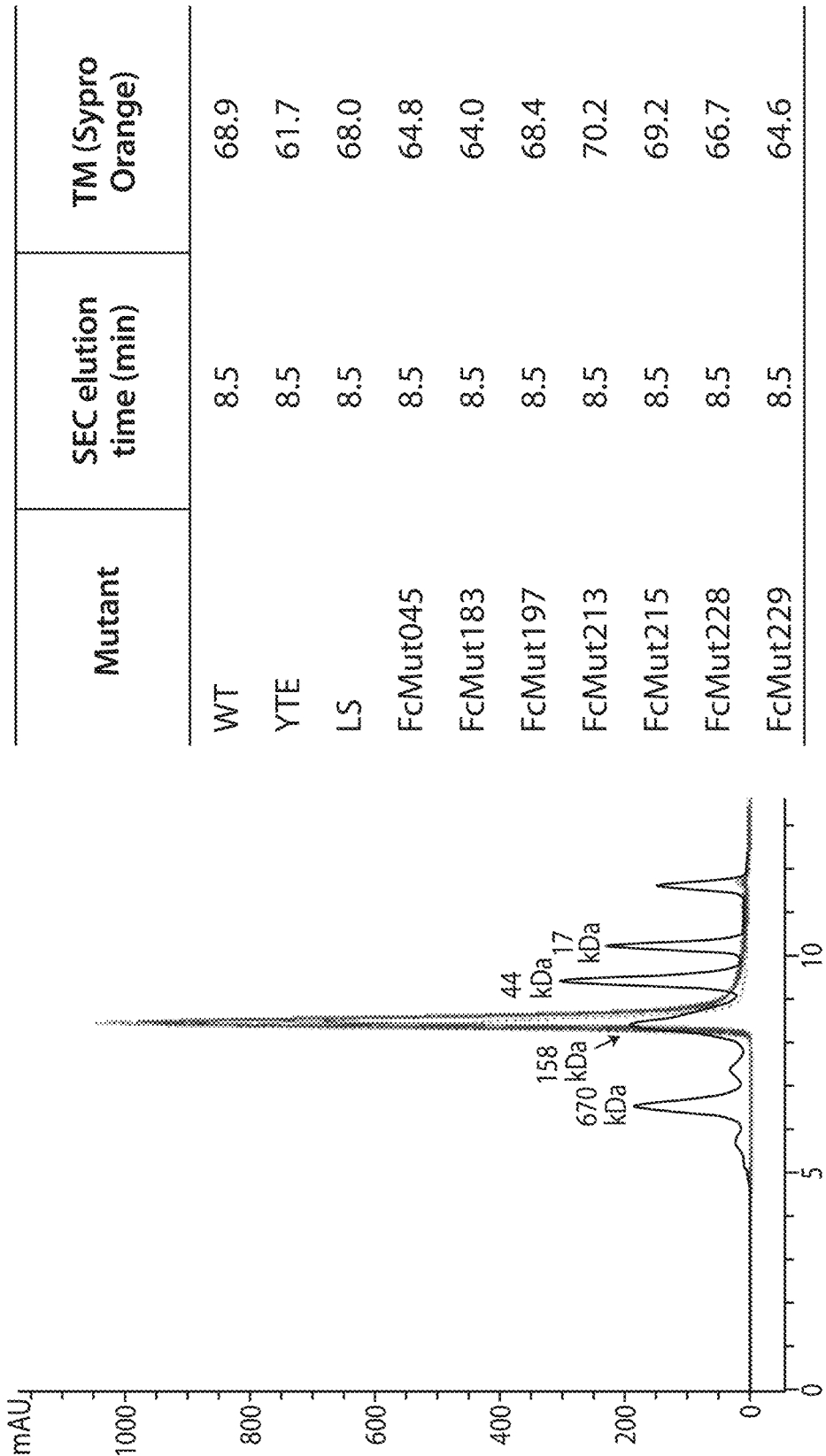
FIG. 23 depicts the SEC profile and Tm of exemplary Fc variants.
Figure 24:
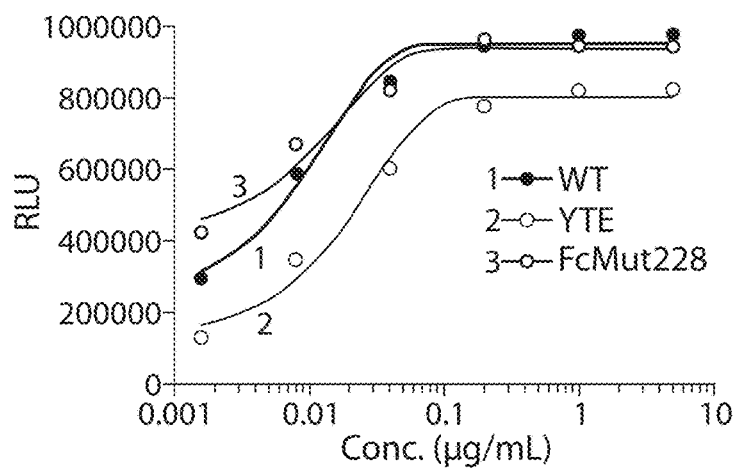
FIG. 24 depicts the binding of Fc variants to FcγRIIIa (ADCC activity) and to C1q (CDC activity).
Figure 24:
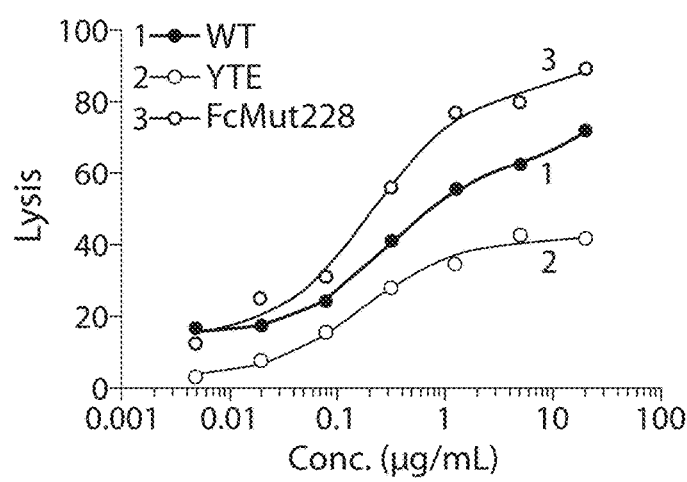
Figures 25A, 25B:
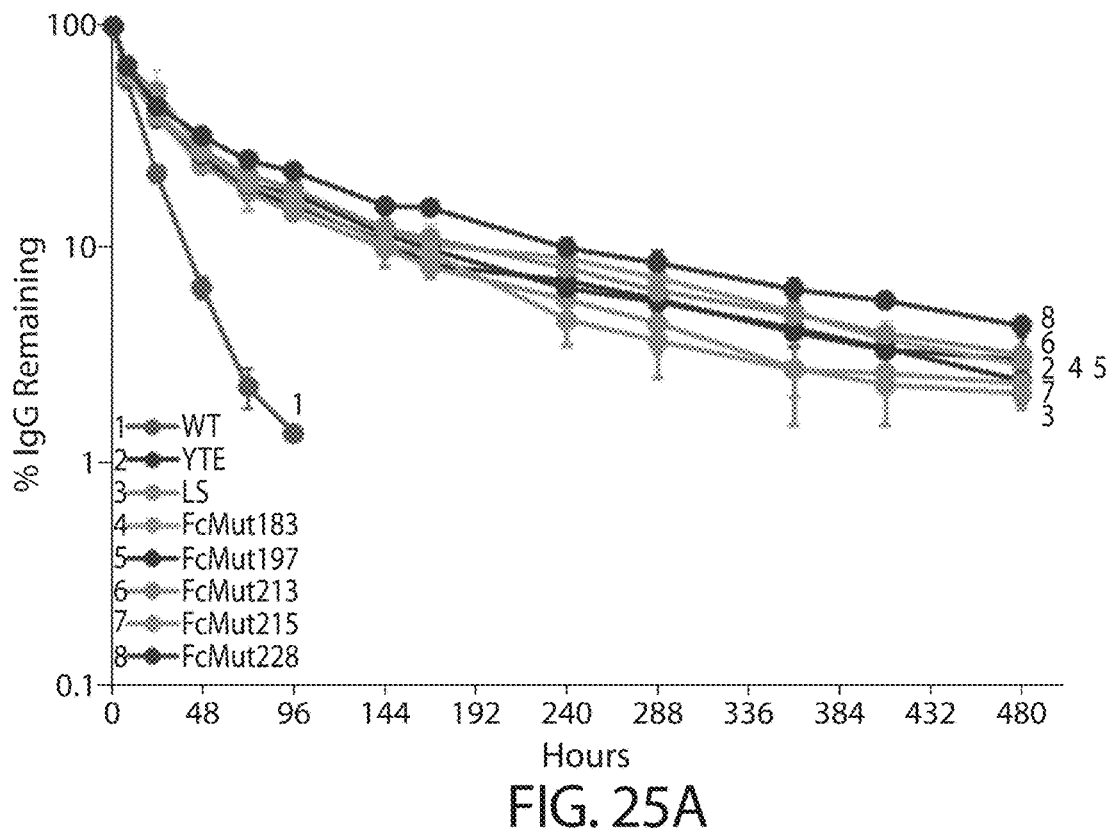
FIG. 25A depicts the pharmacokinetic characterization of IgGs with Fc variants. Plot shows change in concentration of IgG over time.
FIG. 25B depicts the PK characterization of exemplary Fc variants.

The impact of incorporating exemplary Fc variants on biophysical attributes was experimentally assessed. IgGs incorporating the Fc variants on motavizumab Fab were tested on SE-HPLC. All samples eluted at similar retention times as wild-type Fc, and displayed clean monomeric profile, and no aggregates were detected (FIG. 23). The IgGs were also assessed for the thermal stability of the CH2 and CH3 domains by Differential Scanning Fluorimetry (DSF). The melting temperature ($T_m$) of the wild type human CH2 and CH3 domain, as measured differential scanning calorimetry, is approximately 70° C. and 81.5° C., respectively (Ionescu et al., *J Pharm Sci*, 2008. 97(4): 1414-26). The DSF experimental results in this Example yielded similar results with a CH2 and CH3 $T_M$ of 68.8° C. and 80.8° C., respectively. The half-life extending Fc variant YTE has been reported to decrease the $T_M$ of the CH2 domain by 6.7° C. (Majumdar et al., *MAbs*, 2015. 7(1): p. 84-95.). In the experiments described in this Example, the $T_M$ of the CH2 domain of YTE was 7.2° C. lower than WT. Additionally, mutations at 247, 257, and 308 significantly impacted the $T_M$ of CH2. The exemplary Fc variants (FcMut183, FcMut197, FcMut213, FcMut215, FcMut228, FcMut229) were thermally stable with the $T_M$ of the CH2 domain >64° C. (FIG. 23).

Example 6: Evaluation of Fc Variants in Transgenic Mice Model

Tg32 mice were homozygous, 8 week old, males. There were 4 mice per test article group. The test articles included CDA1-WT, CDA1-FcMut008, and CDA1-FcMut015. The mice were dosed at 10 mg/Kg by IV administration. Data were collected at thirteen time points (1 h, 8 h, 1 d, 2 d, 3 d, 4 d, 6 d, 8 d, 10 d, 13 d, 16 d, 19 d, and 22 d). Human IgG was quantified by ELISA using an anti-hIgG polyclonal antibody.

Tg32 is a human FcRn transgenic mouse model that can be used in drug discovery for early assessment and prediction of human pharmacokinetics of monoclonal antibodies. Monoclonal antibody clearance in Tg32 homozygous mice has the strongest correlation to monoclonal antibody clearance in humans (Avery et al. *MAbs*. 2016; 8(6):1064-78).

Figure 10:
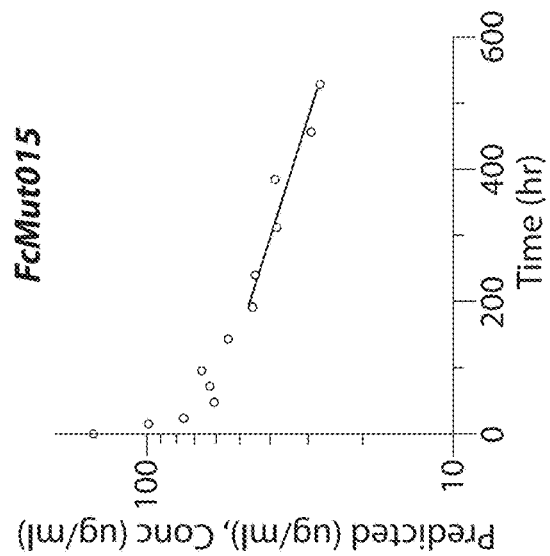
FIG. 10 depicts the half-lives of exemplary antibody molecules in Tg32 mice.
Figure 10:
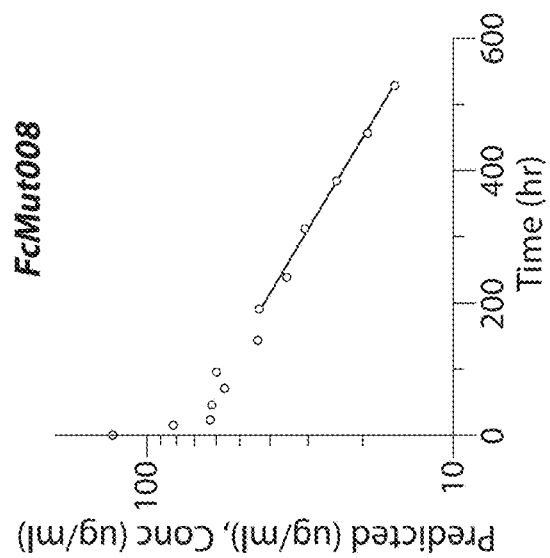
Figure 10:
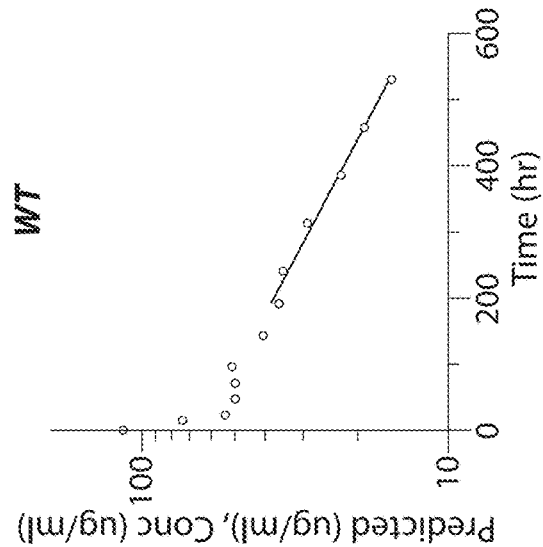

CDA1 (actoxumab) is known to have a half-life of >25 days in human. In vivo evaluation with additional mAbs in Tg32 model was performed. The different constructs can also be evaluated on Tg276 mice which are reported to have increased half-life differences between IgG variants. The results are shown in Table 2 and FIG. 10. FcMut015 increased the half-life of CDA1 in Tg32 mice.

TABLE 2

Half-Lives of Exemplary Antibody Molecules in Tg32 Homozygous Mice

| Group | $t_{1/2}$ (hr) | $C_{max}$ (ug/ml) | $C_{last}$ (ug/ml) | $AUC_{inf}$ (hr * ug/ml) | Rsq |
|---|---|---|---|---|---|
| WT | 261.17 | 116.03 | 15.40 | 24108.03 | 0.99 |
| FcMut008 | 231.92 | 131.33 | 15.74 | 25687.39 | 0.99 |
| FCMut015 | 436.69 | 151.82 | 27.69 | 42735.9 | 0.93 |

Example 7: Fc Engineering of Exemplary Antibodies

FcRn interaction with IgG is believed to be mediated through Fc. The binding of Fc to FcRn is generally pH specific (typically little or no binding at pH7.4 and strong binding in acidic environment). Structure of FcRn in complex with Fc domain of IgG1 is known and each FcRn molecule binds to an Fc-monomer. Fab domains can also influence binding of IgG to FcRn.

Network analysis of Fc-FcRn complex highlights the centrality of H310 in engagement with FcRn. H310 is highly interconnected to multiple other highly networked residues. Mutations in the H310 cluster, and neighboring (connected nodes) may strengthen the H310 network. Analysis of subnetworks informs introduction of synergistic mutations for favorable FcRn interaction, with minimal impact on other Fc residues.

To identify Fc variants with improved binding to FcRn at pH 6.0, various Fc mutations were engineered into IgG1 Motazivumab (WT). All antibodies were assessed for binding to FcRn using biolayer interferometry. Briefly, anti-CH1 biosensors (ForteBio) were loaded with each antibody of interest. Loaded biosensors were exposed to recombinant FcRn protein at pH 6.0 to detect binding. After saturation, biosensors were exposed to buffer alone at pH 6.0 to measure dissociation of the FcRn from each antibody. The result is a response curve representing on rate and off rate of the antibody. These rates were calculated using the ForteBio software and compared to the rate of wild type Motavizumab. The fold increase in on-rate and the fold decrease in off-rate as compared to wild type are listed in the table. Numerous antibody mutations significantly increased and decreased on and off rate, respectively (FIG. 11A). Also shown is the binding of a representative Fc variant to FcRn at a pH range of 6.0 to 7.4. It is important that the affinity of the Fc mutant antibodies for FcRn is improved at pH 6.0 but not significantly enhanced at a higher pH such as pH 7.4. FIG. 11B demonstrates that this representative antibody still shows poor binding to FcRn at pH 7.4, a desirable feature.

Figure 11C:
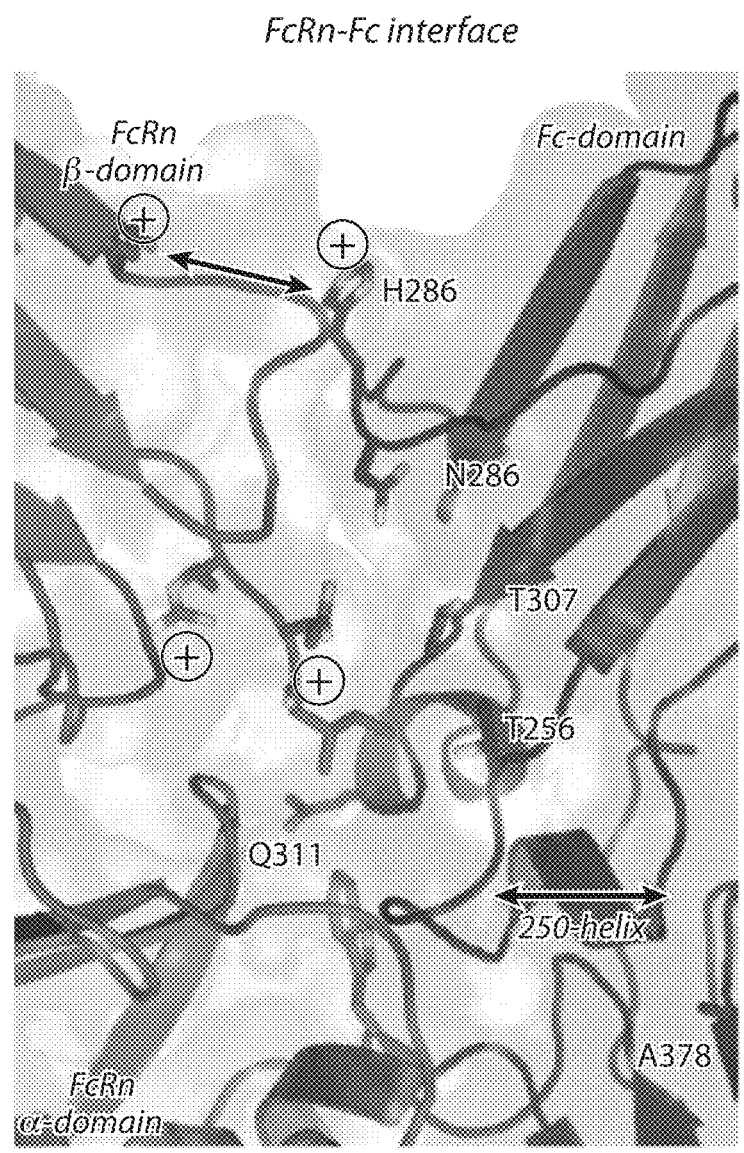
FIG. 11C depicts the interaction of the CH2 domain of the antibody Fc with the FcRn molecule.

FIG. 11C shows the interaction of the CH2 domain of the antibody Fc with the FcRn molecule. The engineering efforts described herein attempted to improve shape complementarity (SC), electrostatic charge complementarity (CC), and hydrophobic complementarity (HC). A few positions on the Fc are noted as important for the interaction. Also noted is the 250 helix. This helix is dynamic and moves depending on the pH of the environment. This is important in the binding of the Fc domain to FcRn at pH 6.0 but not pH 7.4.

Exemplary Fc variants were tested in developability assays, the results of which are summarized in FIG. 12. Assays, including Sypro orange, SDS PAGE and SEC-HPLC, were performed. For expression determination, constructs were transfected into Expi293 cells in 96 well culture dishes using ExpiFectamine as described by the manufacturer. After 5-7 days, supernatants were quantified using biolayer interferometry (Octet) equipped with anti-human CH1 biosensors using a motavizumab standard curve. For protein A binding assessment the following was performed. Constructs were transfected into Expi293 cells in 30 mL cultures using ExpiFectamine as described by the manufacturer. After 5-7 days, supernatants were harvested and antibodies purified. Using biolayer interferometry with protein A biosensors, Fc-modified antibody affinity to protein A was measured and compared to antibody containing a wild type Fc domain.

All Fc variants, expressed in the context of the Motavizumab antibody, were separated by SDS-PAGE under reducing and non-reducing conditions. Briefly, 2 µg of antibody in 5 µL of water was mixed with 5 µL of Laemmli Sample Buffer (BioRad Catalog #161-0737), with and of β-mercaptoethanol (BioRad Catalog #161-0710). The samples were boiled at 95° C. for ten minutes and then briefly centrifuged. Samples were then run on a 4-12% Bis-Tris NuPAGE gel (Thermo Scientific #NP0321BOX) in 1×MES running buffer in an XCell SureLock Gel Electrophoresis Cell (Novex Catalog #090403-839) alongside the SeeBlue Plus2 molecular weight standard (Invitrogen Catalog #LC5925). The samples were run at 200V for 35 minutes. The gels were stained with SimplyBlue SafeStain (Novex #LC6065) following manufacturer's protocol and imaged on the BioRad ChemiDoc MP Imaging System.

HPLC based size exclusion chromatography (HPLC-SEC) is an analytical tool used to determine the apparent size of a protein, monomeric purity, and the apparent level non-specific column adsorption between the protein and the silica based sizing resin. The impact of Fc mutations on the IgG elution profile was assessed on a Phenomenex Biosep 3000s column. Briefly the IgGs with various Fc variants were diluted to 1 mg/ml in PBS pH 7.4 and 20 µL was injected into the column. The elution time and percentage purity was recorded.

The thermal stability of the mAbs was determined by differential scanning fluorescence (DSF). DSF monitors the conformational stability of a protein as it is exposed to increasing thermal stress. The dye, SYPRO ORANGE®, fluoresces in a hydrophobic environment, such as hydrophobic core residues that are exposed during thermally triggered protein unfolding, or denaturation. By monitoring the fluorescent signal, the unfolding of CH2, CH3 and Fab can be monitored. Various Fc variants with Motavizumab Fab were evaluated in a SYPRO orange assay. Briefly 15 µL of IgG at ~0.5 mg/mL was mixed with 15 µL of 1:500 diluted SYPRO Orange dye and assessed by a thermocycler with fluorescent read capabilities using a 1° C. ramp from 40° C. to 99° C. The midpoint between native state and first unfolding event was reported as the transition temperature or melt temperature (Tm).

All Fc mutations were introduced in IgG1 (m3 allotype) heavy chain gene and cloned into pcDNA3.1(C). The light chain genes were cloned into pcDNA3.1(A). In all cases, the native signal peptide was replaced with an osteonectin signal peptide (GenBank accession # AAA60993). Co-expression of the heavy and light chain vectors was performed by transient transfection in Expi293 cells using the Expi293 transfection kit (Thermo Fisher catalogue # A14524) following the manufacturer's protocol. The heavy and light chain vectors were co-transfected at a 1:2 ratio. Cell culture supernatant was harvested 5 to 7 days post transfection and purified on the AKTA 10 FPLC system (GE) using HiTrap MabSelect SuRe protein A columns (GE) following manufacturer's instructions.

All antibodies were purified from cell culture supernatant using 1 mL columns packed with mAb select sure protein A resin (GE catalogue #17543801) using the AKTA purifier 10 FPLC system. Briefly, sterile filtered cell culture supernatant was loaded onto the columns at a flow rate of 2 mL/minute. Columns were washed with 10 column volumes of PBSN (1×PBS with 0.05% sodium azide). Antibodies were eluted with 10 column volumes of elution buffer (100 mM glycine pH 2.5) and neutralized by addition 17.5% v/v of neutralization buffer (1M Tris, 1M NaCl, pH 8.0) and collated in 1 mL fractions. The chromatogram for absorbance at 280 nm was used to identify elution fractions containing the antibody. All antibodies were then dialyzed into 1×PBS using 10,000 dalton molecular weight cut-off cassette (Thermo Fisher catalogue #66380).

Protein A binding was functionally determined by the ability of all antibodies to be purified by FPLC using protein A columns. After purification, protein A binding was further assessed by quantifying a known amount of antibody using the Octet QK$^e$ system and protein A biosensors (Pall catalogue #18-5012) following the standard quantitation protocol provided with the Octet data acquisition software.

Expi293 cells were co-transfected with a plasmid encoding the human α-FcRn with a 6× histidine tag on the C-terminus and a plasmid encoding human β2M. Cell culture supernatant was harvested 4 days post transfection. FcRn was purified from cell culture supernatant using the AKTA pure FPLC system with a HisTrap HP column (GE catalogue #17-5247-01). Post purification the protein was dialyzed into 1×PBS pH 6.0.

Screening assays were performed using anti-CH1 Fab biosensors on the Octet QK$^e$ system. Briefly, purified IgG at 10 µg/mL is loaded onto an anti-CH1 biosensor for 180 seconds. After a 60 second baseline step in 1×PBS pH 6.0, the IgG loaded tip is exposed to FcRn at a concentration of 50 µg/mL for 60 seconds, followed by dissociation for 60 seconds in PBS pH 6.0, and an additional 30 seconds in PBS pH 7.4. In addition, FcRn binding was performed using NiNTA biosensors. Briefly, recombinant human FcRn at 5 µg/mL is loaded onto a NiNTA biosensor for 180 seconds. After a 60 second baseline step in 1×PBS pH 6.0, the FcRn loaded tip is exposed to IgG at a concentration of 250 nM (37.5 µg/mL) for 60 seconds, followed by dissociation for 60 seconds in PBS pH 6.0, and an additional 30 seconds in PBS pH 7.4. After assay completion of each assay, a quantitative assessment of the affinity constant ($K_D$) at pH 6.0 is performed using the ForteBio octet software and a qualitative assessment is performed by plotting the response rate over time, allowing for visualization of the association of IgG to FcRn at pH 6.0 and the subsequent dissociation at pH 6.0 and pH 7.4.

As shown in FIG. 12, all Fc variants performed comparably to the WT antibody in all of these experiments.

Example 8: In Vivo Assessment of Half-Life and Pharmacokinetic Analysis of Engineered Antibodies Motavizumab wildtype was compared to Motavizumab containing three of Fc engineering mutations in the in vivo assessment of engineered antibody half-life. Antibodies (2-5 mg/kg) were administered to mice transgenic for human FcRn and daily samples of mouse serum were obtained (day 0-day 4). ELISA was performed on serum to quantify the amount of Motazivumab in the serum.

The amount of human IgG present in mouse serum was determined using a human IgG quantitation ELISA kit (Bethyl Labs catalogue # E80-104) following the manufacturer's protocol. All serum samples were titrated in a twofold serial dilution starting at 1:50 dilution and ending at a 1:6400 dilution. Each ELISA plate included a human reference standard curve provided with the kit in duplicate or triplicate. The standard curve contains the following concentrations: 500.0, 250.0, 125.0, 62.5, 31.3, 15.6, 7.8, and 3.9 ng/mL. The lower limit of detection was considered to be the A450 nm value obtained for the second to last point on the reference standard, which was 7.8 ng/mL. Because the starting dilution of the serum was 1:50, this puts the level of detection the assay at ~0.4 µg/mL (7.812 ng/mL×50 fold dilution). The following procedures were followed to calculate the IgG levels: (1) perform a four parameter logistic regression (4PL) on the standard curve; (2) set the maximum acceptable A450 nm signal as the reading for the third titration point on the standard curve; (3) set the minimum acceptable A450 nm signal as the reading for the seventh titration point on the standard curve; (4) mask all samples titration points that fall above the maximum acceptable signal and below the minimum acceptable signal; (5) user the reference standard 4PL curve fit to calculate the concentration for each titration point with an acceptable A450 signal and multiply that value by the dilution factor of that titration point; (6) for each sample titration, calculate the mean value for the calculated concentration across titration series.

Figures 13A, 13B:
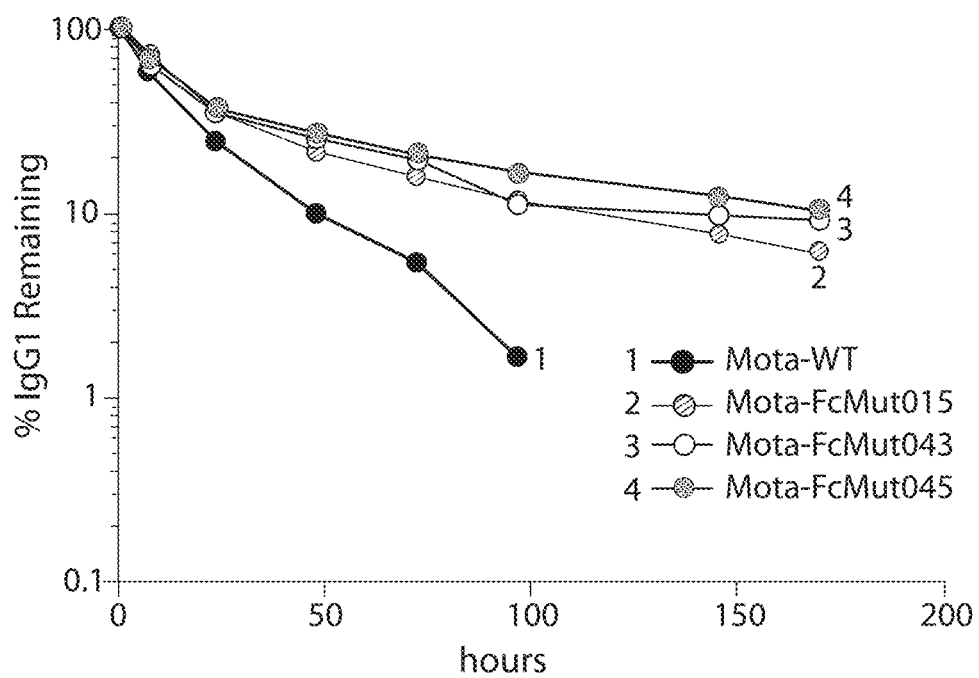
FIG. 13A depicts improved in vivo half-life of 3 Motavizumab Fc variants in comparison to WT Motavizumab (Mota-WT).
FIG. 13B depicts pharmacokinetic properties of 2 Motavizumab Fc variants and WT Motavizumab.

ELISA results were converted to percent of antibody remaining based on the day 0 timepoint representing 100%. As shown in FIGS. 13A-13B, all three antibody variants demonstrated extended half-life in this well-established mouse model of antibody half-life. Motavizumab wild-type has a half-life of 32 hours. FcMut043 and FcMut045 mutants built on FcMut008 show significant half-life improvement. FcMut045 mutant enhanced half-life 5.2 fold (about 166 hours half-life). The half-life as well as the other parameters in FIG. 13B were calculated using the Winonlin software.

Figures 14A, 14B:
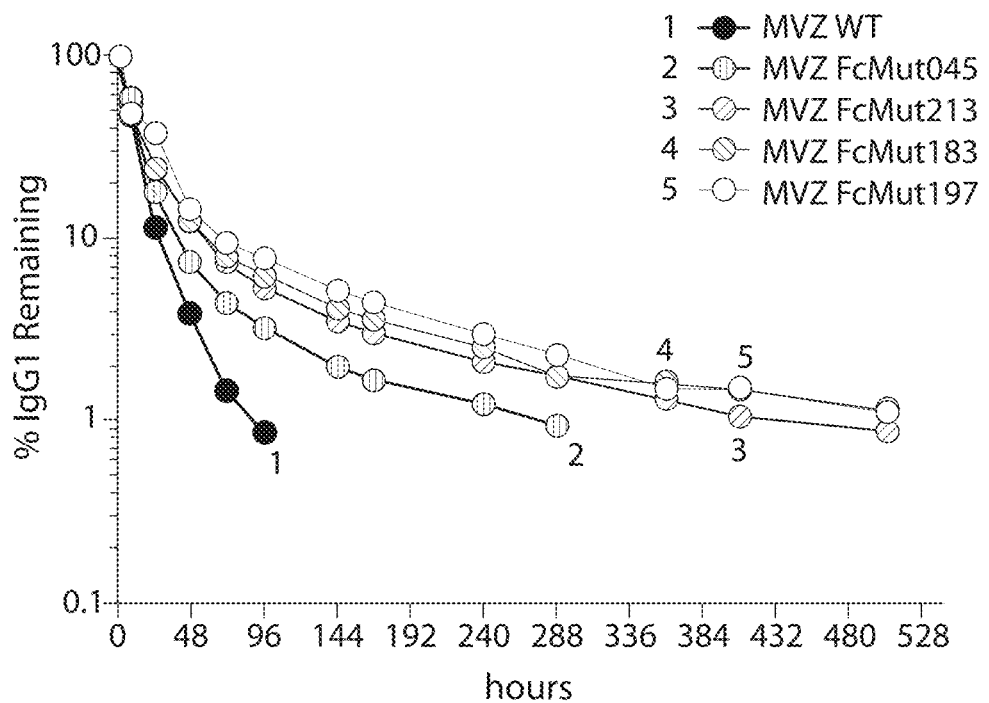
FIG. 14A depicts improved in vivo half-life of later stage Motavizumab Fc variants in comparison to WT Motavizumab (Mota-WT) administered at a dose of 5 mg/kg.
FIG. 14B depicts pharmacokinetic properties of later stage Motavizumab Fc variants and WT Motavizumab administered at a dose of 5 mg/kg.
Figures 14C, 14D:
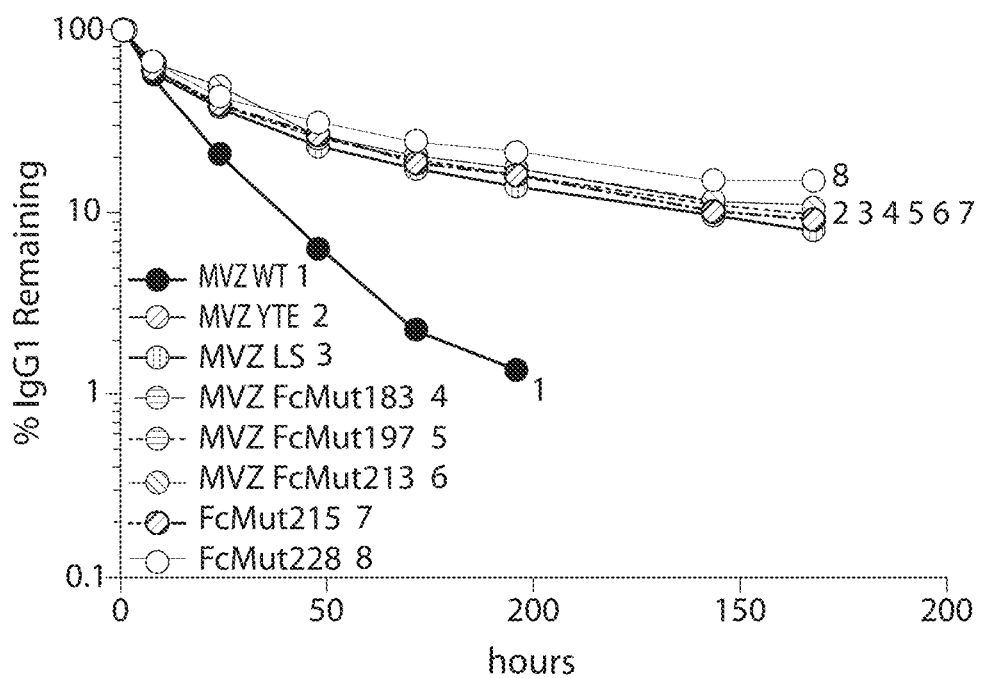
FIG. 14C depicts improved in vivo half-life of later stage Motavizumab Fc variants in comparison to WT Motavizumab (Mota-WT) administered at a dose of 2 mg/kg.
FIG. 14D depicts pharmacokinetic properties of later stage Motavizumab Fc variants and WT Motavizumab administered at a dose of 2 mg/kg.

Similar experiments were conducted with later stage Fc variants in the context of Motazivumab. When the Motavizumab variants were administered at a dose of 5 mg/kg, next generation variants (FcMut171, FcMut183, FcMut186, and FcMut197) demonstrated further enhanced half-life with more than nine fold increase in half-life observed with FcMut213 (FIGS. 14A-14B). One of the early variants (FcMut045) was included to demonstrate the improved half-life seen with the later stage designs as compared to the early stage designs. Similar results were observed when the Motavizumab variants were administered at a dose of 2 mg/kg (FIGS. 14C-14D).

To evaluate if the enhanced binding of Fc variants to human FcRn translated to increased serum persistence and longer circulating half-life life, a pharmacokinetic study of IgGs containing the different Fc variants was performed in Tg276 transgenic mice. Transgenic mouse models expressing human FcRn have been developed by the Jackson laboratory (JAX) to study PK of human Fc-containing biotherapeutics. The Tg276 mice are null for mouse FcRn alpha chain and express the human FcRn alpha transgene under the control of a constitutive promoter (actin) and use the mouse β2 microglobulin. The Tg276 homozygous or hemizygous mice have been widely used to differentiate half-lives of antibody variants.

For the in vivo study, Tg276hemi FcRn transgenic mice were dosed with 2 or 5 mg/kg of mAb intravenously. Each mAb group had 4 mice/group. Blood was collected at several time points between 1 hour and 21 days, and IgG titers were determined by quantitative ELISA as described herein. PK parameters were determined for each group of mice with a non-compartmental model using Phoenix WinNonlin version 7.0 (Certera).

The results are shown in FIGS. 14A-14D.

Example 9: In Vivo Assessment of Half-Life of Engineered Antibodies

Figure 15:
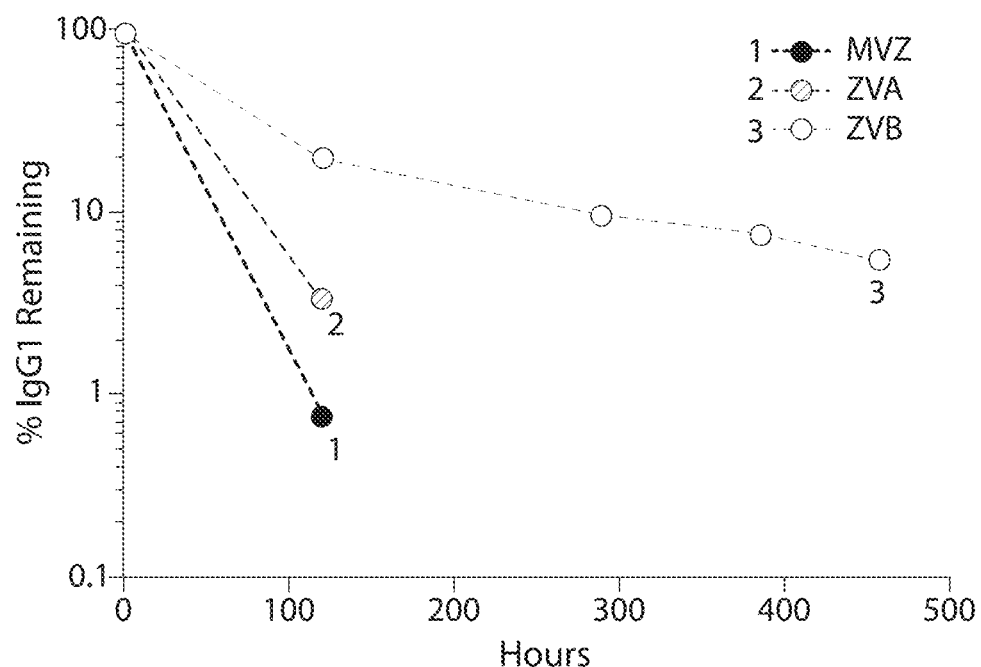
FIG. 15 depicts longer in vivo half-life of the ZVB Zika antibody.

Two Zika antibodies (ZVA and ZVB) as well as wild type Motavizumab (MVZ) were administered to mice transgenic for human FcRn at a dose of 2-5 mg/kg, and daily samples of mouse serum were obtained (day 0-day 4). ELISA was performed on serum to quantify the amount of Motavizumab. ELISA results were converted to percent of antibody remaining based on the day 0 timepoint representing 100%. ZVA antibody represents the A series antibody A-3/2. The ZVB antibody represents the A series antibody A-5/1 containing the affinity enhancing light chain modification S92Y. As shown in FIG. 15, ZVB had a much longer half-life than either Motavizumab or ZVA (both ZVA and ZVB had longer half-life than Motavizumab). These antibodies contained wild-type Fc regions so the extended half-life of the ZVB antibody is a property of the antibody itself, and not any Fc engineering.

Figure 16:
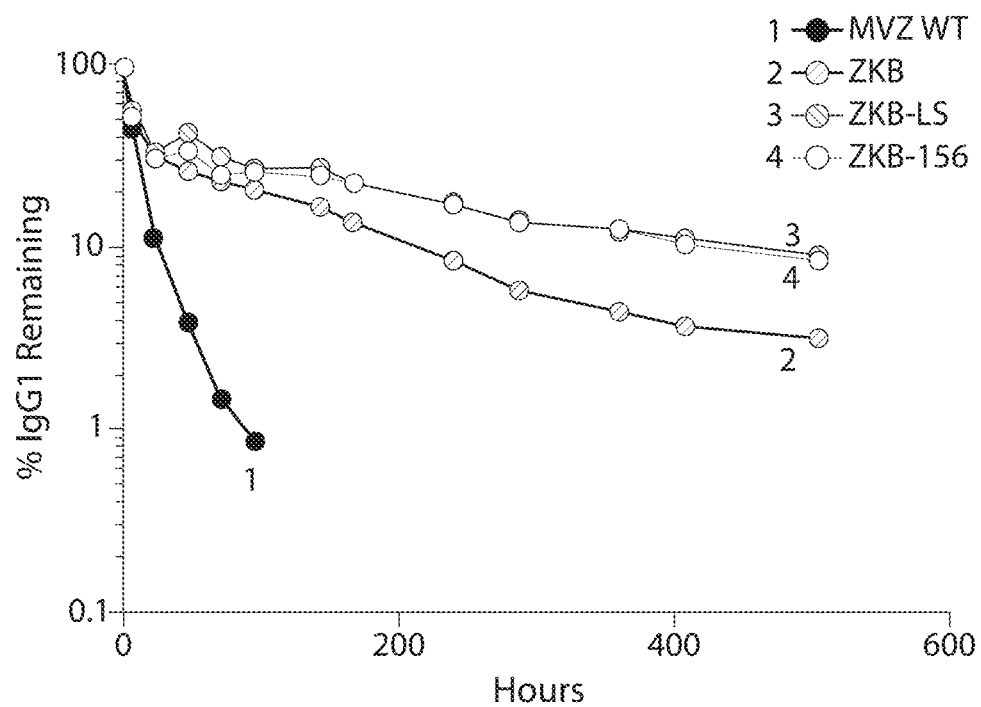
FIG. 16 depicts a similar half-life of ZKB-LS (ZVB antibody with LS Fc mutation) and ZKB-156 (ZVB antibody with Visterra 156 Fc mutation). Both of these antibodies had a longer half-life than the parental ZVB antibody (ZKB) and WT Motavizumab.
Figure 17C:
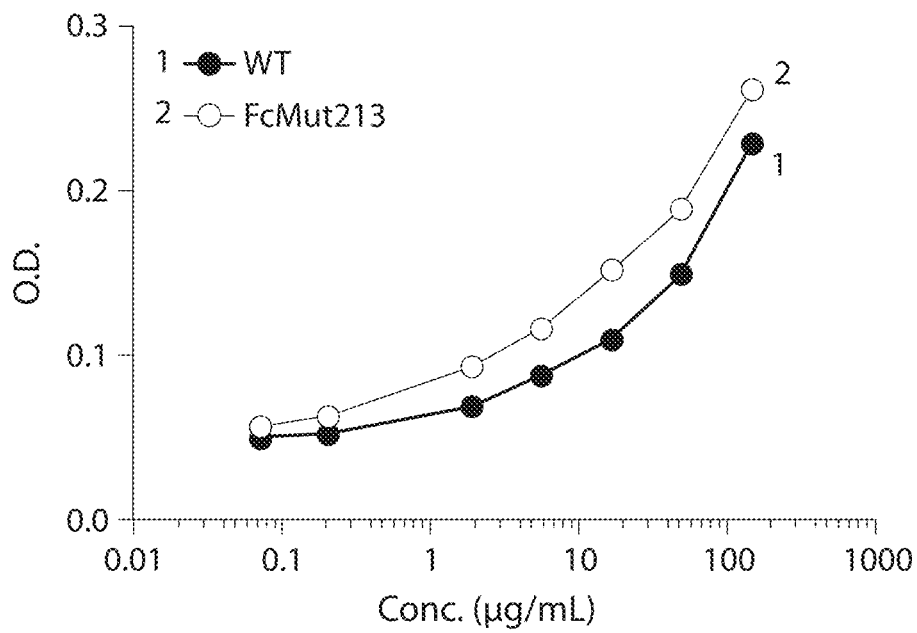
FIG. 17C depicts the binding of FcMut213 to FcγRIIA compared to wild-type.
Figure 17D:
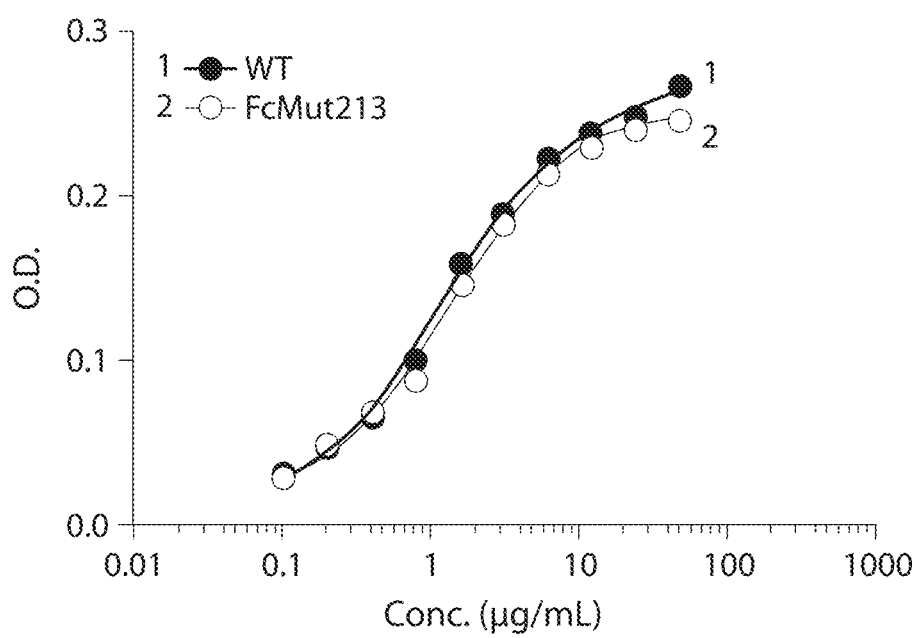
FIG. 17D depicts the binding of FcMut213 to C1q compared to wild-type.

In the next experiment, Motavizumab wild type (MVZ WT) was tested against the ZVB antibody (ZB-1/4, ZKB in the graph) and the ZVB antibody containing Fc modification 156 (L234A/L235A ("LALA") and T256D/T307R/Q311V (half-life extension), ZKB-156 in the graph) as well as the "LS" half-life extension Fc mutation (ZKB-LS). Both LS and Fc modification 156 extended half-life significantly compared to the wild-type ZVB (FIG. 16). These data demonstrate that the Visterra mutation is comparable to the literature derived LS mutation, and also demonstrates that the FC engineering efforts described herein can extend the half-life of an antibody that already has a very long half-life in this transgenic mouse model. "ZVB" is indicated as "ZKB" in FIG. 16.

Example 10: Binding to Fc Receptors and Impact on Effector Functions

Exemplary Fc variants were assessed on multiple assays for FcγRI, FcγRIIA (mediator of opsonophagocytosis), FcγRIIB, FcγRIIIA (mediator of ADCC), and C1q (mediator of CDC).

Binding to Fcγ receptors I, IIa, IIb, IIIc, and IIIc V176F (R&D Systems catalogue #1257-FC-050, 1330-CD-050, 1875-CD-050, 4325-FC-050, and 8894-FC-050) was measured by ELISA. All Fc variants were tested in the context of the Motavizumab, Rituximab, or Actoxumab antibody. Briefly, Fc receptors were coated on an ELISA plate (VWR catalogue #62409-002) at 1 µg/mL (0.1 µg/well) in PBS and stored at 4° C. overnight. Plates were washed three times with PBST (1×PBS 0.05% Tween20). Antibodies were titrated threefold in PBST-BSA from 100 µg/mL to 0.05 µg/mL and 100 µL was added to each well of the ELISA plate and incubated for 1 hour at room temperature. Plates were washed three times with PBST. Goat anti-human Fc (Jackson catalogue #109-035-098) was diluted 1:5000 in PBST-BSA and 100 µL was added to each well and incubated for 1 hour at 4 C. Plates were washed six times with PBST. Plates were developed using the TMB Microwell Peroxidase Substrate Kit (VWR catalogue #95059-156). The reaction was stopped after 10 minutes by the addition of 1N sulfuric acid and absorbance at 450 nm was measured. The values of antibody concentration (x-axis) and absorbance at 450 nm (y-axis) were fit to a four parameter logistic regression (4PL) curve. The curve fit was then used to determine the EC50 (the midpoint of the 4PL) for each Fc variant.

Binding to Fcγ receptors IIa and IIb was measured by BioLayer Interferometry using the Octet QKe system. Briefly, FcγIIa and FcγIIb (R&D Systems catalogue #1330-CD-050 and 1875-CD-050) were diluted to 5 µg/mL in PBS. The receptors were immobilized via a C-terminal 6× histidine tag (SEQ ID NO: 2) to Ni-NTA biosensors (Pall catalogue #18-5101) for 180 seconds followed by a 60 second baseline step in PBS. The biosensors were then exposed to the various Fc variants at a concentration of 50 µg/mL in PBS for 120 seconds followed by a dissociation step in PBS for an additional 120 seconds. The max binding response during the association step for each variant was reported and compared to the wild type Fc response.

Binding to C1q was measured by ELISA. All Fc variants were tested in the context of the Motavizumab antibody. Briefly, antibodies were coated on an ELISA plate (VWR catalogue #62409-002) at 25 µg/mL (2.5 µg/well) in PBS and stored at 4° C. overnight. Plates were washed three times with PBST (1×PBS 0.05% Tween 20). Purified C1q (Quidel Corporation catalogue # A400) was titrated threefold in PBST-BSA (1×PBS 0.05% Tween20 1% BSA) from 12.5 µg/mL to 0.02 µg/mL and incubated for 90 minutes at room temperature. Liquid was aspirated from wells and polyclonal rabbit anti-human C1q (Agilent catalogue # A013602-1) was diluted in PBST-BSA to a final concentration of 1 µg/mL and 100 µL was added to each well and incubated for 1 hour at room temperature. Plates were washed three times with PBST. Polyclonal swine anti-rabbit-HRP (Agilent catalogue # P021702-2) was diluted to 0.5 µg/mL in PBST-BSA and 100 µL was added to each well and incubated for 1 hour at room temperature. Plates were washed six times with PBST. Plates were developed using the TMB Microwell Peroxidase Substrate Kit (VWR catalogue #95059-156). The reaction was stopped after 10 minutes by the addition of 1N sulfuric acid and absorbance at 450 nm was measured. The values of antibody concentration (x-axis) and absorbance at 450 nm (y-axis) were fit to a four parameter logistic regression (4PL) curve. The curve fit was then used to determine the EC50 (the midpoint of the 4PL) for each Fc variant.

The results are shown in FIGS. 17A-17D.

Example 11: CDC Activity of Engineered Antibodies

Complement dependent cytotoxicity (CDC) activity of exemplary Fc variants (Rituximab Fab) was examined.

CDC assays were performed using CD20+ Raji cells and low toxicity guinea pig complement (Cedarlane Laboratories Product # CL4051). Complement induced cell lysis was measured using the CYTOTOX 96® Non-Radioactive Cytotoxicity Assay from Promega (catalogue # G1780) following the manufacturer's protocol. All Fc variants were tested in the context of the anti-CD20 antibody, Rituximab. Briefly, antibody concentrations were titrated fourfold ranging from 20 µg/mL to 0.005 µg/mL and incubated with 20,000 target cells per well at 37° C. for 30 minutes. Complement was then added to the cells and incubated an additional 2 hours at 37° C. Additionally, cell lysis buffer provided with the CYTOTOX kit was added to control wells to measure the maximum cell lysis. A negative control antibody, Motavizumab, was used to measure the background signal of an irrelevant antibody. The background signal and maximum lysis signal were used to calculate the percent of cell lysis for each Fc variant. The values of antibody concentration (x-axis) and percent lysis (y-axis) were fit to a four parameter logistic regression curve. The curve fit was then used to determine the EC50 (concentration needed to obtain 50% lysis) and the maximum lysis for each Fc variant.

The results are shown in FIG. 18.

Example 12: ADCC Activity of Engineered Antibodies

Antibody dependent cellular cytotoxicity (ADCC) activity of exemplary Fc variants (Rituximab Fab) was examined.

ADCC assays were performed using the ADCC Reporter Bioassay with CD20+ WIL2-S target cells from Promega (catalogue # G7014) following the manufacturer's protocol. All Fc variants were tested in the context of the anti-CD20 antibody, Rituximab. Antibody concentrations were titrated fivefold ranging from 5 µg/mL to 0.0016 µg/mL. The values of antibody concentration (x-axis) and fold induction of the luminescent reporter gene (y-axis) were fit to a four parameter logistic regression (4PL) curve. The curve fit was then used to determine the EC50 (the midpoint of the 4PL) and the maximum induction for each Fc variant.

Figure 19A:
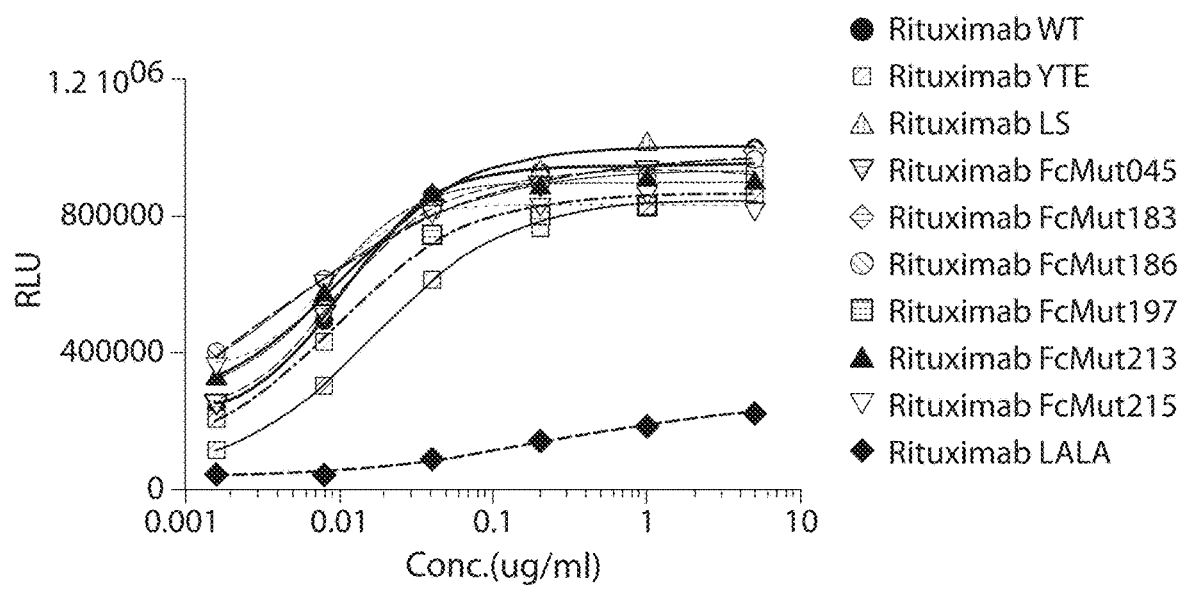
FIGS. 19A-19B depict the ADCC activity of exemplary Fc variants (Rituximab Fab).
Figure 19B:
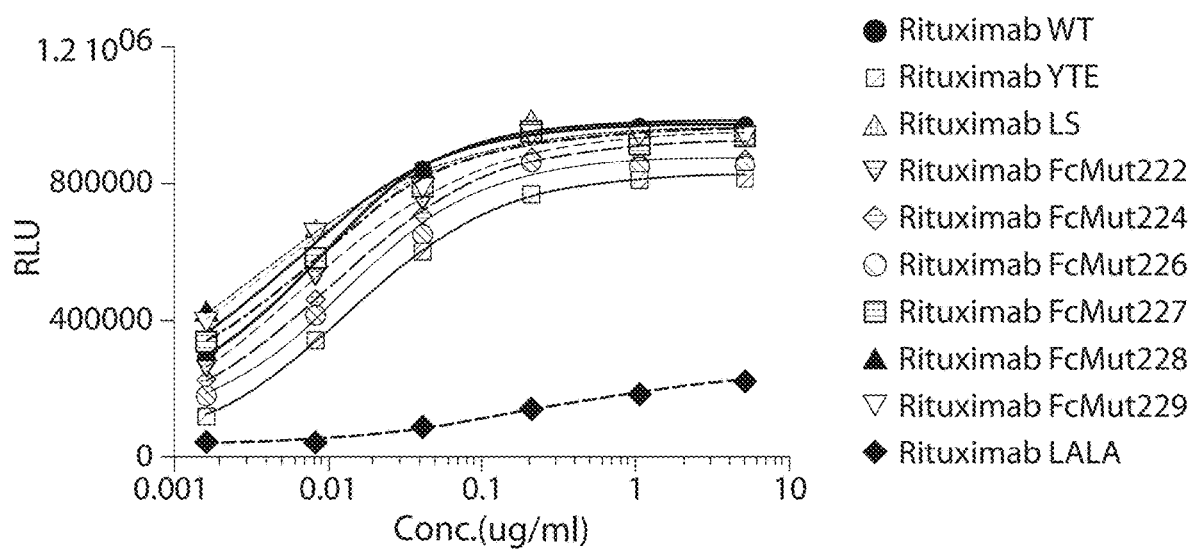

The results are shown in FIGS. 19A-19B. Exemplary Fc variants retain and in some cases enhance ADCC activity.

Example 13: ADIN Activity of Engineered Antibodies

TRIM21 is a cytosolic receptor that binds with Fc of IgG. TRIM21 plays a role in mediating intracellular recognition and neutralization of Fc bound viruses. TRIM21-mediated neutralization is known as antibody dependent intracellular neutralization (ADIN).

Binding to TRIM21 was measured by ELISA. All Fc variants were tested in the context of the Motavizumab or Actoxumab antibody. Briefly, antibodies were coated on an ELISA plate (VWR catalogue #62409-002) at 25 µg/mL (2.5 µg/well) in PBS and stored at 4° C. overnight. Plates were washed three times with PBST (1×PBS 0.05% Tween20). TRIM21-GST (Antibodies Online catalogue # ABIN1323621) was titrated threefold in PBST-BSA (1×PBS 0.05% Tween20 1% BSA) from 12.5 µg/mL to 0.02 µg/mL and incubated for 90 minutes at room temperature. Liquid was aspirated from wells and two rabbit anti-TRIM21 antibodies (AbCam catalogue # ab91423 and ab96800) were mix together in PBST-BSA at a final concentration of 1 µg/mL each and 100 µL was added to each well and incubated for 1 hour at room temperature. Plates were washed three times with PBST. Polyclonal swine anti-rabbit-HRP (Agilent catalogue # P021702-2) was diluted to 0.5 µg/mL in PBST-BSA and 100 µL was added to each well and incubated for 1 hour at room temperature. Plates were washed six times with PBST. Plates were developed using the TMB Microwell Peroxidase Substrate Kit (VWR catalogue #95059-156). The reaction was stopped after 10 minutes by the addition of 1N sulfuric acid and absorbance at 450 nm was measured. The values of antibody concentration (x-axis) and absorbance at 450 nm (y-axis) were fit to a four parameter logistic regression (4PL) curve. The curve fit was then used to determine the EC50 (the midpoint of the 4PL) for each Fc variant.

A TRIM21 binding ELISA was performed to evaluate if the Fc variants impacted binding to TRIM21. The results are shown in FIG. 26. Fc variants FcMut045, FcMut183, FcMut197, FcMut213, FcMut215, FcMut228 had TRIM21 binding EC50s that were within 1.5 fold of WT EC50.

Example 14: Enhancement of Mucosal Uptake by Fc Mutations

FcRn transports IgG across different cellular barriers such as the mucosal epithelium lining the intestine and the alveolar surfaces. Modification of FcRn binding provides a mechanism to enhance mucosal localization that confers immune protection. Exemplary Fc mutants are expected to enhance mucosal uptake in a similar fashion Example 15: Impact of FcRn Affinity Enhancing Mutations on Engagement with Fc Receptors and Effector Functions The impact of FcRn affinity enhancing mutations on binding of Fc to other receptors was experimentally evaluated. The Fc region of IgG is capable of binding to many different Fc receptors and the mechanism of action for many therapeutic antibodies relies on engagement with Fc receptors. Mutations, even at positions distant from the Fc receptor binding site, can impact engagement of Fc with receptors such as FcγRI, FcγRIIa/b, FcγRIIIa, C1q, TRIM21. While Fc receptor TRIM21 binds to a site that overlaps with FcRn binding site on CH2-CH3, other receptors such Fcγ receptors and C1q engage at the interface formed by dimeric CH2. As such any mutations introduced for enhancing half-life should be assessed for its impact on binding to other receptors. Mutations introduced to enhance half-life can The Fc variants (FcMut183, FcMut197, FcMut213, FcMut215, FcMut228, FcMut229, YTE, LS) were incorporated into rituximab Fab and together with WT rituximab, were evaluated for binding to FcγRI, FcγRIIa, FcγRIIb, FcγRIIIa, C1q and TRIM21. As shown in FIG. 24, introduction of Fc variants FcMut183, FcMut197, FcMut213, FcMut215, FcMut228 and FcMut229 did not significantly impact engagement with the tested Fc receptors.

While binding to Fc receptors is necessary for activities such as ADCC (FcγRIIIa), CDC (C1q) and ADIN (TRIM21), it may not be sufficient in mediating these activities. For example, a hexameric assembly of Fc is required to elicit CDC activity. The Fc hexamer assembly involves formation of an Fc-Fc interface, and residues involved in formation of this interface partially overlaps with FcRn binding site. As such, it was important to evaluate the impact of the Fc mutations on not just binding to Fc receptors but also activities such as CDC and ADCC. Rituximab with various Fc variants (FcMut183, FcMut197, FcMut213, FcMut215, FcMut228, FcMut229, YTE, LS, WT) were evaluated for ADCC and CDC activities as described in the methods section. The results confirmed that Fc variants FcMut183, FcMut197, FcMut213, FcMut215, FcMut228 and FcMut229 did not negatively impact ADCC activity and in fact showed a slight enhancement in CDC activity. Rituximab containing YTE had no detectable CDC activity and significantly reduced ADCC activity. Similarly another mutant FcMut197 had reduced ADCC and CDC activity. Inspects of the network map of these mutations provides an insight into the possible reason for loss of ADCC and CDC activity.

Example 16: Persistence of Optimized Fc Variants in Sera of Transgenic Mice

To evaluate whether the enhanced binding of Fc variants to human FcRn translated to increased serum persistence and longer circulating half-life life, a pharmacokinetic study of IgGs containing the different Fc variants was performed in Tg276 transgenic mice. Transgenic mouse models expressing human FcRn can be used to study PK of human Fc-containing biotherapeutics (Roopenian et al., *Methods Mol Biol,* 2010. 602: 93-104; Petkova et al., *Int Immunol,* 2006. 18(12): 1759-69). The Tg276 mice are null for mouse FcRn alpha chain and express the human FcRn alpha transgene under the control of a constitutive promoter (actin) and use the mouse β2microglobuli. The Tg276 homozygous and hemizygous mice can be used to differentiate half-lives of antibody variants. For the PK study, Tg276hemi FcRn transgenic mice were intravenously administered with 5 mg/kg of IgG (motavizumab Fab on WT or modified Fc). Retro-orbital blood collection was performed at several time points, and IgG titers were determined by quantitative ELISA. IgGs containing the engineered Fc variants persisted in serum much longer than wild-type Motavizumab (FIG. 25A). Pharmacokinetic parameters from non-compartmental analysis indicates Motavizumab with Fc variants have greater than two fold slower clearance rate and significant increases in β-phase elimination half-life and area under the curve (AUC) measurements (FIG. 25B).

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A polypeptide comprising the CH2 and CH3 domains of an Fc region, wherein the CH2 and CH3 domains of the Fc region comprises the mutations: Q311V and A378V, and one, two, or three of the mutations selected from the group consisting of: T256D, N286D, and T307R or T307Q, according to EU numbering;
  wherein the polypeptide has an increased half-life in vivo compared to an otherwise identical reference polypeptide that does not comprise the mutations of the CH2 and CH3 domains.

2. The polypeptide of claim 1, wherein the CH2 and CH3 domains of the Fc region comprises mutations chosen from any of (i)-(iv):
  (i) T256D, Q311V, and A378V;
  (ii) T307Q, Q311V, and A378V;
  (iii) T256D, N286D, T307R, Q311V, and A378V; or
  (iv) T256D, H285D, T307R, Q311V, and A378V.

3. The polypeptide of claim 1, which is an isolated polypeptide or a synthetic polypeptide.

4. A composition comprising the polypeptide of claim 1.

5. The composition of claim 4, further comprising a pharmaceutically acceptable carrier.

6. A kit comprising the polypeptide of claim 1 and instructions to use of the polypeptide.

7. A container comprising the polypeptide of claim 1.

8. The polypeptide of claim 1, wherein the CH2 and CH3 domains of the Fc region comprises mutations T256D, Q311V, and A378V.

9. The polypeptide of claim 1, wherein the CH2 and CH3 domains of the Fc region comprises mutations T307Q, Q311V, and A378V.

10. The polypeptide of claim 1, wherein the CH2 and CH3 domains of the Fc region comprises mutations in residues T256D, N286D, T307R, Q311V, and A378V.

11. The polypeptide of claim 1, which further comprises a hinge region between the CH2 and CH3 domains of the Fc region.

12. The polypeptide of claim 1, which is an antibody molecule.

13. The polypeptide of claim 12, wherein the antibody molecule is a chimeric antibody molecule or a murine antibody molecule.

14. The polypeptide of claim 12, wherein the antibody molecule is a human antibody molecule or a humanized antibody molecule.

15. The polypeptide of claim 1, which further comprises a heavy chain immunoglobulin variable region, a light chain immunoglobulin variable region, or both.

16. The polypeptide of claim 1, which is an immunoglobulin chain or a fragment thereof.

17. The polypeptide of claim 1, which is a fusion protein.

18. The polypeptide of claim 1, wherein the reference polypeptide comprises a wild-type Fc region.

19. The polypeptide of claim 1, wherein the half-life is determined in an animal model.

20. The polypeptide of claim 1, wherein the half-life is a circulating half-life in a human or a non-human primate.

21. The polypeptide of claim 1, wherein the CH2 and CH3 domains of the Fc region comprises two or three of the mutations selected from the group consisting of: T256D, N286D, and T307R or T307Q.

22. The polypeptide of claim 1, wherein the CH2 and CH3 domains of the Fc region comprises three of the mutations selected from the group consisting of: T256D, N286D, and T307R or T307Q.

* * * * *